US012127777B2

(12) United States Patent
Carroll et al.

(10) Patent No.: US 12,127,777 B2
(45) Date of Patent: Oct. 29, 2024

(54) ENERGY DELIVERY MITIGATIONS FOR MODULAR ENERGY SYSTEMS

(71) Applicant: Cilag GmbH International, Zug (CH)

(72) Inventors: Andrew W. Carroll, Cincinnati, OH (US); Eitan T. Wiener, Loveland, OH (US); Jeffrey L. Aldridge, Lebanon, OH (US); Joshua M. Henderson, Montgomery, OH (US); Joshua P. Morgan, Loveland, OH (US)

(73) Assignee: Cilag GmbH International, Zug (CH)

( * ) Notice: Subject to any disclaimer, the term of this patent is extended or adjusted under 35 U.S.C. 154(b) by 783 days.

(21) Appl. No.: 17/217,429

(22) Filed: Mar. 30, 2021

(65) Prior Publication Data

US 2022/0313338 A1 Oct. 6, 2022

(51) Int. Cl.
| | | |
|---|---|---|
| *A61B 18/00* | (2006.01) | |
| *A61B 34/00* | (2016.01) | |
| *A61B 90/00* | (2016.01) | |
| *G06F 1/26* | (2006.01) | |
| *H02J 3/00* | (2006.01) | |
| *H03M 1/34* | (2006.01) | |

(52) U.S. Cl.
CPC .............. *A61B 18/00* (2013.01); *G06F 1/266* (2013.01); *H02J 3/001* (2020.01); *H03M 1/34* (2013.01); *A61B 2018/00708* (2013.01); *A61B 34/25* (2016.02); *A61B 90/37* (2016.02); *A61B 2090/372* (2016.02); *H02J 2310/23* (2020.01)

(58) Field of Classification Search
CPC ..................... G06F 1/266; H02J 3/001; A61B 2018/00916; A61B 2018/00922; A61B 2018/00958; A61B 2560/0276
See application file for complete search history.

(56) References Cited

U.S. PATENT DOCUMENTS

| | | |
|---|---|---|
| 4,171,700 A | 10/1979 | Farin |
| 4,849,752 A | 7/1989 | Bryant |

(Continued)

FOREIGN PATENT DOCUMENTS

| | | |
|---|---|---|
| EP | 0408160 A1 | 1/1991 |
| EP | 0473987 A1 | 3/1992 |

(Continued)

OTHER PUBLICATIONS

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

(Continued)

*Primary Examiner* — Ronald Hupczey, Jr.

(57) ABSTRACT

Disclosed is an isolated interface circuit for a modular energy system. A comparator is configured to couple to a switch and a reference voltage, and an output. A duplicate comparator is configured to couple to the switch and the reference voltage. An expander circuit is coupled to the comparator and the duplicate comparator. An isolator circuit is coupled to the expander circuit. A controller is coupled to the isolator circuit. The controller is configured to compare the output of the comparator with the output of the duplicate comparator and determine activation or deactivation of a surgical instrument coupled to the controller based on the comparison.

20 Claims, 30 Drawing Sheets

(56) References Cited

U.S. PATENT DOCUMENTS

| | | |
|---|---|---|
| D303,787 S | 10/1989 | Messenger et al. |
| D327,061 S | 6/1992 | Soren et al. |
| 5,189,277 A | 2/1993 | Boisvert et al. |
| 5,204,669 A | 4/1993 | Dorfe et al. |
| 5,318,563 A | 6/1994 | Malis et al. |
| D379,346 S | 5/1997 | Mieki |
| 5,693,042 A | 12/1997 | Boiarski et al. |
| 5,724,468 A | 3/1998 | Leone et al. |
| 6,269,411 B1 | 7/2001 | Reasoner |
| 6,584,358 B2 | 6/2003 | Carter et al. |
| 6,611,793 B1 | 8/2003 | Burnside et al. |
| 6,731,514 B2 | 5/2004 | Evans |
| 6,913,471 B2 | 7/2005 | Smith |
| 7,009,511 B2 | 3/2006 | Mazar et al. |
| 7,044,949 B2 | 5/2006 | Orszulak et al. |
| 7,217,269 B2 | 5/2007 | El-Galley et al. |
| 7,252,664 B2 | 8/2007 | Nasab et al. |
| 7,344,532 B2 | 3/2008 | Goble et al. |
| 7,353,068 B2 | 4/2008 | Tanaka et al. |
| 7,408,439 B2 | 8/2008 | Wang et al. |
| D579,876 S | 11/2008 | Novotney et al. |
| D583,328 S | 12/2008 | Chiang |
| 7,496,418 B2 | 2/2009 | Kim et al. |
| D589,447 S | 3/2009 | Sasada et al. |
| 7,518,502 B2 | 4/2009 | Austin et al. |
| 7,563,259 B2 | 7/2009 | Takahashi |
| 7,637,907 B2 | 12/2009 | Blaha |
| 7,757,028 B2 | 7/2010 | Druke et al. |
| D631,252 S | 1/2011 | Leslie |
| 7,932,826 B2 | 4/2011 | Fritchie et al. |
| 7,945,065 B2 | 5/2011 | Menzl et al. |
| 7,945,342 B2 | 5/2011 | Tsai et al. |
| 7,982,776 B2 | 7/2011 | Dunki-Jacobs et al. |
| 7,995,045 B2 | 8/2011 | Dunki-Jacobs |
| 8,019,094 B2 | 9/2011 | Hsieh et al. |
| D655,678 S | 3/2012 | Kobayashi et al. |
| D657,368 S | 4/2012 | Magee et al. |
| 8,239,066 B2 | 8/2012 | Jennings et al. |
| D667,838 S | 9/2012 | Magee et al. |
| D675,164 S | 1/2013 | Kobayashi et al. |
| D676,392 S | 2/2013 | Gassauer |
| D678,196 S | 3/2013 | Miyauchi et al. |
| D678,304 S | 3/2013 | Yakoub et al. |
| 8,423,182 B2 | 4/2013 | Robinson et al. |
| D687,146 S | 7/2013 | Juzkiw et al. |
| 8,540,709 B2 | 9/2013 | Allen |
| 8,567,393 B2 | 10/2013 | Hickle et al. |
| D704,839 S | 5/2014 | Juzkiw et al. |
| 8,795,001 B1 | 8/2014 | Lam et al. |
| 8,819,581 B2 | 8/2014 | Nakamura et al. |
| D716,333 S | 10/2014 | Chotin et al. |
| 8,917,513 B1 | 12/2014 | Hazzard |
| 8,920,186 B2 | 12/2014 | Shishikura |
| 8,968,296 B2 | 3/2015 | McPherson |
| 8,986,288 B2 | 3/2015 | Konishi |
| D729,267 S | 5/2015 | Yoo et al. |
| 9,055,870 B2 | 6/2015 | Meador et al. |
| 9,160,853 B1 | 10/2015 | Daddi et al. |
| 9,168,054 B2 | 10/2015 | Turner et al. |
| 9,168,091 B2 | 10/2015 | Janssen et al. |
| 9,198,711 B2 | 12/2015 | Joseph |
| 9,226,766 B2 | 1/2016 | Aldridge et al. |
| 9,226,791 B2 | 1/2016 | McCarthy et al. |
| 9,237,921 B2 | 1/2016 | Messerly et al. |
| 9,265,429 B2 | 2/2016 | St. Pierre et al. |
| 9,277,961 B2 | 3/2016 | Panescu et al. |
| 9,277,969 B2 | 3/2016 | Brannan et al. |
| 9,345,481 B2 | 5/2016 | Hall et al. |
| 9,345,900 B2 | 5/2016 | Wu et al. |
| 9,463,646 B2 | 10/2016 | Payne et al. |
| 9,474,565 B2 | 10/2016 | Shikhman et al. |
| D772,252 S | 11/2016 | Myers et al. |
| 9,486,271 B2 | 11/2016 | Dunning |
| 9,498,194 B2 * | 11/2016 | Moe .................. A61B 17/00 |
| 9,532,827 B2 | 1/2017 | Morgan et al. |
| 9,600,031 B2 | 3/2017 | Kaneko et al. |
| 9,603,277 B2 | 3/2017 | Morgan et al. |
| D783,675 S | 4/2017 | Yagisawa et al. |
| D784,270 S | 4/2017 | Bhattacharya |
| 9,713,503 B2 | 7/2017 | Goldschmidt |
| 9,750,563 B2 | 9/2017 | Shikhman et al. |
| 9,782,214 B2 | 10/2017 | Houser et al. |
| 9,867,670 B2 | 1/2018 | Brannan et al. |
| 9,907,196 B2 | 2/2018 | Susini et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| 10,098,527 B2 | 10/2018 | Weisenburgh, II et al. |
| 10,105,470 B2 | 10/2018 | Reasoner et al. |
| D834,541 S | 11/2018 | You et al. |
| 10,117,702 B2 | 11/2018 | Danziger et al. |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,061 B2 | 1/2019 | Berry et al. |
| 10,201,365 B2 | 2/2019 | Boudreaux et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,499,847 B2 | 12/2019 | Latimer et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,624,667 B2 | 4/2020 | Faller et al. |
| 10,624,691 B2 | 4/2020 | Wiener et al. |
| 10,675,100 B2 | 6/2020 | Frushour |
| 10,687,884 B2 | 6/2020 | Wiener et al. |
| 10,743,872 B2 | 8/2020 | Leimbach et al. |
| 10,772,673 B2 | 9/2020 | Allen, IV et al. |
| 10,881,399 B2 | 1/2021 | Shelton, IV et al. |
| 10,898,256 B2 | 1/2021 | Yates et al. |
| 10,932,772 B2 | 3/2021 | Shelton, IV et al. |
| 10,950,982 B2 | 3/2021 | Regnier et al. |
| D924,139 S | 7/2021 | Jayme |
| D928,725 S | 8/2021 | Oberkircher et al. |
| D928,726 S | 8/2021 | Asher et al. |
| 11,077,312 B2 | 8/2021 | Sturman et al. |
| 11,185,379 B2 | 11/2021 | Shuma et al. |
| D939,545 S | 12/2021 | Oberkircher et al. |
| 11,659,023 B2 | 5/2023 | Shelton, IV et al. |
| 11,712,309 B2 | 8/2023 | Barak et al. |
| 11,857,252 B2 | 1/2024 | Geresy et al. |
| 11,950,860 B2 | 4/2024 | Morgan et al. |
| 11,963,727 B2 | 4/2024 | Morgan et al. |
| 11,968,776 B2 | 4/2024 | Jayme et al. |
| 11,978,554 B2 | 5/2024 | Oberkircher et al. |
| 11,980,411 B2 | 5/2024 | Leuck et al. |
| 2002/0115917 A1* | 8/2002 | Honda .................. A61B 17/00 600/301 |
| 2002/0156466 A1* | 10/2002 | Sakurai .............. A61B 1/00016 606/1 |
| 2005/0165390 A1 | 7/2005 | Mauti et al. |
| 2005/0251233 A1 | 11/2005 | Kanzius |
| 2006/0136622 A1 | 6/2006 | Rouvelin et al. |
| 2007/0282321 A1 | 12/2007 | Shah et al. |
| 2008/0129465 A1 | 6/2008 | Rao |
| 2009/0234352 A1 | 9/2009 | Behnke et al. |
| 2010/0069939 A1 | 3/2010 | Konishi |
| 2010/0120266 A1 | 5/2010 | Rimborg |
| 2010/0198200 A1 | 8/2010 | Horvath |
| 2011/0125149 A1 | 5/2011 | El-Galley et al. |
| 2011/0273465 A1 | 11/2011 | Konishi et al. |
| 2011/0306840 A1 | 12/2011 | Allen et al. |
| 2013/0268283 A1 | 10/2013 | Vann et al. |
| 2014/0009894 A1 | 1/2014 | Yu |
| 2014/0226572 A1 | 8/2014 | Thota et al. |
| 2014/0263552 A1 | 9/2014 | Hall et al. |
| 2016/0287312 A1 | 10/2016 | Tegg et al. |
| 2017/0202595 A1 | 7/2017 | Shelton, IV |
| 2017/0296213 A1 | 10/2017 | Swensgard et al. |
| 2018/0042659 A1 | 2/2018 | Rupp et al. |

(56) References Cited

U.S. PATENT DOCUMENTS

| | | |
|---|---|---|
| 2018/0065248 A1 | 3/2018 | Barral et al. |
| 2018/0221005 A1 | 8/2018 | Hamel et al. |
| 2018/0333207 A1 | 11/2018 | Moctezuma De la Barrera |
| 2019/0000478 A1 | 1/2019 | Messerly et al. |
| 2019/0224434 A1 | 7/2019 | Silver et al. |
| 2019/0278262 A1 | 9/2019 | Taylor et al. |
| 2020/0038120 A1 | 2/2020 | Ziraknejad et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0305924 A1 | 10/2020 | Carroll |
| 2020/0305945 A1 | 10/2020 | Morgan et al. |
| 2020/0314569 A1 | 10/2020 | Morgan et al. |
| 2021/0212717 A1 | 7/2021 | Yates et al. |
| 2022/0313341 A1 | 10/2022 | Wiener et al. |
| 2022/0313369 A1 | 10/2022 | Oberkircher et al. |
| 2022/0313372 A1 | 10/2022 | Herman et al. |
| 2022/0313373 A1 | 10/2022 | Morgan et al. |
| 2022/0317750 A1 | 10/2022 | Jayme et al. |
| 2022/0317751 A1 | 10/2022 | Samuel et al. |
| 2022/0318179 A1 | 10/2022 | Morgan et al. |
| 2022/0319685 A1 | 10/2022 | Vachon et al. |
| 2022/0321059 A1 | 10/2022 | Samuel et al. |

FOREIGN PATENT DOCUMENTS

| | | |
|---|---|---|
| EP | 0929263 B1 | 7/1999 |
| EP | 2942023 A2 | 11/2015 |
| JP | 2001029353 A | 2/2001 |
| WO | WO-0112089 A1 | 2/2001 |
| WO | WO-2008053485 A1 | 5/2008 |
| WO | WO-2014031800 A1 | 2/2014 |
| WO | WO-2014071184 A1 | 5/2014 |
| WO | WO-2017058617 | 4/2017 |
| WO | WO-2018116247 A1 | 6/2018 |

OTHER PUBLICATIONS

IEEE Std 802.Mar. 2012 (Revision of IEEE Std 802.3-2008, published Dec. 28, 2012.

"ATM-MPLS Network Interworking Version 2.0, af-aic-0178.001" ATM Standard, The ATM Forum Technical Committe, published Aug. 2003.

* cited by examiner

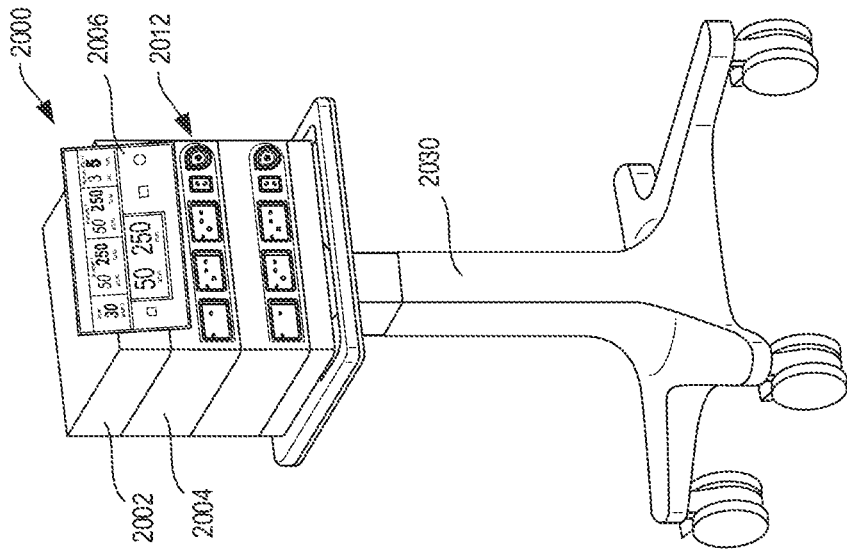
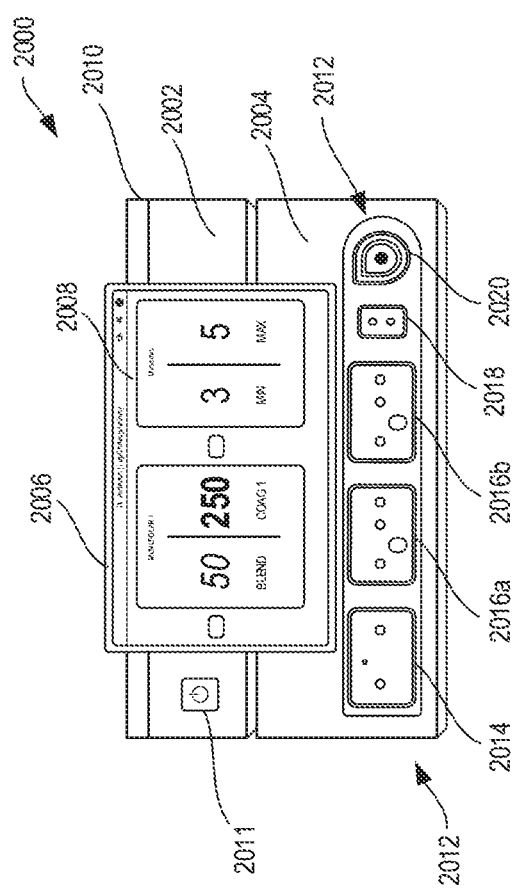
FIG. 7B
FIG. 7A

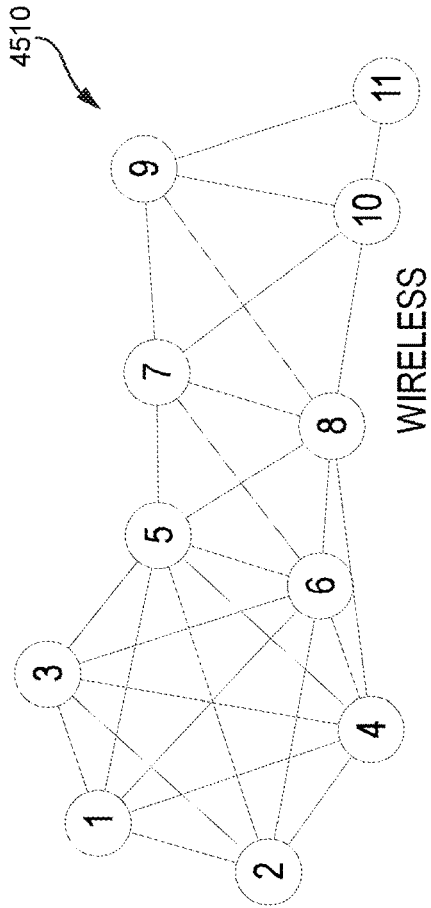
FIG. 24
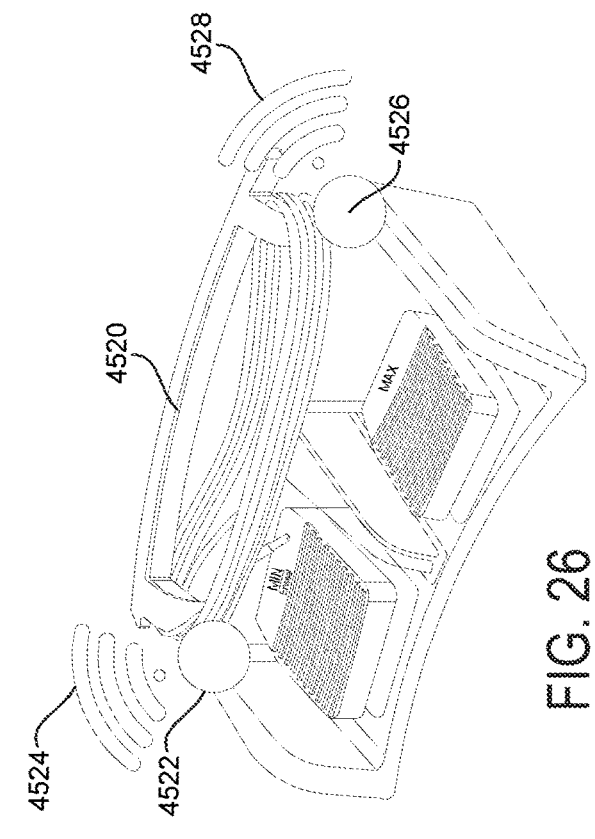
FIG. 25
FIG. 26

ENERGY DELIVERY MITIGATIONS FOR MODULAR ENERGY SYSTEMS

BACKGROUND

The present disclosure relates to various surgical systems, including modular electrosurgical and/or ultrasonic surgical systems. Operating rooms (ORs) are in need of streamlined capital solutions because ORs are a tangled web of cords, devices, and people due to the number of different devices that are needed to complete each surgical procedure. This is a reality of every OR in every market throughout the globe. Capital equipment is a major offender in creating clutter within ORs because most capital equipment performs one task or job, and each type of capital equipment requires unique techniques or methods to use and has a unique user interface. Accordingly, there are unmet consumer needs for capital equipment and other surgical technology to be consolidated in order to decrease the equipment footprint within the OR, streamline the equipment's interfaces, and improve surgical staff efficiency during a surgical procedure by reducing the number of devices that surgical staff members need to interact with.

A modular energy system is designed to interface to various accessories such as a footswitch. Communication between the modular energy system and the accessory should be mitigated to prevent an erroneous signal from the accessary to reach the modular energy system. An erroneous signal from the accessory may result in an erroneous activation an electrosurgical instrument, ultrasonic instrument, or an instrument that is a combination thereof, connected to the energy module of the modular energy system. Accordingly, there is a need to mitigate the interface between the accessory and the modular energy system. Furthermore, there is a need to improve the reliability of wireless communications in an operating room (OR) environment where interference may block wireless signals from the accessory to reach the modular energy system. Accordingly, there is a need for a robust wireless communication in an operating room (OR) environment.

SUMMARY

In one aspect, the present disclosure provides an isolated interface circuit for a modular energy system. The isolated interface circuit comprises a comparator comprising a first input configured to couple to a switch, a second input configured to couple to a reference voltage, and an output; a duplicate comparator comprising a first input configured to couple to the switch, a second input configured to couple to the reference voltage, and an output; an expander circuit comprising at least two inputs, wherein the output of the comparator is coupled to one of the at least two inputs of the expander circuit, and wherein the output of the duplicate comparator is coupled to other of the at least two inputs of the expander circuit, the expander circuit comprising an output; an isolator circuit comprising an input and an output, wherein the input is coupled to the output of the expander circuit; and a controller coupled to the output of the isolator circuit, wherein the controller is configured to: compare the output of the comparator with the output of the duplicate comparator; and determine activation or deactivation of a surgical instrument coupled to the controller based on the comparison.

In another aspect, the present disclosure provides an isolated interface circuit for a modular energy system. The isolated interface circuit comprises a first comparator comprising a first input configured to couple to a first switch, a second input configured to couple to a reference voltage, and an output; a second comparator comprising a first input configured to couple to a second switch, a second input configured to couple to the reference voltage, and an output; a first duplicate comparator comprising a first input configured to couple to the first switch, a second input configured to couple to the reference voltage, and an output; a second duplicate comparator comprising a first input configured to couple to the second switch, a second input configured to couple to the reference voltage, and an output; an expander circuit comprising at least four inputs, wherein each of the outputs of the first and second comparators is coupled to an input of the expander circuit, and wherein each of the outputs of the first and second duplicate comparators is coupled an input of the expander circuit, the expander circuit comprising an output; an isolator circuit comprising an input and an output, wherein the input is coupled to the output of the expander circuit; and a controller coupled to the output of the isolator circuit, wherein the controller is configure to: compare the output of the first comparator with the output of the first duplicate comparator; compare the output of the second comparator with the output of the second duplicate comparator; and determine activation or deactivation of a surgical instrument coupled to the controller based on the comparison.

In yet another aspect, the present disclosure provides a method of mitigating erroneous outputs from an isolated interface circuit for a modular energy system. The method comprises receiving, at a first input of a first comparator, a state of a first switch of a first footswitch coupled to the first input of the first comparator and a reference voltage coupled to a second input of the first comparator; receiving, at a first input of a first duplicate comparator, the state of the first switch coupled to the first input of the first duplicate comparator and the reference voltage coupled to a second input of the first duplicate comparator; comparing, by a controller coupled to outputs of the first comparator and the first duplicate comparator, the output of the first comparator with the output of the first duplicate comparator; and determining, by the controller, activation or deactivation of a surgical instrument coupled to the controller based on the comparison.

FIGURES

The various aspects described herein, both as to organization and methods of operation, together with further objects and advantages thereof, may best be understood by reference to the following description, taken in conjunction with the accompanying drawings as follows.

FIG. 7A is a first illustrative modular energy system configuration including a header module and a display screen that renders a graphical user interface (GUI) for relaying information regarding modules connected to the header module, in accordance with at least one aspect of the present disclosure.

FIG. 7B is the modular energy system shown in FIG. 7A mounted to a cart, in accordance with at least one aspect of the present disclosure.

FIG. 24 is a schematic representation of a wireless mesh network, in accordance with at least one aspect of the present disclosure.

FIG. 25 is a bock diagram of a modular energy system comprising multiple radios, in accordance with at least one aspect of the present disclosure.

FIG. 26 is a diagram of a footswitch comprising multiple radios, in accordance with at least aspect of the present disclosure.

Corresponding reference characters indicate corresponding parts throughout the several views. The exemplifications set out herein illustrate various disclosed aspects, in one form, and such exemplifications are not to be construed as limiting the scope thereof in any manner.

DESCRIPTION

Figure 1:
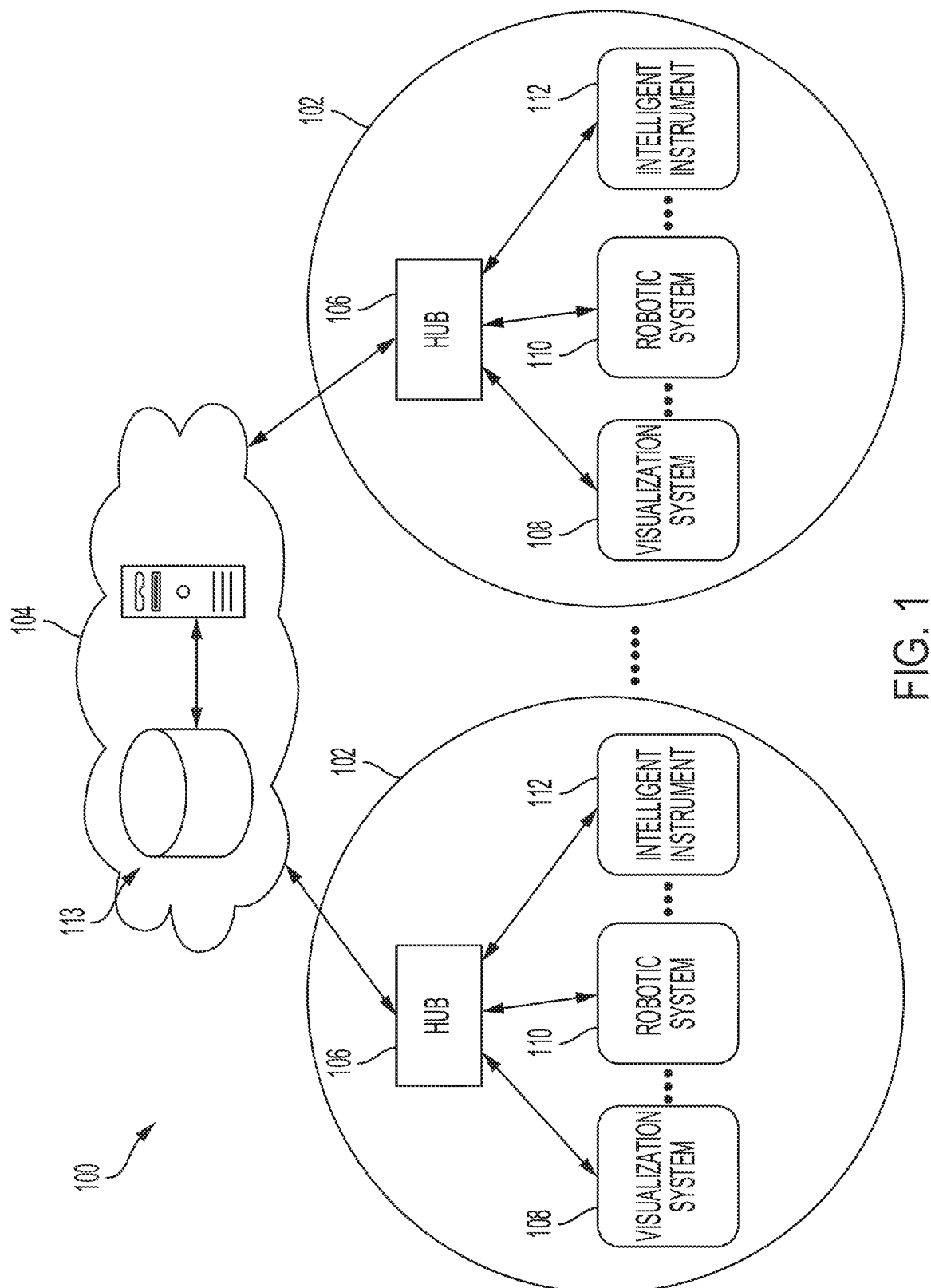
FIG. 1 is a block diagram of a computer-implemented interactive surgical system, in accordance with at least one aspect of the present disclosure.

Applicant of the present application owns the following U.S. patent applications filed Mar. 30, 2021, the disclosure of each of which is herein incorporated by reference in its entirety:

U.S. patent application Ser. No. 17/217,394, titled METHOD FOR MECHANICAL PACKAGING FOR MODULAR ENERGY SYSTEM, now U.S. Pat. No. 11,968,776;

U.S. patent application Ser. No. 17/217,402, titled BACKPLANE CONNECTOR ATTACHMENT MECHANISM FOR MODULAR ENERGY SYSTEM, now U.S. Patent Application Publication No. 2022/0317750;

U.S. patent application Ser. No. 17/217,436, titled BEZEL WITH LIGHT BLOCKING FEATURES FOR MODULAR ENERGY SYSTEM, now U.S. Pat. No. 11,857,252;

U.S. patent application Ser. No. 17/217,446, titled HEADER FOR MODULAR ENERGY SYSTEM, now U.S. Pat. No. 11,980,411;

U.S. patent application Ser. No. 17/217,403, titled SURGICAL PROCEDURALIZATION VIA MODULAR ENERGY SYSTEM, now U.S. Patent Application Publication No. 2022/0313341;

U.S. patent application Ser. No. 17/217,424, titled METHOD FOR ENERGY DELIVERY FOR MODULAR ENERGY SYSTEM, now U.S. Patent Application Publication No. 2022/0317751;

U.S. patent application Ser. No. 17/217,439, titled MODULAR ENERGY SYSTEM WITH DUAL AMPLIFIERS AND TECHNIQUES FOR UPDATING PARAMETERS THEREOF, now U.S. Patent Application Publication No. 2022/0321059;

U.S. patent application Ser. No. 17/217,471, titled MODULAR ENERGY SYSTEM WITH MULTI-ENERGY PORT SPLITTER FOR MULTIPLE ENERGY DEVICES, now U.S. Patent Application Publication No. 2022/0313373;

U.S. patent application Ser. No. 17/217,385, titled METHOD FOR INTELLIGENT INSTRUMENTS FOR MODULAR ENERGY SYSTEM, now U.S. Patent Application Publication No. 2022/0313369;

U.S. patent application Ser. No. 17/217,392, titled RADIO FREQUENCY IDENTIFICATION TOKEN FOR WIRELESS SURGICAL INSTRUMENTS, now U.S. Pat. No. 11,978,554;

U.S. patent application Ser. No. 17/217,397, titled INTELLIGENT DATA PORTS FOR MODULAR ENERGY SYSTEMS, now U.S. Patent Application Publication No. 2022/0318179;

U.S. patent application Ser. No. 17/217,405, titled METHOD FOR SYSTEM ARCHITECTURE FOR MODULAR ENERGY SYSTEM, now U.S. Pat. No. 11,963,727;

U.S. patent application Ser. No. 17/217,423, titled USER INTERFACE MITIGATION TECHNIQUES FOR MODULAR ENERGY SYSTEMS, now U.S. Pat. No. 11,950,860;

U.S. patent application Ser. No. 17/217,449, titled ARCHITECTURE FOR MODULAR ENERGY SYSTEM, now U.S. Pat. No. 12,004,824; and U.S. patent application Ser. No. 17/217,461, titled MODULAR ENERGY SYSTEM WITH HARDWARE MITIGATED COMMUNICATION, now U.S. Patent Application Publication No. 2022/0319685.

Applicant of the present application owns the following U.S. patent applications filed Sep. 5, 2019, the disclosure of each of which is herein incorporated by reference in its entirety:

U.S. patent application Ser. No. 16/562,144, titled METHOD FOR CONTROLLING A MODULAR ENERGY SYSTEM USER INTERFACE, now U.S. Patent Application Publication No. 2020/0078106;

U.S. patent application Ser. No. 16/562,151, titled PASSIVE HEADER MODULE FOR A MODULAR ENERGY SYSTEM, now U.S. Patent Application Publication No. 2020/0078110;

U.S. patent application Ser. No. 16/562,157, titled CONSOLIDATED USER INTERFACE FOR MODULAR ENERGY SYSTEM, now U.S. Patent Application Publication No. 2020/0081585;

U.S. patent application Ser. No. 16/562,159, titled AUDIO TONE CONSTRUCTION FOR AN ENERGY MODULE OF A MODULAR ENERGY SYSTEM, now U.S. Patent Application Publication No. 2020/0314569;

U.S. patent application Ser. No. 16/562,163, titled ADAPTABLY CONNECTABLE AND REASSIGNABLE SYSTEM ACCESSORIES FOR MODULAR ENERGY SYSTEM, now U.S. Patent Application Publication No. 2020/0078111;

U.S. patent application Ser. No. 16/562,123, titled METHOD FOR CONSTRUCTING AND USING A MODULAR SURGICAL ENERGY SYSTEM WITH MULTIPLE DEVICES, now U.S. Patent Application Publication No. 2020/0100830;

U.S. patent application Ser. No. 16/562,135, titled METHOD FOR CONTROLLING AN ENERGY MODULE OUTPUT, now U.S. Patent Application Publication No. 2020/0078076;

U.S. patent application Ser. No. 16/562,180, titled ENERGY MODULE FOR DRIVING MULTIPLE ENERGY MODALITIES, now U.S. Patent Application Publication No. 2020/0078080;

U.S. patent application Ser. No. 16/562,184, titled GROUNDING ARRANGEMENT OF ENERGY MODULES, now U.S. Patent Application Publication No. 2020/0078081;

U.S. patent application Ser. No. 16/562,188, titled BACKPLANE CONNECTOR DESIGN TO CONNECT STACKED ENERGY MODULES, now U.S. Patent Application Publication No. 2020/0078116;

U.S. patent application Ser. No. 16/562,195, titled ENERGY MODULE FOR DRIVING MULTIPLE ENERGY MODALITIES THROUGH A PORT, now U.S. Patent Application Publication No. 20200078117;

U.S. patent application Ser. No. 16/562,202 titled SURGICAL INSTRUMENT UTILIZING DRIVE SIGNAL TO POWER SECONDARY FUNCTION, now U.S. Patent Application Publication No. 2020/0078082;

U.S. patent application Ser. No. 16/562,142, titled METHOD FOR ENERGY DISTRIBUTION IN A SURGICAL MODULAR ENERGY SYSTEM, now U.S. Patent Application Publication No. 2020/0078070;

U.S. patent application Ser. No. 16/562,169, titled SURGICAL MODULAR ENERGY SYSTEM WITH A SEGMENTED BACKPLANE, now U.S. Patent Application Publication No. 2020/0078112;

U.S. patent application Ser. No. 16/562,185, titled SURGICAL MODULAR ENERGY SYSTEM WITH FOOTER MODULE, now U.S. Patent Application Publication No. 2020/0078115;

U.S. patent application Ser. No. 16/562,203, titled POWER AND COMMUNICATION MITIGATION ARRANGEMENT FOR MODULAR SURGICAL ENERGY SYSTEM, now U.S. Patent Application Publication No. 2020/0078118;

U.S. patent application Ser. No. 16/562,212, titled MODULAR SURGICAL ENERGY SYSTEM WITH MODULE POSITIONAL AWARENESS SENSING WITH VOLTAGE DETECTION, now U.S. Patent Application Publication No. 2020/0078119;

U.S. patent application Ser. No. 16/562,234, titled MODULAR SURGICAL ENERGY SYSTEM WITH MODULE POSITIONAL AWARENESS SENSING WITH TIME COUNTER, now U.S. Patent Application Publication No. 2020/0305945;

U.S. patent application Ser. No. 16/562,243, titled MODULAR SURGICAL ENERGY SYSTEM WITH MODULE POSITIONAL AWARENESS WITH DIGITAL LOGIC, now U.S. Patent Application Publication No. 2020/0078120;

U.S. patent application Ser. No. 16/562,125, titled METHOD FOR COMMUNICATING BETWEEN MODULES AND DEVICES IN A MODULAR SURGICAL SYSTEM, now U.S. Patent Application Publication No. 2020/0100825;

U.S. patent application Ser. No. 16/562,137, titled FLEXIBLE HAND-SWITCH CIRCUIT, now U.S. Patent Application Publication No. 2020/0106220;

U.S. patent application Ser. No. 16/562,143, titled FIRST AND SECOND COMMUNICATION PROTOCOL ARRANGEMENT FOR DRIVING PRIMARY AND SECONDARY DEVICES THROUGH A SINGLE PORT, now U.S. Patent Application Publication No. 2020/0090808;

U.S. patent application Ser. No. 16/562,148, titled FLEXIBLE NEUTRAL ELECTRODE, now U.S. Patent Application Publication No. 2020/0078077;

U.S. patent application Ser. No. 16/562,154, titled SMART RETURN PAD SENSING THROUGH MODULATION OF NEAR FIELD COMMUNICATION AND CONTACT QUALITY MONITORING SIGNALS, now U.S. Patent Application Publication No. 2020/0078089;

U.S. patent application Ser. No. 16/562,162, titled AUTOMATIC ULTRASONIC ENERGY ACTIVATION CIRCUIT DESIGN FOR MODULAR SURGICAL SYSTEMS, now U.S. Patent Application Publication No. 2020/0305924;

U.S. patent application Ser. No. 16/562,167, titled COORDINATED ENERGY OUTPUTS OF SEPARATE BUT CONNECTED MODULES, now U.S. Patent Application Publication No. 2020/0078078;

U.S. patent application Ser. No. 16/562,170, titled MANAGING SIMULTANEOUS MONOPOLAR OUTPUTS USING DUTY CYCLE AND SYNCHRONIZATION, now U.S. Patent Application Publication No. 2020/0078079;

U.S. patent application Ser. No. 16/562,172, titled PORT PRESENCE DETECTION SYSTEM FOR MODULAR ENERGY SYSTEM, now U.S. Patent Application Publication No. 2020/0078113;

U.S. patent application Ser. No. 16/562,175, titled INSTRUMENT TRACKING ARRANGEMENT BASED ON REAL TIME CLOCK INFORMATION, now U.S. Patent Application Publication No. 2020/0078071;

U.S. patent application Ser. No. 16/562,177, titled REGIONAL LOCATION TRACKING OF COMPONENTS OF A MODULAR ENERGY SYSTEM, now U.S. Patent Application Publication No. 2020/0078114;

U.S. Design patent application Ser. No. 29/704,610, titled ENERGY MODULE;

U.S. Design patent application Ser. No. 29/704,614, titled ENERGY MODULE MONOPOLAR PORT WITH FOURTH SOCKET AMONG THREE OTHER SOCKETS;

U.S. Design patent application Ser. No. 29/704,616, titled BACKPLANE CONNECTOR FOR ENERGY MODULE; and U.S. Design patent application Ser. No. 29/704,617, titled ALERT SCREEN FOR ENERGY MODULE.

Applicant of the present application owns the following U.S. Patent Provisional Applications filed Mar. 29, 2019, the disclosure of each of which is herein incorporated by reference in its entirety:

U.S. Provisional Patent Application Ser. No. 62/826,584, titled MODULAR SURGICAL PLATFORM ELECTRICAL ARCHITECTURE;

U.S. Provisional Patent Application Ser. No. 62/826,587, titled MODULAR ENERGY SYSTEM CONNECTIVITY;

U.S. Provisional Patent Application Ser. No. 62/826,588, titled MODULAR ENERGY SYSTEM INSTRUMENT COMMUNICATION TECHNIQUES; and U.S. Provisional Patent Application Ser. No. 62/826,592, titled MODULAR ENERGY DELIVERY SYSTEM.

Applicant of the present application owns the following U.S. Patent Provisional Application filed Sep. 7, 2018, the disclosure of which is herein incorporated by reference in its entirety:

U.S. Provisional Patent Application Ser. No. 62/728,480, titled MODULAR ENERGY SYSTEM AND USER INTERFACE.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Surgical System Hardware

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, 0, and P are integers greater than or equal to one.

Figure 2:
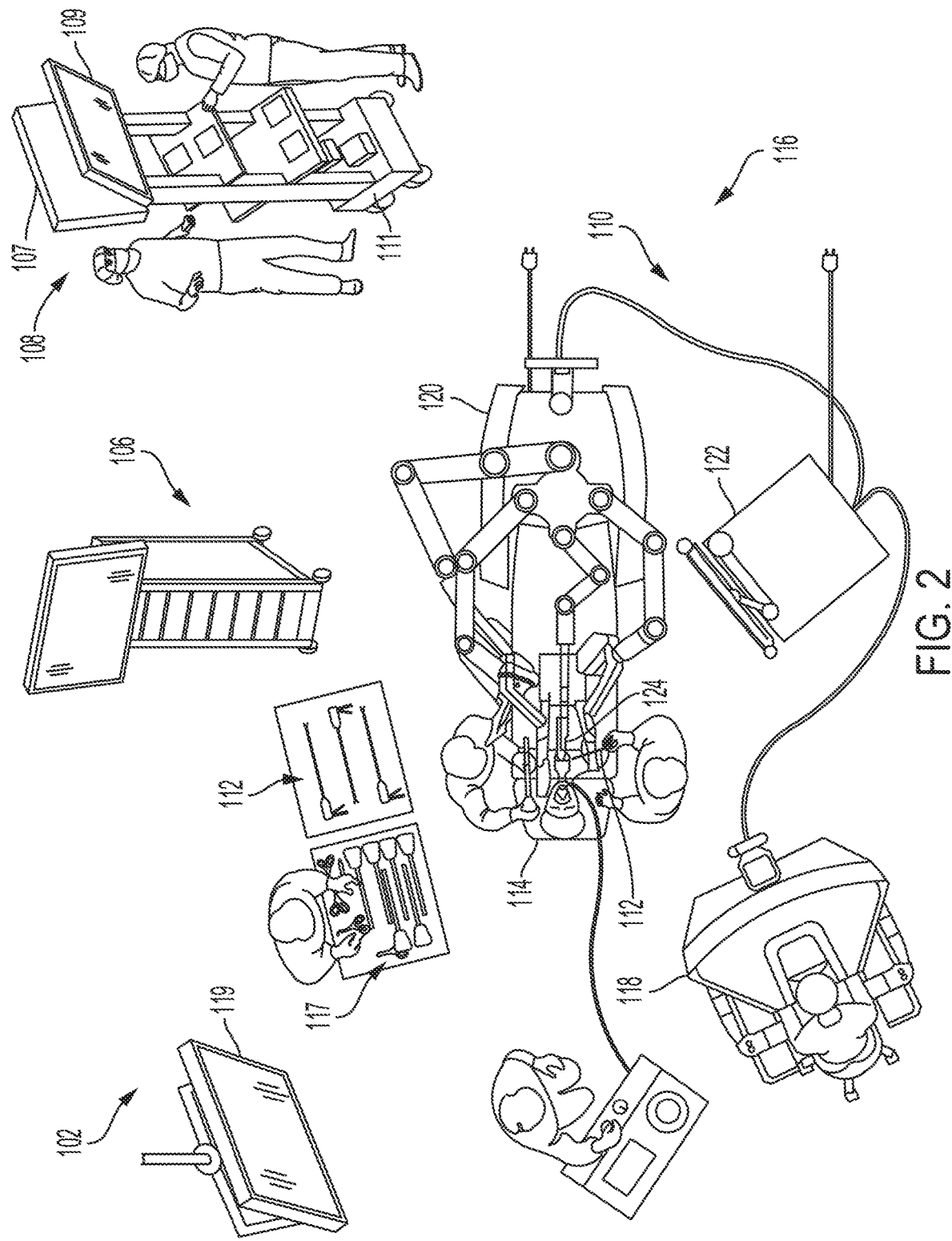
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading SURGICAL INSTRUMENT HARDWARE and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
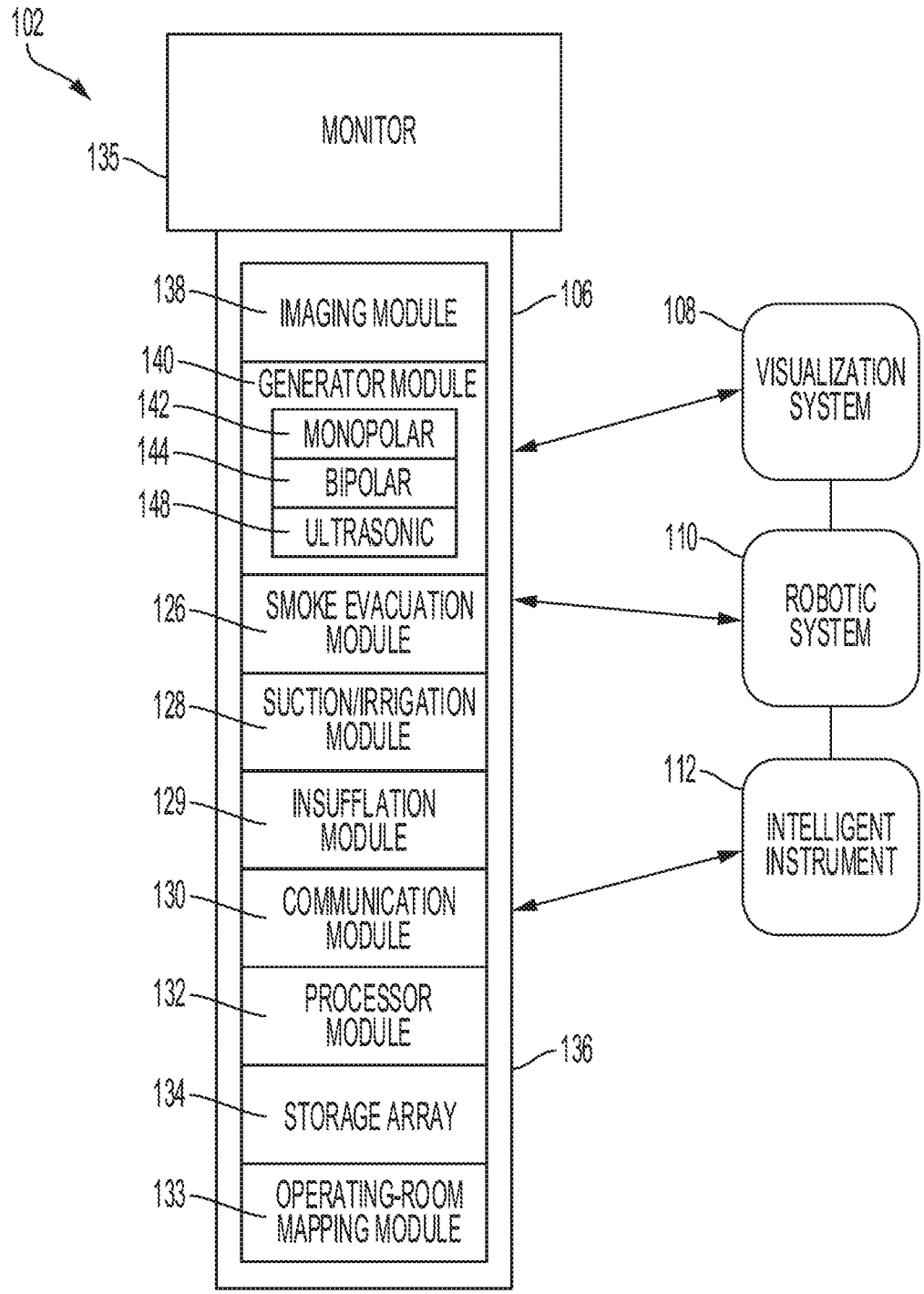
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. In some aspects, the visualization system 108 may be a separable piece of equipment. In alternative aspects, the visualization system 108 could be contained within the hub 106 as a functional module. The hub 106 includes a hub display 135, an imaging module 138, a generator module 140, a communication module 130, a processor module 132, a storage array 134, and an operating room mapping module 133. In certain aspects, as illustrated in FIG. 3, the hub 106 further includes a smoke evacuation module 126, a suction/irrigation module 128, and/or an insufflation module 129. In certain aspects, any of the modules in the hub 106 may be combined with each other into a single module.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes one or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts. In one aspect, the first energy-generator module is slidably movable into an electrical engagement with the power and data contacts and wherein the first energy-generator module is slidably movable out of the electrical engagement with the first power and data contacts. In an alternative aspect, the first energy-generator module is stackably movable into an electrical engagement with the power and data contacts and wherein the first energy-generator module is stackably movable out of the electrical engagement with the first power and data contacts.

Further to the above, the modular surgical enclosure also includes a second energy-generator module configured to generate a second energy, either the same or different than the first energy, for application to the tissue, and a second docking station comprising a second docking port that includes second data and power contacts. In one aspect, the second energy-generator module is slidably movable into an electrical engagement with the power and data contacts, and wherein the second energy-generator module is slidably movable out of the electrical engagement with the second power and data contacts. In an alternative aspect, the second energy-generator module is stackably movable into an electrical engagement with the power and data contacts, and wherein the second energy-generator module is stackably movable out of the electrical engagement with the second power and data contacts.

In addition, the modular surgical enclosure also includes a communication bus between the first docking port and the second docking port, configured to facilitate communication between the first energy-generator module and the second energy-generator module.

Referring to FIG. 3, aspects of the present disclosure are presented for a hub modular enclosure 136 that allows the modular integration of a generator module 140, a smoke evacuation module 126, a suction/irrigation module 128, and an insufflation module 129. The hub modular enclosure 136 further facilitates interactive communication between the modules 140, 126, 128, 129. The generator module 140 can be a generator module with integrated monopolar, bipolar, and ultrasonic components supported in a single housing unit slidably insertable into the hub modular enclosure 136. The generator module 140 can be configured to connect to a monopolar device 142, a bipolar device 144, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128, 129 and interactive communication therebetween.

Generator Hardware

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; a SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIG. 3, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 4:
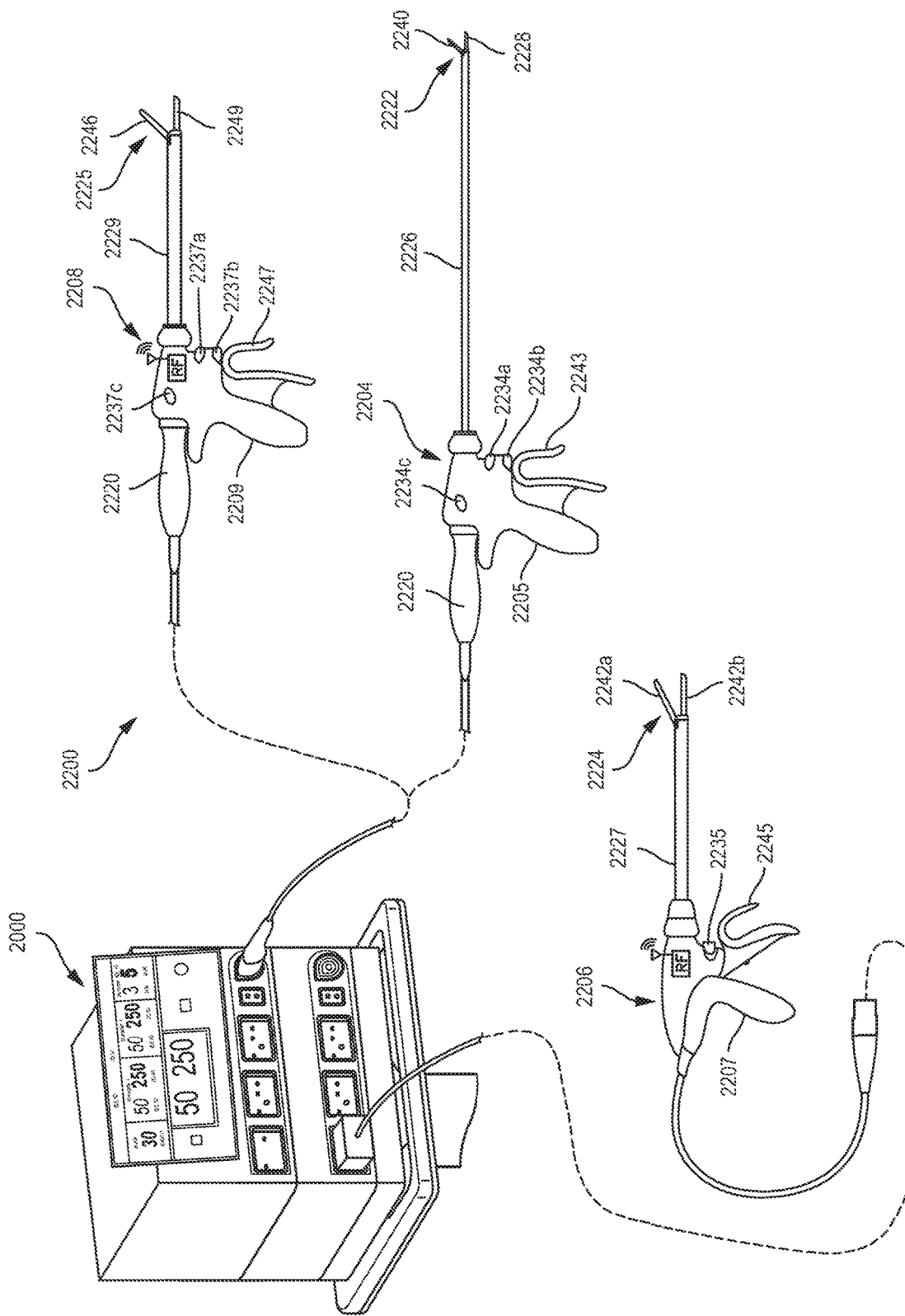
FIG. 4 is a surgical system comprising a generator and various surgical instruments usable therewith, in accordance with at least one aspect of the present disclosure.

FIG. 4 illustrates one form of a surgical system 2200 comprising a modular energy system 2000 and various surgical instruments 2204, 2206, 2208 usable therewith, where the surgical instrument 2204 is an ultrasonic surgical instrument, the surgical instrument 2206 is an RF electrosurgical instrument, and the multifunction surgical instrument 2208 is a combination ultrasonic/RF electrosurgical instrument. The modular energy system 2000 is configurable for use with a variety of surgical instruments. According to various forms, the modular energy system 2000 may be configurable for use with different surgical instruments of different types including, for example, ultrasonic surgical instruments 2204, RF electrosurgical instruments 2206, and multifunction surgical instruments 2208 that integrate RF and ultrasonic energies delivered individually or simultaneously from the modular energy system 2000. Although in the form of FIG. 4 the modular energy system 2000 is shown separate from the surgical instruments 2204, 2206, 2208 in one form, the modular energy system 2000 may be formed integrally with any of the surgical instruments 2204, 2206, 2208 to form a unitary surgical system. The modular energy system 2000 may be configured for wired or wireless communication.

The modular energy system 2000 is configured to drive multiple surgical instruments 2204, 2206, 2208. The first surgical instrument is an ultrasonic surgical instrument 2204 and comprises a handpiece 2205 (HP), an ultrasonic transducer 2220, a shaft 2226, and an end effector 2222. The end effector 2222 comprises an ultrasonic blade 2228 acoustically coupled to the ultrasonic transducer 2220 and a clamp arm 2240. The handpiece 2205 comprises a trigger 2243 to operate the clamp arm 2240 and a combination of the toggle buttons 2234a, 2234b, 2234c to energize and drive the ultrasonic blade 2228 or other function. The toggle buttons 2234a, 2234b, 2234c can be configured to energize the ultrasonic transducer 2220 with the modular energy system 2000.

The modular energy system 2000 also is configured to drive a second surgical instrument 2206. The second surgical instrument 2206 is an RF electrosurgical instrument and comprises a handpiece 2207 (HP), a shaft 2227, and an end effector 2224. The end effector 2224 comprises electrodes in clamp arms 2242a, 2242b and return through an electrical conductor portion of the shaft 2227. The electrodes are coupled to and energized by a bipolar energy source within the modular energy system 2000. The handpiece 2207 comprises a trigger 2245 to operate the clamp arms 2242a, 2242b and an energy button 2235 to actuate an energy switch to energize the electrodes in the end effector 2224.

The modular energy system 2000 also is configured to drive a multifunction surgical instrument 2208. The multifunction surgical instrument 2208 comprises a handpiece 2209 (HP), a shaft 2229, and an end effector 2225. The end effector 2225 comprises an ultrasonic blade 2249 and a clamp arm 2246. The ultrasonic blade 2249 is acoustically coupled to the ultrasonic transducer 2220. The ultrasonic transducer 2220 may be separable from or integral to the handpiece 2209. The handpiece 2209 comprises a trigger 2247 to operate the clamp arm 2246 and a combination of the toggle buttons 2237a, 2237b, 2237c to energize and drive the ultrasonic blade 2249 or other function. The toggle buttons 2237a, 2237b, 2237c can be configured to energize the ultrasonic transducer 2220 with the modular energy system 2000 and energize the ultrasonic blade 2249 with a bipolar energy source also contained within the modular energy system 2000.

The modular energy system 2000 is configurable for use with a variety of surgical instruments. According to various forms, the modular energy system 2000 may be configurable for use with different surgical instruments of different types including, for example, the ultrasonic surgical instrument 2204, the RF electrosurgical instrument 2206, and the multifunction surgical instrument 2208 that integrates RF and ultrasonic energies delivered individually or simultaneously from the modular energy system 2000. Although in the form of FIG. 4 the modular energy system 2000 is shown separate from the surgical instruments 2204, 2206, 2208, in another form the modular energy system 2000 may be formed integrally with any one of the surgical instruments 2204, 2206, 2208 to form a unitary surgical system. Further aspects of generators for digitally generating electrical signal waveforms and surgical instruments are described in US patent publication US-2017-0086914-A1, which is herein incorporated by reference in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or sub optimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 5:
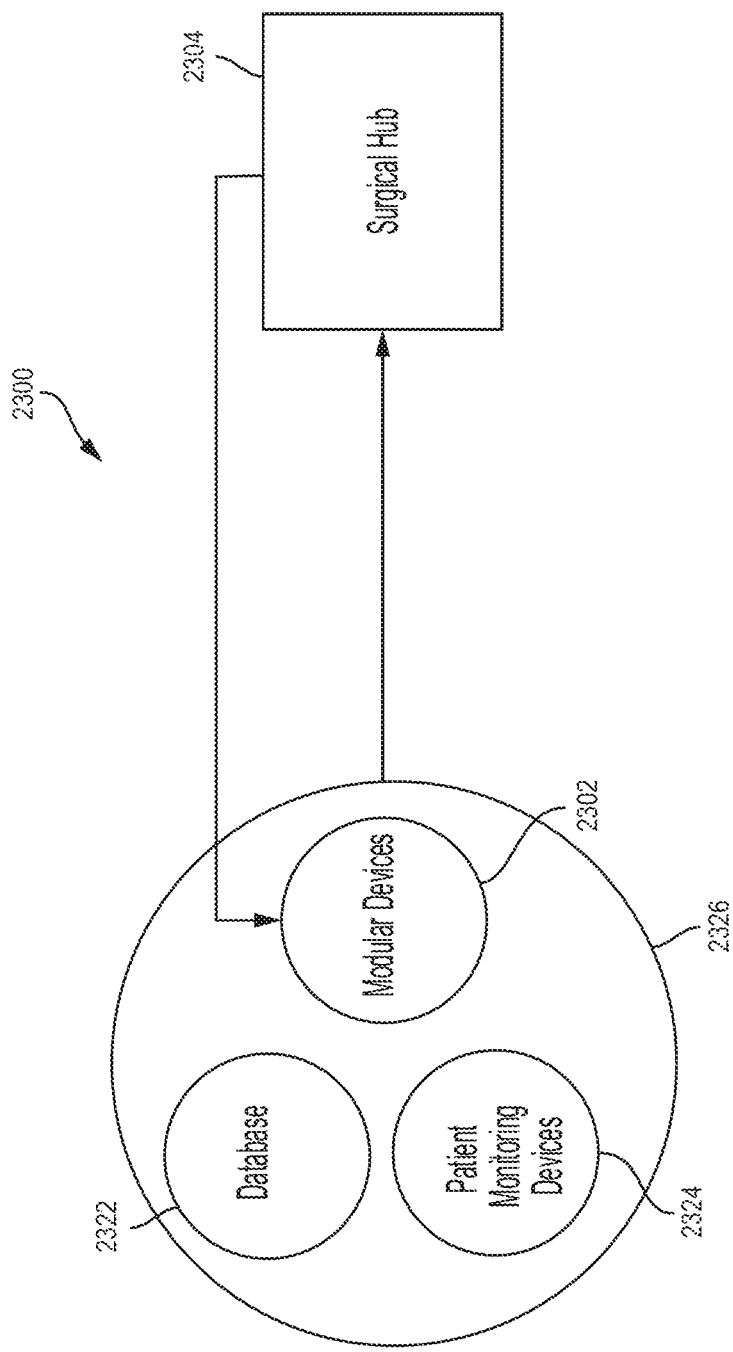
FIG. 5 is a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 5 illustrates a diagram of a situationally aware surgical system 2300, in accordance with at least one aspect of the present disclosure. In some exemplifications, the data sources 2326 include, for example, the modular devices 2302 (which can include sensors configured to detect parameters associated with the patient and/or the modular device itself), databases 2322 (e.g., an EMR database containing patient records), and patient monitoring devices 2324 (e.g., a blood pressure (BP) monitor and an electrocardiography (EKG) monitor). The surgical hub 2304 can be configured to derive the contextual information pertaining to the surgical procedure from the data based upon, for example, the particular combination(s) of received data or the particular order in which the data is received from the data sources 2326. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 2304 to derive or infer information related to the surgical procedure from received data can be referred to as "situational awareness." In one exemplification, the surgical hub 2304 can incorporate a situational awareness system, which is the hardware and/or programming associated with the surgical hub 2304 that derives contextual information pertaining to the surgical procedure from the received data.

The situational awareness system of the surgical hub 2304 can be configured to derive the contextual information from the data received from the data sources 2326 in a variety of different ways. In one exemplification, the situational awareness system includes a pattern recognition system, or machine learning system (e.g., an artificial neural network), that has been trained on training data to correlate various inputs (e.g., data from databases 2322, patient monitoring devices 2324, and/or modular devices 2302) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 2302. In one exemplification, the contextual information received by the situational awareness system of the surgical hub 2304 is associated with a particular control adjustment or set of control adjustments for one or more modular devices 2302. In another exemplification, the situational awareness system includes a further machine learning system, lookup table, or other such system, which generates or retrieves one or more control adjustments for one or more modular devices 2302 when provided the contextual information as input.

A surgical hub 2304 incorporating a situational awareness system provides a number of benefits for the surgical system 2300. One benefit includes improving the interpretation of sensed and collected data, which would in turn improve the processing accuracy and/or the usage of the data during the course of a surgical procedure. To return to a previous example, a situationally aware surgical hub 2304 could determine what type of tissue was being operated on; therefore, when an unexpectedly high force to close the surgical instrument's end effector is detected, the situationally aware surgical hub 2304 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 2304 could infer whether a surgical procedure being performed is a thoracic or an abdominal procedure, allowing the surgical hub 2304 to determine whether the tissue clamped by an end effector of the surgical stapling and cutting instrument is lung (for a thoracic procedure) or stomach (for an abdominal procedure) tissue. The surgical hub 2304 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 2304 could determine whether the surgical site is under pressure (by determining that the surgical procedure is utilizing insufflation) and determine the procedure type. As a procedure type is generally performed in a specific body cavity, the surgical hub 2304 could then control the motor rate of the smoke evacuator appropriately for the body cavity being operated in. Thus, a situationally aware surgical hub 2304 could provide a consistent amount of smoke evacuation for both thoracic and abdominal procedures.

As yet another example, the type of procedure being performed can affect the optimal energy level at which an ultrasonic surgical instrument or radio frequency (RF) electrosurgical instrument operates. Arthroscopic procedures, for example, require higher energy levels because the end effector of the ultrasonic surgical instrument or RF electrosurgical instrument is immersed in fluid. A situationally aware surgical hub 2304 could determine whether the surgical procedure is an arthroscopic procedure. The surgical hub 2304 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 2304 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 2304 can be configured to adjust the energy level for the ultrasonic surgical instrument or RF electrosurgical instrument throughout the course of a surgical procedure, rather than just on a procedure-by-procedure basis. A situationally aware surgical hub 2304 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 2326 to improve the conclusions that the surgical hub 2304 draws from one data source 2326. A situationally aware surgical hub 2304 could augment data that it receives from the modular devices 2302 with contextual information that it has built up regarding the surgical procedure from other data sources 2326. For example, a situationally aware surgical hub 2304 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 2304 can be further configured to compare a physiologic measurement (e.g., blood pressure sensed by a BP monitor communicably connected to the surgical hub 2304) with the visual or image data of hemostasis (e.g., from a medical imaging device 124 (FIG. 2) communicably coupled to the surgical hub 2304) to make a determination on the integrity of the staple line or tissue weld. In other words, the situational awareness system of the surgical hub 2304 can consider the physiological measurement data to provide additional context in analyzing the visualization data. The additional context can be useful when the visualization data may be inconclusive or incomplete on its own.

Another benefit includes proactively and automatically controlling the paired modular devices 2302 according to the particular step of the surgical procedure that is being performed to reduce the number of times that medical personnel are required to interact with or control the surgical system 2300 during the course of a surgical procedure. For example, a situationally aware surgical hub 2304 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 2304 could determine whether the current or subsequent step of the surgical procedure requires a different view or degree of magnification on the display according to the feature(s) at the surgical site that the surgeon is expected to need to view. The surgical hub 2304 could then proactively change the displayed view (supplied by, e.g., a medical imaging device for the visualization system 108) accordingly so that the display automatically adjusts throughout the surgical procedure.

As yet another example, a situationally aware surgical hub 2304 could determine which step of the surgical procedure is being performed or will subsequently be performed and whether particular data or comparisons between data will be required for that step of the surgical procedure. The surgical hub 2304 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 2304 could determine whether the operating theater is setup properly or optimally for the surgical procedure to be performed. The surgical hub 2304 can be configured to determine the type of surgical procedure being performed, retrieve the corresponding checklists, product location, or setup needs (e.g., from a memory), and then compare the current operating theater layout to the standard layout for the type of surgical procedure that the surgical hub 2304 determines is being performed. In one exemplification, the surgical hub 2304 can be configured to compare the list of items for the procedure (scanned by a scanner, for example) and/or a list of devices paired with the surgical hub 2304 to a recommended or anticipated manifest of items and/or devices for the given surgical procedure. If there are any discontinuities between the lists, the surgical hub 2304 can be configured to provide an alert indicating that a particular modular device 2302, patient monitoring device 2324, and/or other surgical item is missing. In one exemplification, the surgical hub 2304 can be configured to determine the relative distance or position of the modular devices 2302 and patient monitoring devices 2324 via proximity sensors, for example. The surgical hub 2304 can compare the relative positions of the devices to a recommended or anticipated layout for the particular surgical procedure. If there are any discontinuities between the layouts, the surgical hub 2304 can be configured to provide an alert indicating that the current layout for the surgical procedure deviates from the recommended layout.

As another example, a situationally aware surgical hub 2304 could determine whether the surgeon (or other medical personnel) was making an error or otherwise deviating from the expected course of action during the course of a surgical procedure. For example, the surgical hub 2304 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 2304 determined is being performed. In one exemplification, the surgical hub 2304 can be configured to provide an alert indicating that an unexpected action is being performed or an unexpected device is being utilized at the particular step in the surgical procedure.

Overall, the situational awareness system for the surgical hub 2304 improves surgical procedure outcomes by adjusting the surgical instruments (and other modular devices 2302) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 2302 in the surgical theater according to the specific context of the procedure.

Modular Energy System

ORs everywhere in the world are a tangled web of cords, devices, and people due to the amount of equipment required to perform surgical procedures. Surgical capital equipment tends to be a major contributor to this issue because most surgical capital equipment performs a single, specialized task. Due to their specialized nature and the surgeons' needs to utilize multiple different types of devices during the course of a single surgical procedure, an OR may be forced to be stocked with two or even more pieces of surgical capital equipment, such as energy generators. Each of these pieces of surgical capital equipment must be individually plugged into a power source and may be connected to one or more other devices that are being passed between OR personnel, creating a tangle of cords that must be navigated. Another issue faced in modern ORs is that each of these specialized pieces of surgical capital equipment has its own user interface and must be independently controlled from the other pieces of equipment within the OR. This creates complexity in properly controlling multiple different devices in connection with each other and forces users to be trained on and memorize different types of user interfaces (which may further change based upon the task or surgical procedure being performed, in addition to changing between each piece of capital equipment). This cumbersome, complex process can necessitate the need for even more individuals to be present within the OR and can create danger if multiple devices are not properly controlled in tandem with each other. Therefore, consolidating surgical capital equipment technology into singular systems that are able to flexibly address surgeons' needs to reduce the footprint of surgical capital equipment within ORs would simplify the user experience, reduce the amount of clutter in ORs, and prevent difficulties and dangers associated with simultaneously controlling multiple pieces of capital equipment. Further, making such systems expandable or customizable would allow for new technology to be conveniently incorporated into existing surgical systems, obviating the need to replace entire surgical systems or for OR personnel to learn new user interfaces or equipment controls with each new technology.

As described in FIGS. 1-3, a surgical hub 106 can be configured to interchangeably receive a variety of modules, which can in turn interface with surgical devices (e.g., a surgical instrument or a smoke evacuator) or provide various other functions (e.g., communications). In one aspect, a surgical hub 106 can be embodied as a modular energy system 2000, which is illustrated in connection with FIGS. 6-12. The modular energy system 2000 can include a variety of different modules 2001 that are connectable together in a stacked configuration. In one aspect, the modules 2001 can be both physically and communicably coupled together when stacked or otherwise connected together into a singular assembly. Further, the modules 2001 can be interchangeably connectable together in different combinations or arrangements. In one aspect, each of the modules 2001 can include a consistent or universal array of connectors disposed along their upper and lower surfaces, thereby allowing any module 2001 to be connected to another module 2001 in any arrangement (except that, in some aspects, a particular module type, such as the header module 2002, can be configured to serve as the uppermost module within the stack, for example). In an alternative aspect, the modular energy system 2000 can include a housing that is configured to receive and retain the modules 2001, as is shown in FIG. 3. The modular energy system 2000 can also include a variety of different components or accessories that are also connectable to or otherwise associatable with the modules 2001. In another aspect, the modular energy system 2000 can be embodied as a generator module 140 (FIG. 3) of a surgical hub 106. In yet another aspect, the modular energy system 2000 can be a distinct system from a surgical hub 106. In such aspects, the modular energy system 2000 can be communicably couplable to a surgical hub 206 for transmitting and/or receiving data therebetween.

Figure 6:
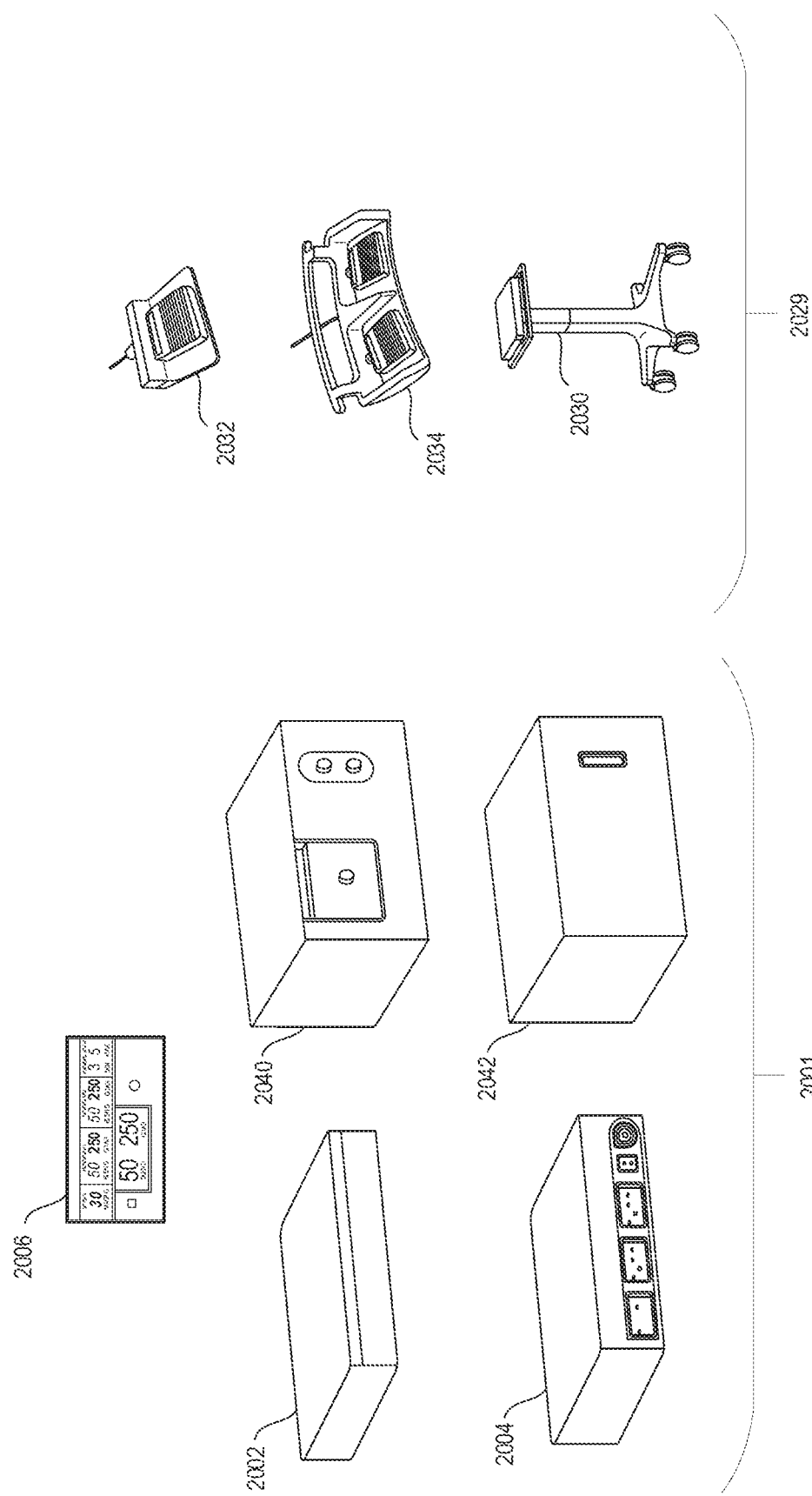
FIG. 6 is a diagram of various modules and other components that are combinable to customize modular energy systems, in accordance with at least one aspect of the present disclosure.

The modular energy system 2000 can be assembled from a variety of different modules 2001, some examples of which are illustrated in FIG. 6. Each of the different types of modules 2001 can provide different functionality, thereby allowing the modular energy system 2000 to be assembled into different configurations to customize the functions and capabilities of the modular energy system 2000 by customizing the modules 2001 that are included in each modular energy system 2000. The modules 2001 of the modular energy system 2000 can include, for example, a header module 2002 (which can include a display screen 2006), an energy module 2004, a technology module 2040, and a visualization module 2042. In the depicted aspect, the header module 2002 is configured to serve as the top or uppermost module within the modular energy system stack and can thus lack connectors along its top surface. In another aspect, the header module 2002 can be configured to be positioned at the bottom or the lowermost module within the modular energy system stack and can thus lack connectors along its bottom surface. In yet another aspect, the header module 2002 can be configured to be positioned at an intermediate position within the modular energy system stack and can thus include connectors along both its bottom and top surfaces. The header module 2002 can be configured to control the system-wide settings of each module 2001 and component connected thereto through physical controls 2011 thereon and/or a graphical user interface (GUI) 2008 rendered on the display screen 2006. Such settings could include the activation of the modular energy system 2000, the volume of alerts, the footswitch settings, the settings icons, the appearance or configuration of the user interface, the surgeon profile logged into the modular energy system 2000, and/or the type of surgical procedure being performed. The header module 2002 can also be configured to provide communications, processing, and/or power for the modules 2001 that are connected to the header module 2002. The energy module 2004, which can also be referred to as a generator module 140 (FIG. 3), can be configured to generate one or multiple energy modalities for driving electrosurgical and/or ultrasonic surgical instruments connected thereto. The technology module 2040 can be configured to provide additional or expanded control algorithms (e.g., electrosurgical or ultrasonic control algorithms for controlling the energy output of the energy module 2004). The visualization module 2042 can be configured to interface with visualization devices (i.e., scopes) and accordingly provide increased visualization capabilities.

The modular energy system 2000 can further include a variety of accessories 2029 that are connectable to the modules 2001 for controlling the functions thereof or that are otherwise configured to work on conjunction with the modular energy system 2000. The accessories 2029 can include, for example, a single-pedal footswitch 2032, a dual-pedal footswitch 2034, and a cart 2030 for supporting the modular energy system 2000 thereon. The footswitches 2032, 2034 can be configured to control the activation or function of particular energy modalities output by the energy module 2004, for example.

By utilizing modular components, the depicted modular energy system 2000 provides a surgical platform that grows with the availability of technology and is customizable to the needs of the facility and/or surgeons. Further, the modular energy system 2000 supports combo devices (e.g., dual electrosurgical and ultrasonic energy generators) and supports software-driven algorithms for customized tissue effects. Still further, the surgical system architecture reduces the capital footprint by combining multiple technologies critical for surgery into a single system.

The various modular components utilizable in connection with the modular energy system 2000 can include monopolar energy generators, bipolar energy generators, dual electrosurgical/ultrasonic energy generators, display screens, and various other modules and/or other components, some of which are also described above in connection with FIGS. 1-3.

Figure 11:
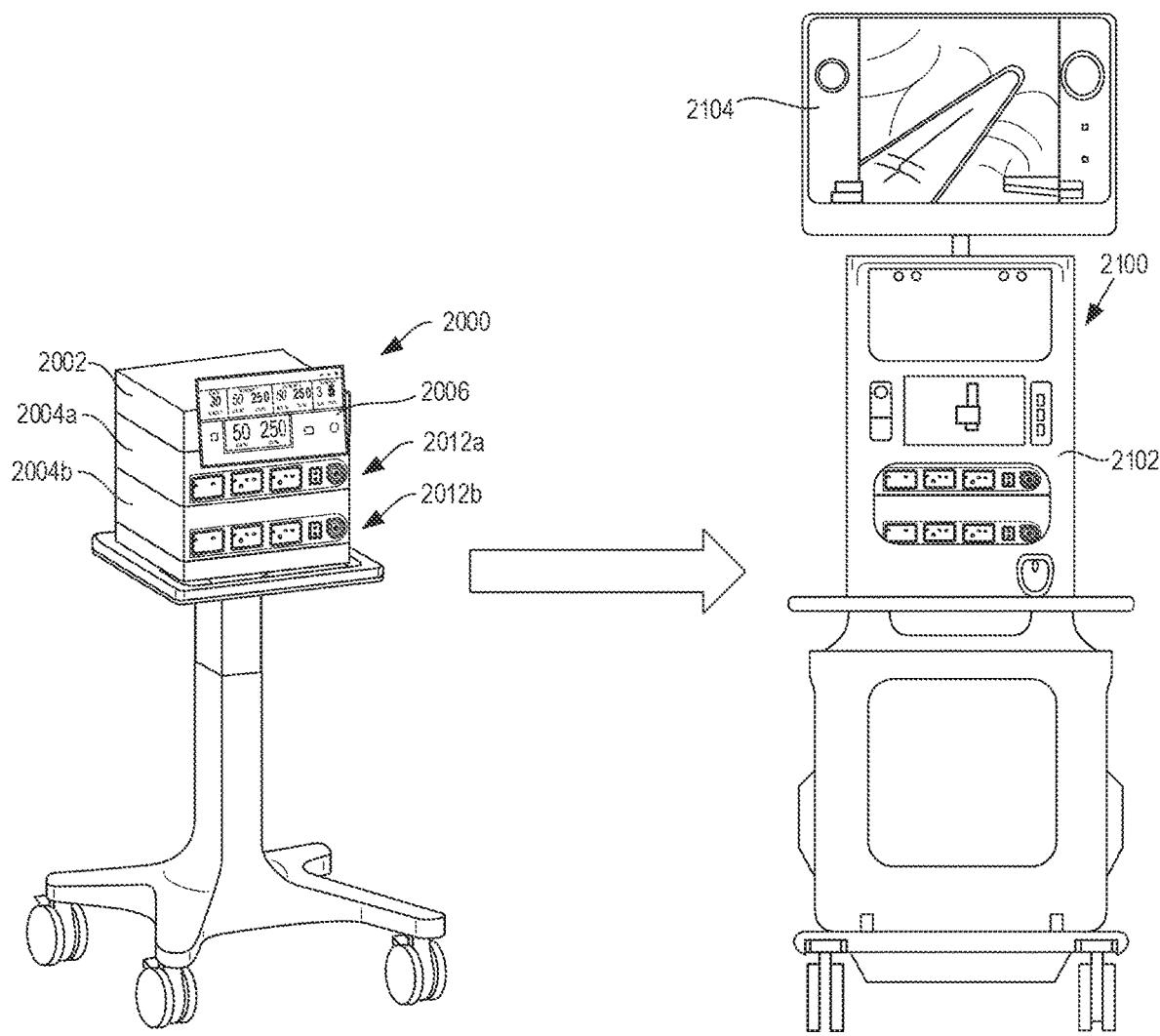
FIG. 11 is a diagram of a modular energy system including communicably connectable surgical platforms, in accordance with at least one aspect of the present disclosure.

Referring now to FIG. 7A, the header module 2002 can, in some aspects, include a display screen 2006 that renders a GUI 2008 for relaying information regarding the modules 2001 connected to the header module 2002. In some aspects, the GUI 2008 of the display screen 2006 can provide a consolidated point of control of all of the modules 2001 making up the particular configuration of the modular energy system 2000. Various aspects of the GUI 2008 are discussed in fuller detail below in connection with FIG. 12. In alternative aspects, the header module 2002 can lack the display screen 2006 or the display screen 2006 can be detachably connected to the housing 2010 of the header module 2002. In such aspects, the header module 2002 can be communicably couplable to an external system that is configured to display the information generated by the modules 2001 of the modular energy system 2000. For example, in robotic surgical applications, the modular energy system 2000 can be communicably couplable to a robotic cart or robotic control console, which is configured to display the information generated by the modular energy system 2000 to the operator of the robotic surgical system. As another example, the modular energy system 2000 can be communicably couplable to a mobile display that can be carried or secured to a surgical staff member for viewing thereby. In yet another example, the modular energy system 2000 can be communicably couplable to a surgical hub 2100 or another computer system that can include a display 2104, as is illustrated in FIG. 11. In aspects utilizing a user interface that is separate from or otherwise distinct from the modular energy system 2000, the user interface can be wirelessly connectable with the modular energy system 2000 as a whole or one or more modules 2001 thereof such that the user interface can display information from the connected modules 2001 thereon.

Referring still to FIG. 7A, the energy module 2004 can include a port assembly 2012 including a number of different ports configured to deliver different energy modalities to corresponding surgical instruments that are connectable thereto. In the particular aspect illustrated in FIGS. 6-12, the port assembly 2012 includes a bipolar port 2014, a first monopolar port 2016a, a second monopolar port 2016b, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012.

As noted above, the modular energy system 2000 can be assembled into different configurations. Further, the different configurations of the modular energy system 2000 can also be utilizable for different surgical procedure types and/or different tasks. For example, FIGS. 7A and 7B illustrate a first illustrative configuration of the modular energy system 2000 including a header module 2002 (including a display screen 2006) and an energy module 2004 connected together. Such a configuration can be suitable for laparoscopic and open surgical procedures, for example.

Figure 8A:
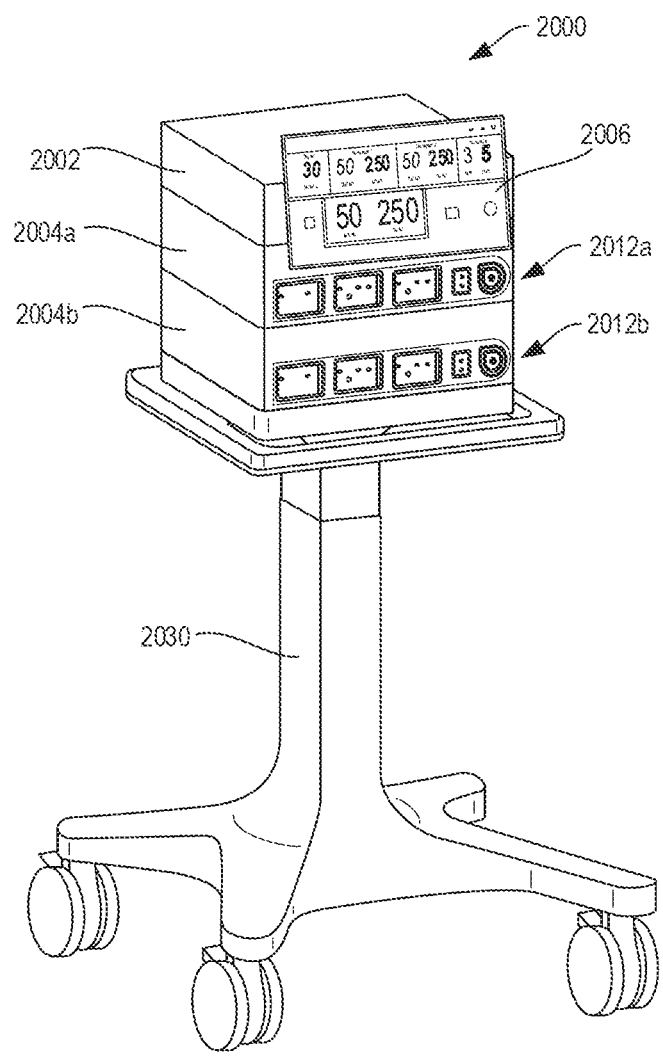
FIG. 8A is a second illustrative modular energy system configuration including a header module, a display screen, an energy module, and an expanded energy module connected together and mounted to a cart, in accordance with at least one aspect of the present disclosure.
Figure 8B:
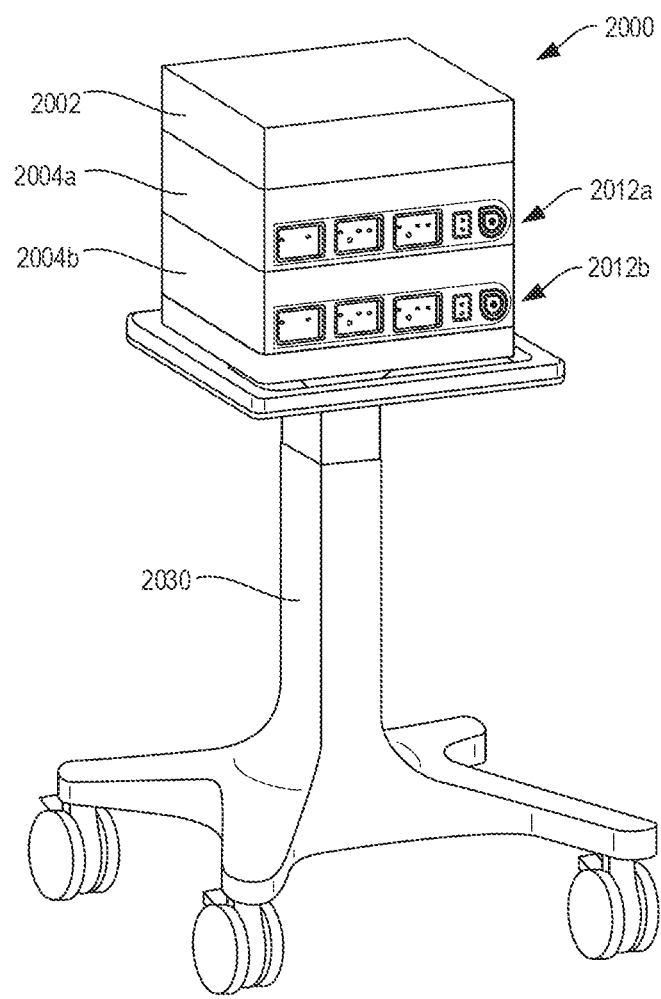
FIG. 8B is a third illustrative modular energy system configuration that is similar to the second configuration shown in FIG. 7A, except that the header module lacks a display screen, in accordance with at least one aspect of the present disclosure.

FIG. 8A illustrates a second illustrative configuration of the modular energy system 2000 including a header module 2002 (including a display screen 2006), a first energy module 2004a, and a second energy module 2004b connected together. By stacking two energy modules 2004a, 2004b, the modular energy system 2000 can provide a pair of port assemblies 2012a, 2012b for expanding the array of energy modalities deliverable by the modular energy system 2000 from the first configuration. The second configuration of the modular energy system 2000 can accordingly accommodate more than one bipolar/monopolar electrosurgical instrument, more than two bipolar/monopolar electrosurgical instruments, and so on. Such a configuration can be suitable for particularly complex laparoscopic and open surgical procedures. FIG. 8B illustrates a third illustrative configuration that is similar to the second configuration, except that the header module 2002 lacks a display screen 2006. This configuration can be suitable for robotic surgical applications or mobile display applications, as noted above.

Figure 9:
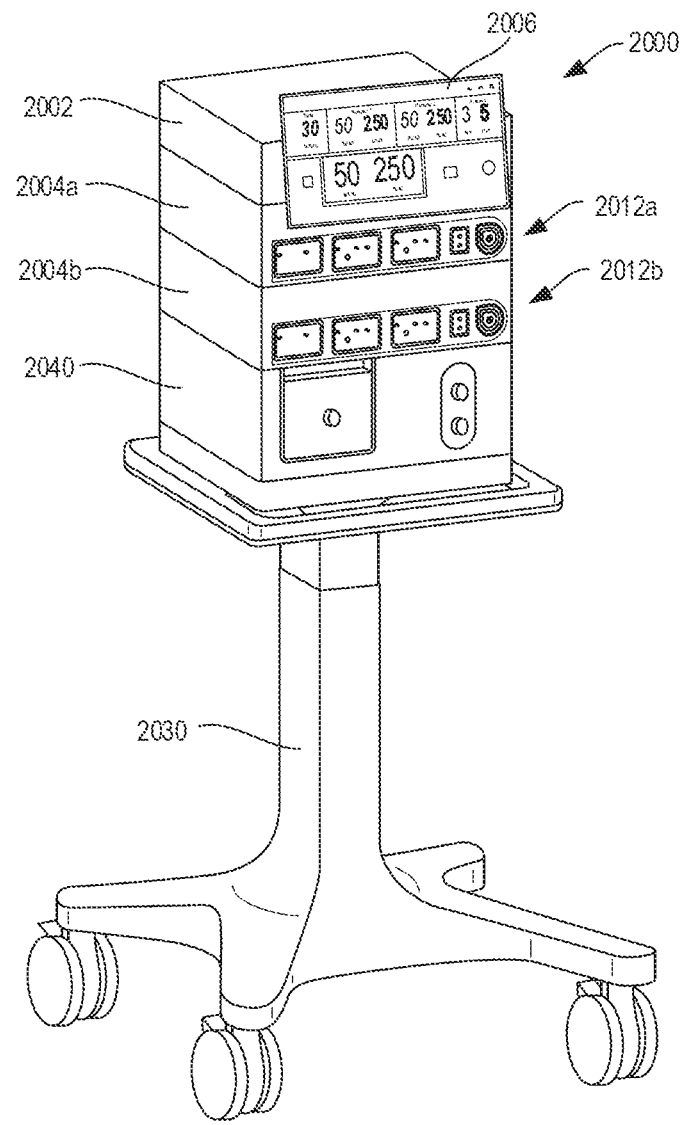
FIG. 9 is a fourth illustrative modular energy system configuration including a header module, a display screen, an energy module, ae expanded energy module, and a technology module connected together and mounted to a cart, in accordance with at least one aspect of the present disclosure.

FIG. 9 illustrates a fourth illustrative configuration of the modular energy system 2000 including a header module 2002 (including a display screen 2006), a first energy module 2004a, a second energy module 2004b, and a technology module 2040 connected together. Such a configuration can be suitable for surgical applications where particularly complex or computation-intensive control algorithms are required. Alternatively, the technology module 2040 can be a newly released module that supplements or expands the capabilities of previously released modules (such as the energy module 2004).

Figure 10:
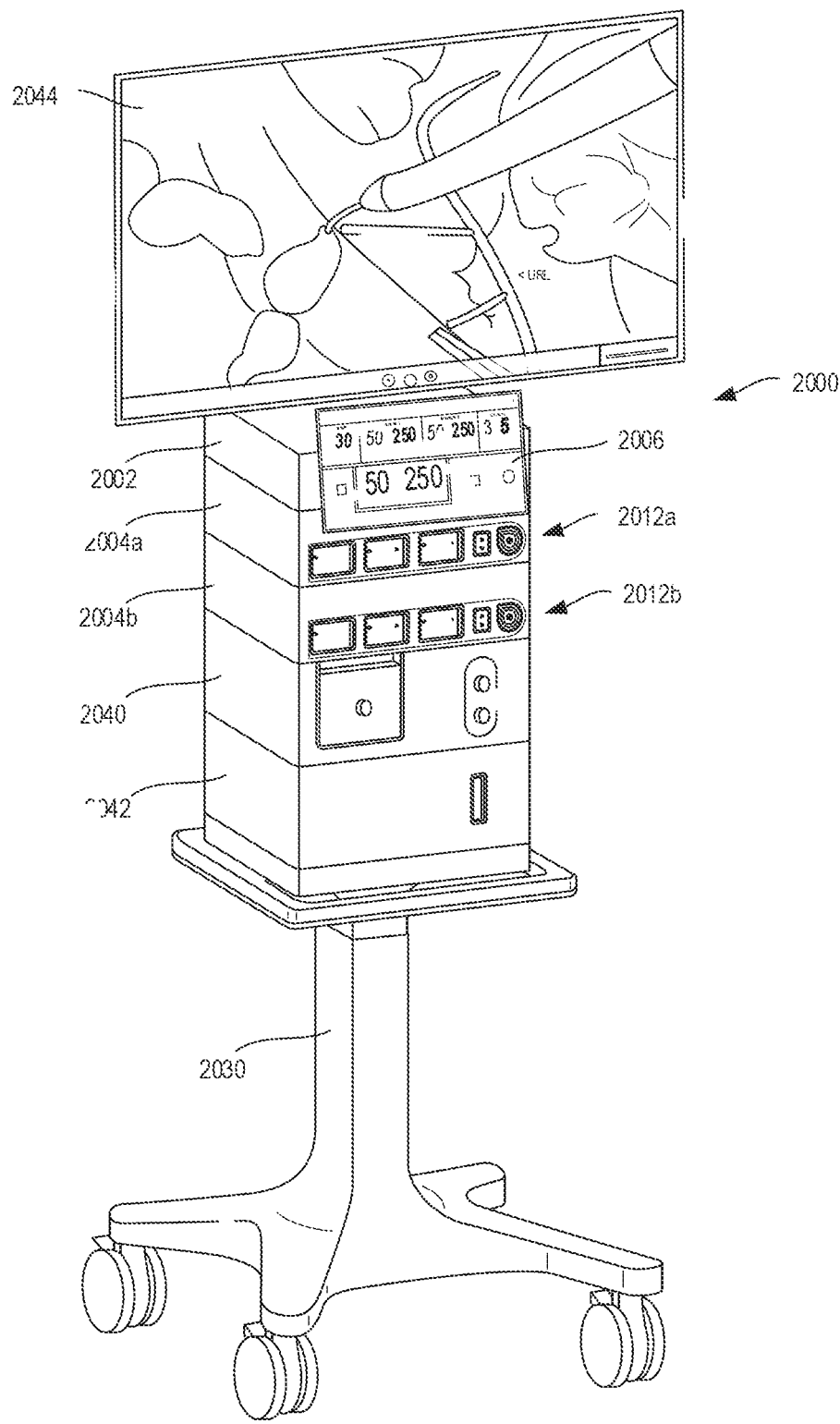
FIG. 10 is a fifth illustrative modular energy system configuration including a header module, a display screen, an energy module, an expanded energy module, a technology module, and a visualization module connected together and mounted to a cart, in accordance with at least one aspect of the present disclosure.

FIG. 10 illustrates a fifth illustrative configuration of the modular energy system 2000 including a header module 2002 (including a display screen 2006), a first energy module 2004a, a second energy module 2004b, a technology module 2040, and a visualization module 2042 connected together. Such a configuration can be suitable for endoscopic procedures by providing a dedicated surgical display 2044 for relaying the video feed from the scope coupled to the visualization module 2042. It should be noted that the configurations illustrated in FIGS. 7A-11 and described above are provided simply to illustrate the various concepts of the modular energy system 2000 and should not be interpreted to limit the modular energy system 2000 to the particular aforementioned configurations.

As noted above, the modular energy system 2000 can be communicably couplable to an external system, such as a surgical hub 2100 as illustrated in FIG. 11. Such external systems can include a display screen 2104 for displaying a visual feed from an endoscope (or a camera or another such visualization device) and/or data from the modular energy system 2000. Such external systems can also include a computer system 2102 for performing calculations or otherwise analyzing data generated or provided by the modular energy system 2000, controlling the functions or modes of the modular energy system 2000, and/or relaying data to a cloud computing system or another computer system. Such external systems could also coordinate actions between multiple modular energy systems 2000 and/or other surgical systems (e.g., a visualization system 108 and/or a robotic system 110 as described in connection with FIGS. 1 and 2).

Figure 12:
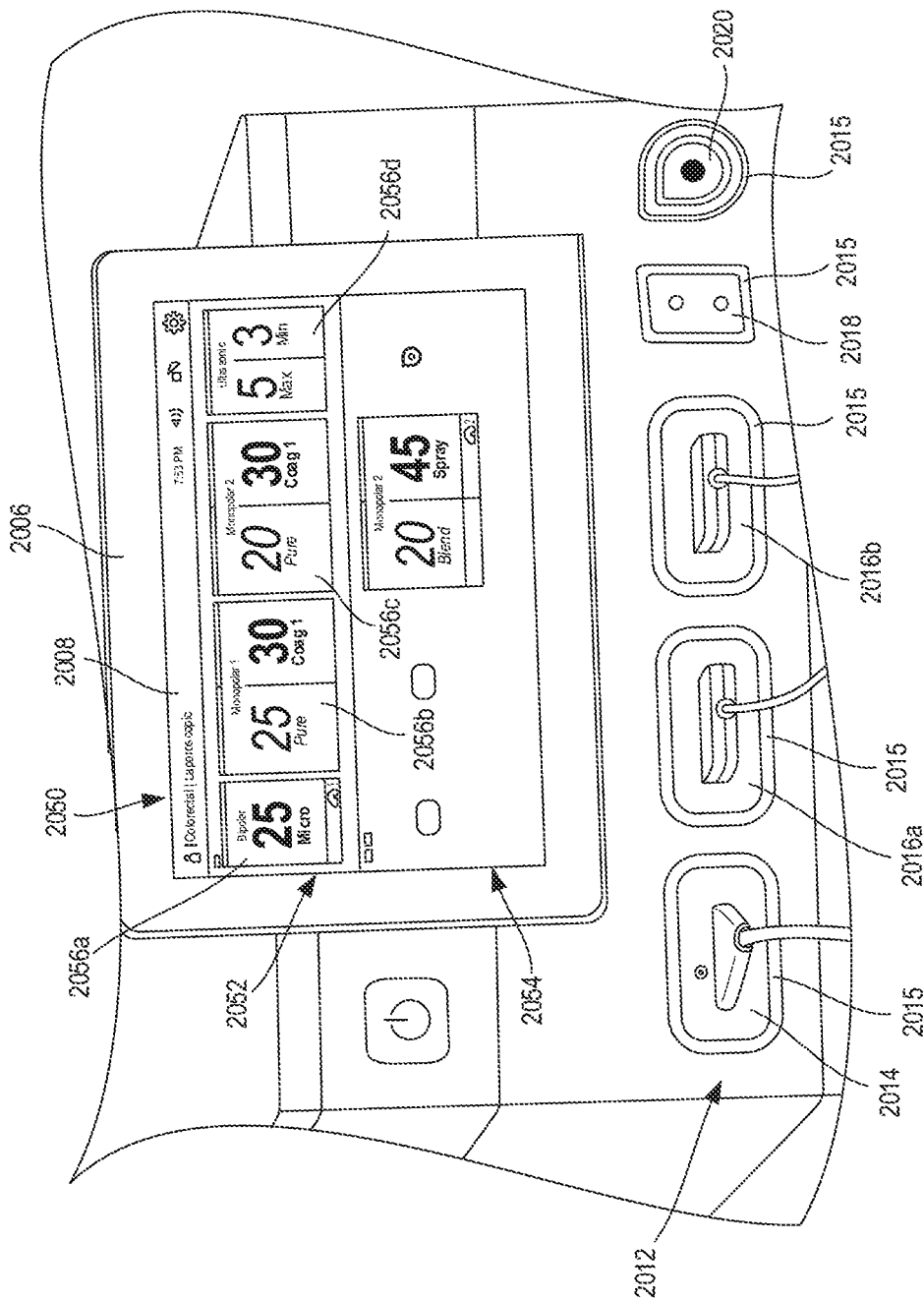
FIG. 12 is a perspective view of a header module of a modular energy system including a user interface, in accordance with at least one aspect of the present disclosure.

Referring now to FIG. 12, in some aspects, the header module 2002 can include or support a display 2006 configured for displaying a GUI 2008, as noted above. The display screen 2006 can include a touchscreen for receiving input from users in addition to displaying information. The controls displayed on the GUI 2008 can correspond to the module(s) 2001 that are connected to the header module 2002. In some aspects, different portions or areas of the GUI 2008 can correspond to particular modules 2001. For example, a first portion or area of the GUI 2008 can correspond to a first module and a second portion or area of the GUI 2008 can correspond to a second module. As different and/or additional modules 2001 are connected to the modular energy system stack, the GUI 2008 can adjust to accommodate the different and/or additional controls for each newly added module 2001 or remove controls for each module 2001 that is removed. Each portion of the display corresponding to a particular module connected to the header module 2002 can display controls, data, user prompts, and/or other information corresponding to that module. For example, in FIG. 12, a first or upper portion 2052 of the depicted GUI 2008 displays controls and data associated with an energy module 2004 that is connected to the header module 2002. In particular, the first portion 2052 of the GUI 2008 for the energy module 2004 provides first widget 2056a corresponding to the bipolar port 2014, a second widget 2056b corresponding to the first monopolar port 2016a, a third widget 2056c corresponding to the second monopolar port 2016b, and a fourth widget 2056d corresponding to the combination energy port 2020. Each of these widgets 2056a-d provides data related to its corresponding port of the port assembly 2012 and controls for controlling the modes and other features of the energy modality delivered by the energy module 2004 through the respective port of the port assembly 2012. For example, the widgets 2056a-d can be configured to display the power level of the surgical instrument connected to the respective port, change the operational mode of the surgical instrument connected to the respective port (e.g., change a surgical instrument from a first power level to a second power level and/or change a monopolar surgical instrument from a "spray" mode to a "blend" mode), and so on.

In one aspect, the header module 2002 can include various physical controls 2011 in addition to or in lieu of the GUI 2008. Such physical controls 2011 can include, for example, a power button that controls the application of power to each module 2001 that is connected to the header module 2002 in the modular energy system 2000. Alternatively, the power button can be displayed as part of the GUI 2008. Therefore, the header module 2002 can serve as a single point of contact and obviate the need to individually activate and deactivate each individual module 2001 from which the modular energy system 2000 is constructed.

In one aspect, the header module 2002 can display still images, videos, animations, and/or information associated with the surgical modules 2001 of which the modular energy system 2000 is constructed or the surgical devices that are communicably coupled to the modular energy system 2000. The still images and/or videos displayed by the header module 2002 can be received from an endoscope or another visualization device that is communicably coupled to the modular energy system 2000. The animations and/or information of the GUI 2008 can be overlaid on or displayed adjacent to the images or video feed.

In one aspect, the modules 2001 other than the header module 2002 can be configured to likewise relay information to users. For example, the energy module 2004 can include light assemblies 2015 disposed about each of the ports of the port assembly 2012. The light assemblies 2015 can be configured to relay information to the user regarding the port according to their color or state (e.g., flashing). For example, the light assemblies 2015 can change from a first color to a second color when a plug is fully seated within the respective port. In one aspect, the color or state of the light assemblies 2015 can be controlled by the header module 2002. For example, the header module 2002 can cause the light assembly 2015 of each port to display a color corresponding to the color display for the port on the GUI 2008.

Figure 13:
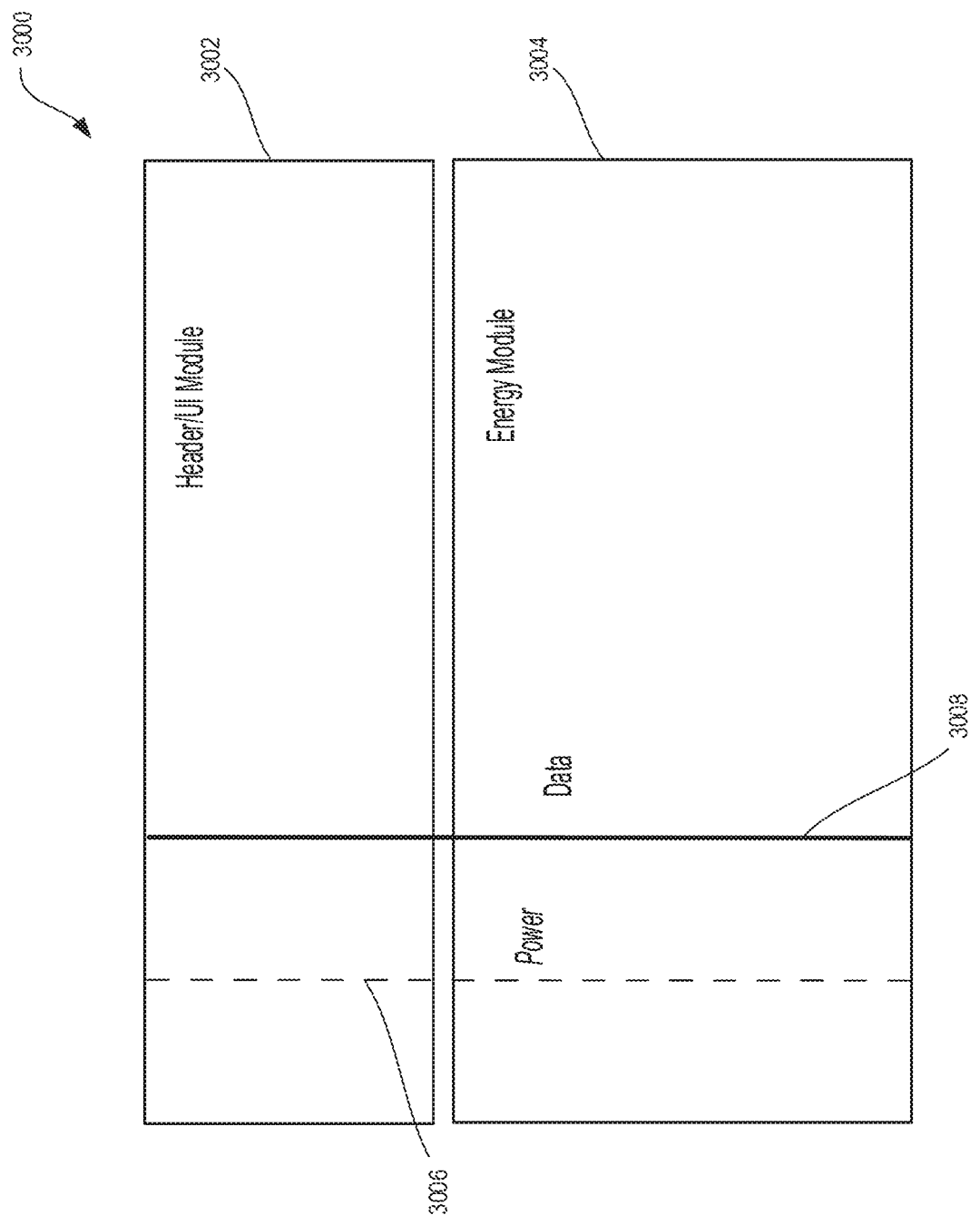
FIG. 13 is a block diagram of a stand-alone hub configuration of a modular energy system, in accordance with at least one aspect of the present disclosure.
Figure 14:
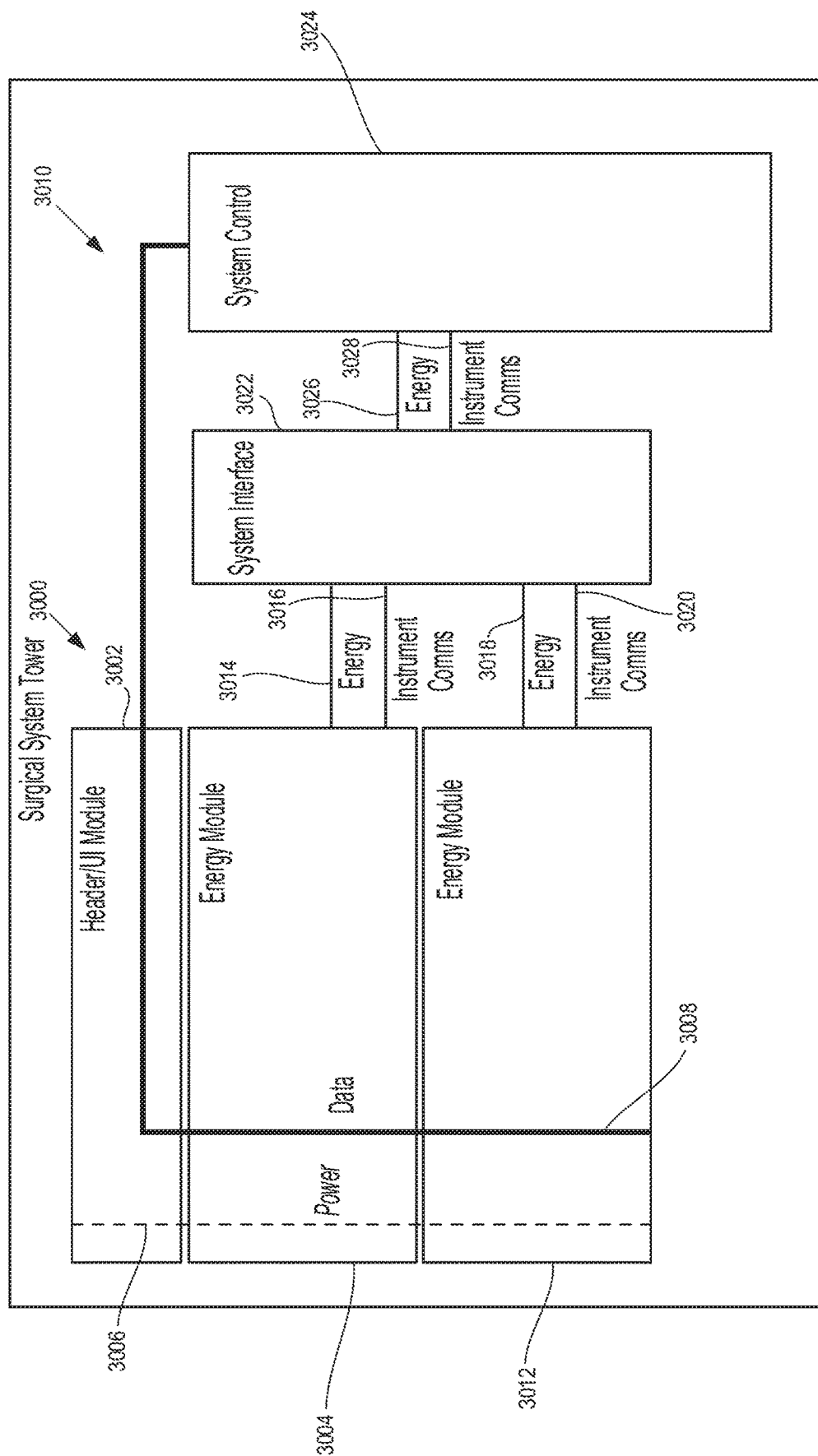
FIG. 14 is a block diagram of a hub configuration of a modular energy system integrated with a surgical control system, in accordance with at least one aspect of the present disclosure.

FIG. 13 is a block diagram of a stand-alone hub configuration of a modular energy system 3000, in accordance with at least one aspect of the present disclosure and FIG. 14 is a block diagram of a hub configuration of a modular energy system 3000 integrated with a surgical control system 3010, in accordance with at least one aspect of the present disclosure. As depicted in FIGS. 13 and 14, the modular energy system 3000 can be either utilized as stand-alone units or integrated with a surgical control system 3010 that controls and/or receives data from one or more surgical hub units. In the examples illustrated in FIGS. 13 and 14, the integrated header/UI module 3002 of the modular energy system 3000 includes a header module and a UI module integrated together as a singular module. In other aspects, the header module and the UI module can be provided as separate components that are communicatively coupled though a data bus 3008.

As illustrated in FIG. 13, an example of a stand-alone modular energy system 3000 includes an integrated header module/user interface (UI) module 3002 coupled to an energy module 3004. Power and data are transmitted between the integrated header/UI module 3002 and the energy module 3004 through a power interface 3006 and a data interface 3008. For example, the integrated header/UI module 3002 can transmit various commands to the energy module 3004 through the data interface 3008. Such commands can be based on user inputs from the UI. As a further example, power may be transmitted to the energy module 3004 through the power interface 3006.

In FIG. 14, a surgical hub configuration includes a modular energy system 3000 integrated with a control system 3010 and an interface system 3022 for managing, among other things, data and power transmission to and/or from the modular energy system 3000. The modular energy system depicted in FIG. 14 includes an integrated header module/UI module 3002, a first energy module 3004, and a second energy module 3012. In one example, a data transmission pathway is established between the system control unit 3024 of the control system 3010 and the second energy module 3012 through the first energy module 3004 and the header/UI module 3002 through a data interface 3008. In addition, a power pathway extends between the integrated header/UI module 3002 and the second energy module 3012 through the first energy module 3004 through a power interface 3006. In other words, in one aspect, the first energy module 3004 is configured to function as a power and data interface between the second energy module 3012 and the integrated header/UI module 3002 through the power interface 3006 and the data interface 3008. This arrangement allows the modular energy system 3000 to expand by seamlessly connecting additional energy modules to energy modules 3004, 3012 that are already connected to the integrated header/UI module 3002 without the need for dedicated power and energy interfaces within the integrated header/UI module 3002.

The system control unit 3024, which may be referred to herein as a control circuit, control logic, microprocessor, microcontroller, logic, or FPGA, or various combinations thereof, is coupled to the system interface 3022 via energy interface 3026 and instrument communication interface 3028. The system interface 3022 is coupled to the first energy module 3004 via a first energy interface 3014 and a first instrument communication interface 3016. The system interface 3022 is coupled to the second energy module 3012 via a second energy interface 3018 and a second instrument communication interface 3020. As additional modules, such as additional energy modules, are stacked in the modular energy system 3000, additional energy and communications interfaces are provided between the system interface 3022 and the additional modules.

The energy modules 3004, 3012 are connectable to a hub and can be configured to generate electrosurgical energy (e.g., bipolar or monopolar), ultrasonic energy, or a combination thereof (referred to herein as an "advanced energy" module) for a variety of energy surgical instruments. Generally, the energy modules 3004, 3012 include hardware/software interfaces, an ultrasonic controller, an advanced energy RF controller, bipolar RF controller, and control algorithms executed by the controller that receives outputs from the controller and controls the operation of the various energy modules 3004, 3012 accordingly. In various aspects of the present disclosure, the controllers described herein may be implemented as a control circuit, control logic, microprocessor, microcontroller, logic, or FPGA, or various combinations thereof.

Figure 15:
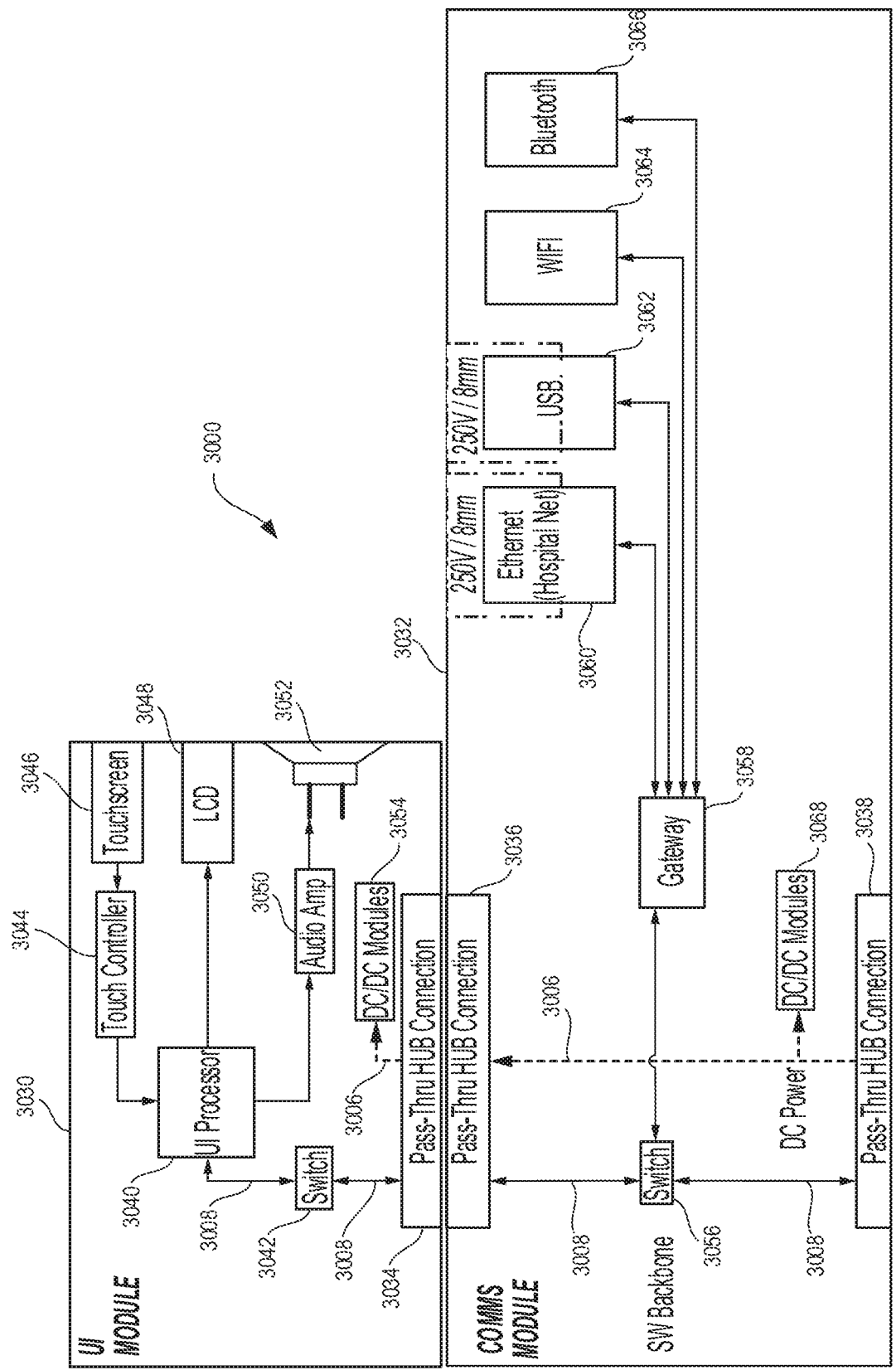
FIG. 15 is a block diagram of a user interface module coupled to a communications module of a modular energy system, in accordance with at least one aspect of the present disclosure.
Figure 16:
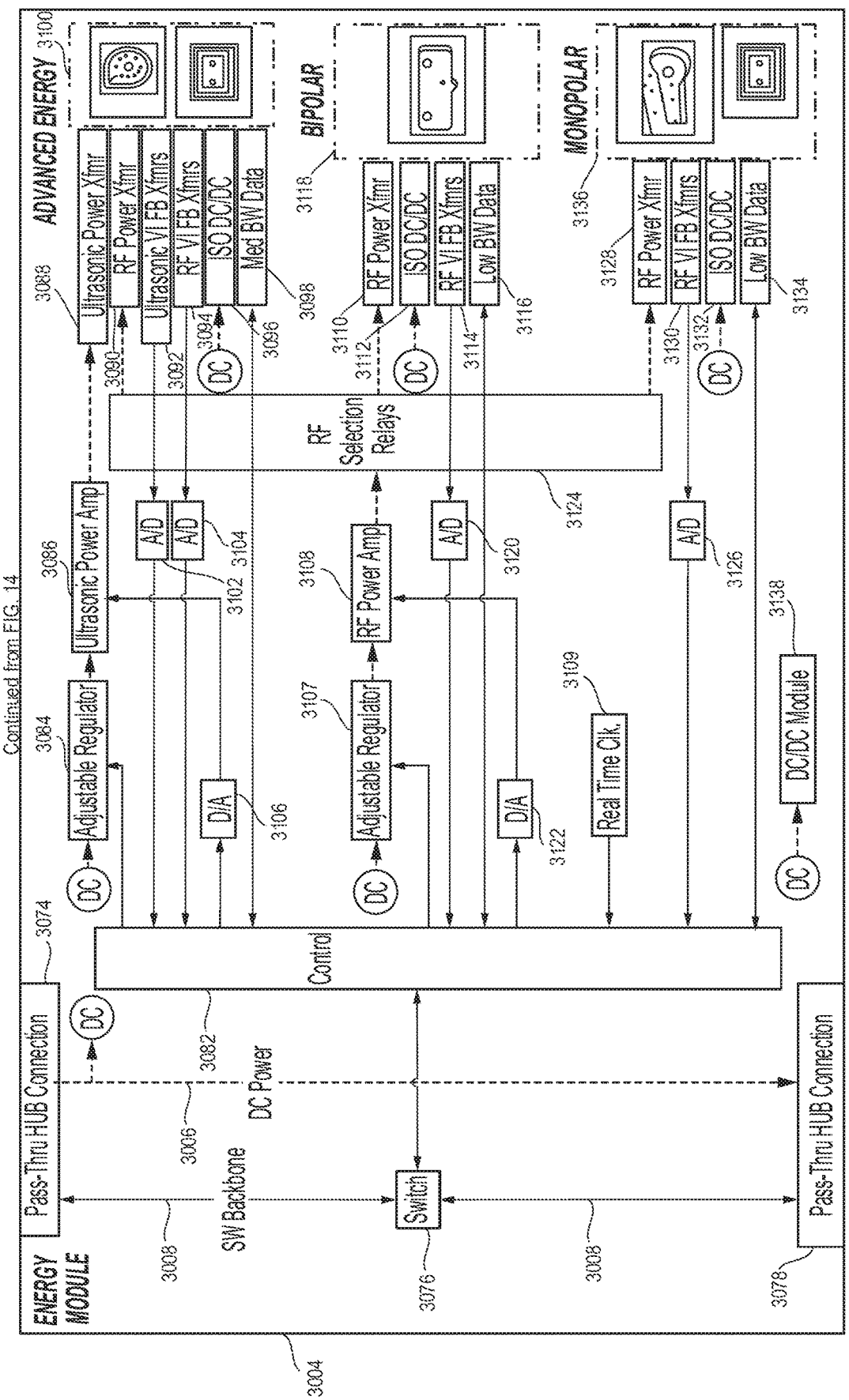
FIG. 16 is a block diagram of an energy module of a modular energy system, in accordance with at least one aspect of the present disclosure.
Figure 17A:
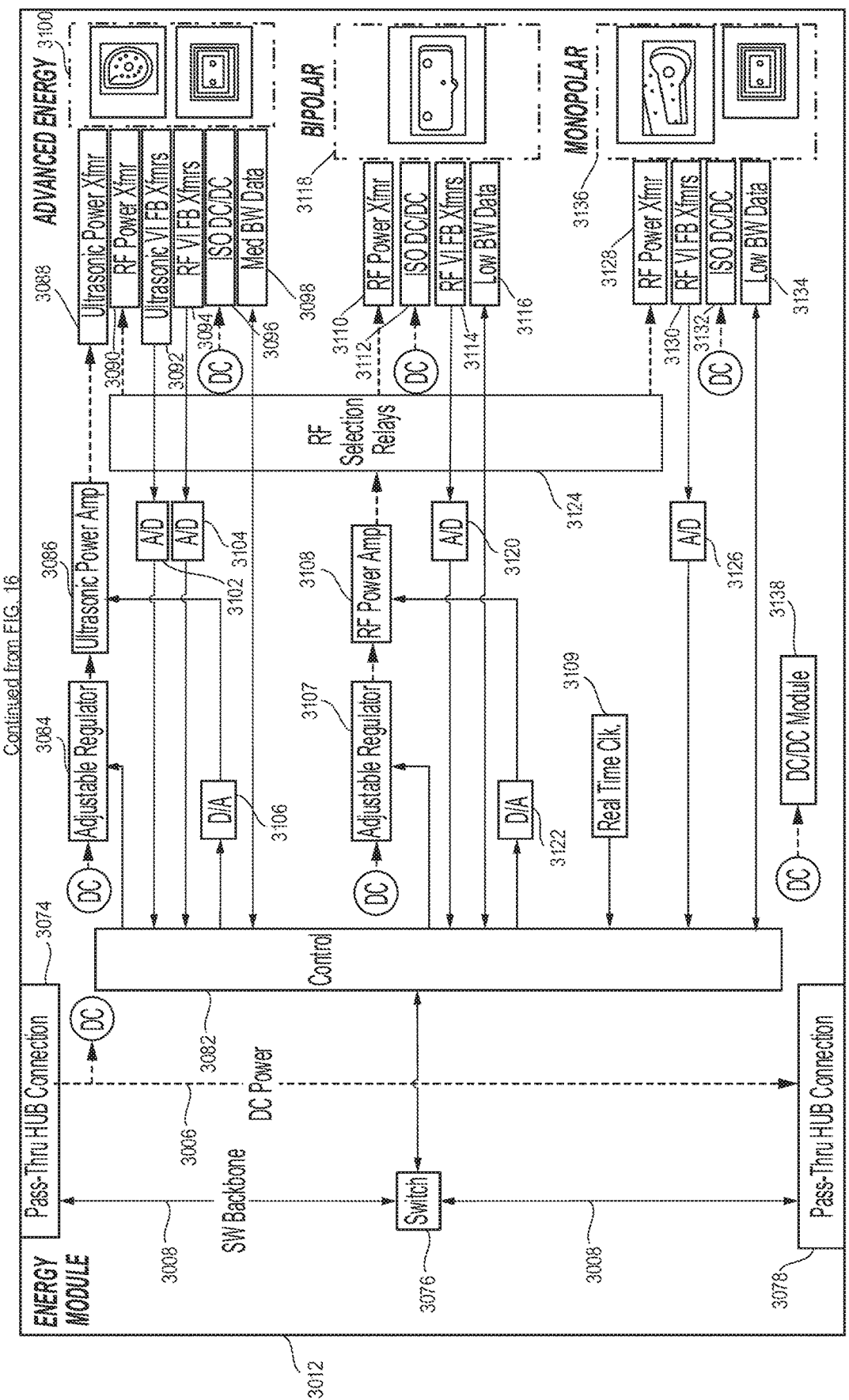
FIGS. 17A and 17B illustrate a block diagram of an energy module coupled to a header module of a modular energy system, in accordance with at least one aspect of the present disclosure.
Figure 17B:
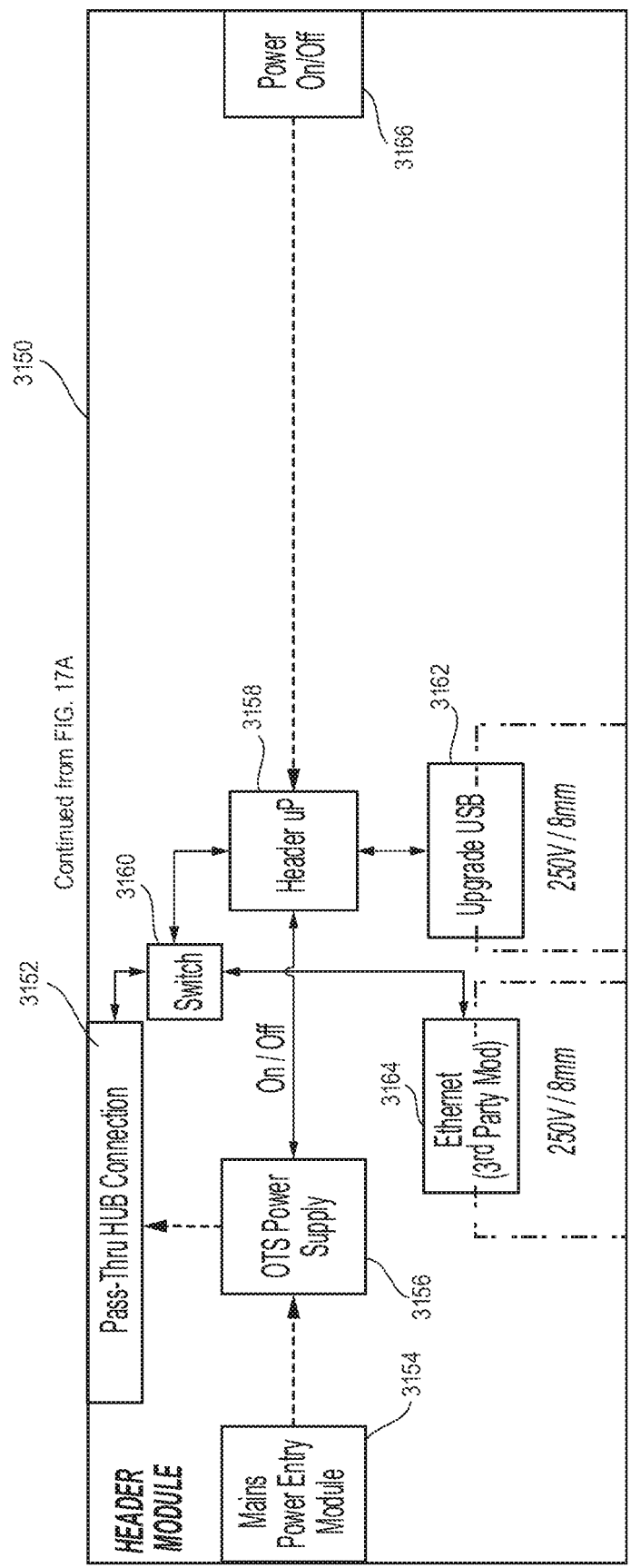

FIGS. 15-17 are block diagrams of various modular energy systems connected together to form a hub, in accordance with at least one aspect of the present disclosure. FIGS. 15-17 depict various diagrams (e.g., circuit or control diagrams) of hub modules. The modular energy system 3000 includes multiple energy modules 3004 (FIG. 16), 3012 (FIG. 17), a header module 3150 (FIG. 17), a UI module 3030 (FIG. 15), and a communications module 3032 (FIG. 15), in accordance with at least one aspect of the present disclosure. The UI module 3030 includes a touch screen 3046 displaying various relevant information and various user controls for controlling one or more parameters of the modular energy system 3000. The UI module 3030 is attached to the top header module 3150, but is separately housed so that it can be manipulated independently of the header module 3150. For example, the UI module 3030 can be picked up by a user and/or reattached to the header module 3150. Additionally, or alternatively, the UI module 3030 can be slightly moved relative to the header module 3150 to adjust its position and/or orientation. For example, the UI module 3030 can be tilted and/or rotated relative to the header module 3150.

In some aspects, the various hub modules can include light piping around the physical ports to communicate instrument status and also connect on-screen elements to corresponding instruments. Light piping is one example of an illumination technique that may be employed to alert a user to a status of a surgical instrument attached/connected to a physical port. In one aspect, illuminating a physical port with a particular light directs a user to connect a surgical instrument to the physical port. In another example, illuminating a physical port with a particular light alerts a user to an error related an existing connection with a surgical instrument.

Turning to FIG. 15, there is shown a block diagram of a user interface (UI) module 3030 coupled to a communications module 3032 via a pass-through hub connector 3034, in accordance with at least one aspect of the present disclosure. The UI module 3030 is provided as a separate component from a header module 3150 (shown in FIG. 17) and may be communicatively coupled to the header module 3150 via a communications module 3032, for example. In one aspect, the UI module 3030 can include a UI processor 3040 that is configured to represent declarative visualizations and behaviors received from other connected modules, as well as perform other centralized UI functionality, such as system configuration (e.g., language selection, module associations, etc.). The UI processor 3040 can be, for example, a processor or system on module (SOM) running a framework such as Qt, .NET WPF, Web server, or similar.

In the illustrated example, the UI module 3030 includes a touchscreen 3046, a liquid crystal display 3048 (LCD), and audio output 3052 (e.g., speaker, buzzer). The UI processor 3040 is configured to receive touchscreen inputs from a touch controller 3044 coupled between the touch screen 3046 and the UI processor 3040. The UI processor 3040 is configured to output visual information to the LCD display 3048 and to output audio information the audio output 3052 via an audio amplifier 3050. The UI processor 3040 is configured to interface to the communications module 3032 via a switch 3042 coupled to the pass-through hub connector 3034 to receive, process, and forward data from the source device to the destination device and control data communication therebetween. DC power is supplied to the UI module 3030 via DC/DC converter modules 3054. The DC power is passed through the pass-through hub connector 3034 to the communications module 3032 through the power bus 3006. Data is passed through the pass-through hub connector 3034 to the communications module 3032 through the data bus 3008. Switches 3042, 3056 receive, process, and forward data from the source device to the destination device.

Continuing with FIG. 15, the communications module 3032, as well as various surgical hubs and/or surgical systems can include a gateway 3058 that is configured to shuttle select traffic (i.e., data) between two disparate networks (e.g., an internal network and/or a hospital network) that are running different protocols. The communications module 3032 includes a first pass-through hub connector 3036 to couple the communications module 3032 to other modules. In the illustrated example, the communications module 3032 is coupled to the UI module 3030. The communications module 3032 is configured to couple to other modules (e.g., energy modules) via a second pass-through hub connector 3038 to couple the communications module 3032 to other modules via a switch 3056 disposed between the first and second pass-through hub connectors 3036, 3038 to receive, process, and forward data from the source device to the destination device and control data communication therebetween. The switch 3056 also is coupled to a gateway 3058 to communicate information between external communications ports and the UI module 3030 and other connected modules. The gateway 3058 may be coupled to various communications modules such as, for example, an Ethernet module 3060 to communicate to a hospital or other local network, a universal serial bus (USB) module 3062, a WiFi module 3064, and a Bluetooth module 3066, among others. The communications modules may be physical boards located within the communications module 3032 or may be a port to couple to remote communications boards.

Figure 18A:
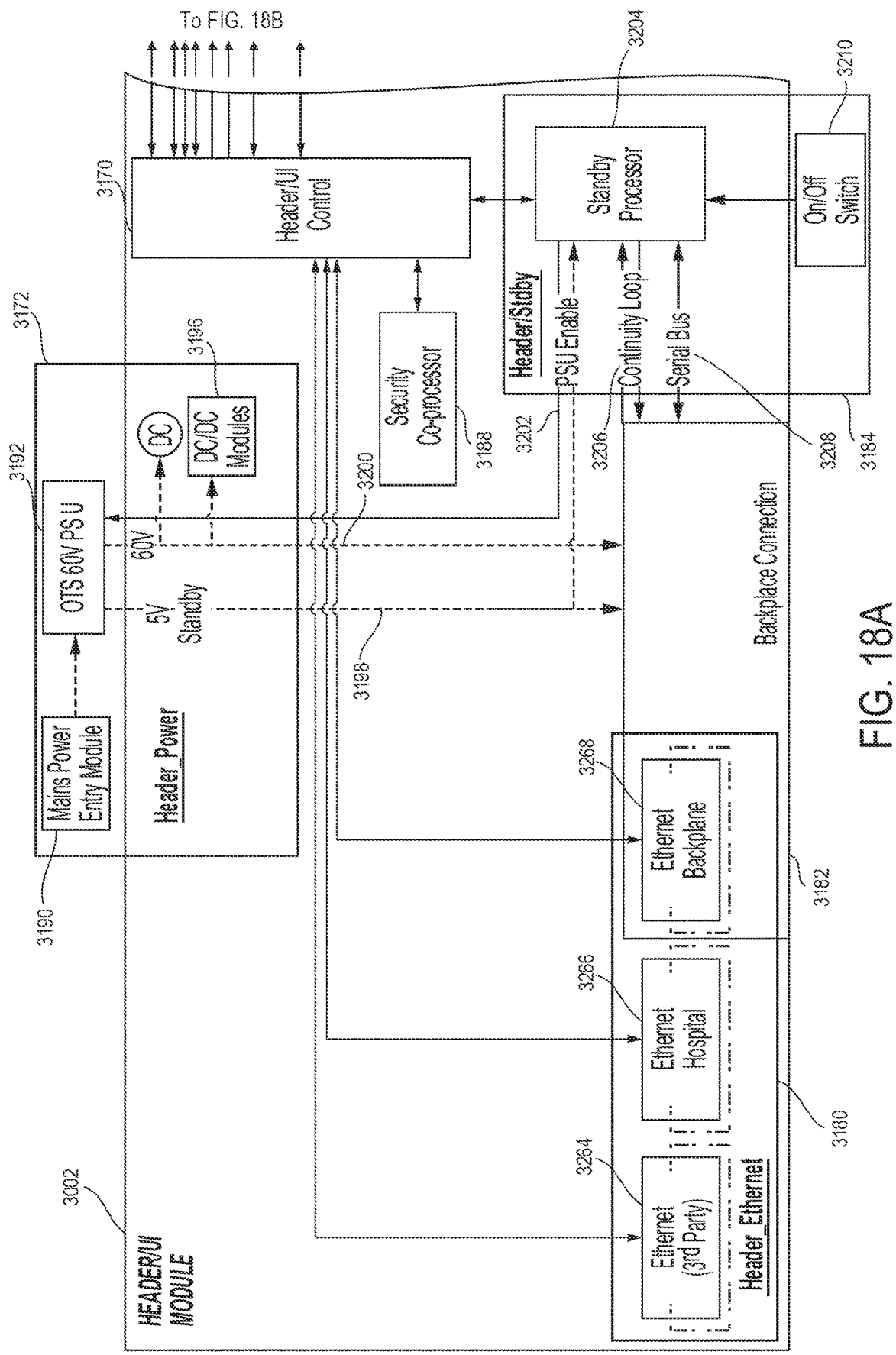
FIGS. 18A and 18B illustrate a block diagram of a header/user interface (UI) module of a modular energy system for a hub, such as the header module depicted in FIG. 15, in accordance with at least one aspect of the present disclosure.
Figure 18B:
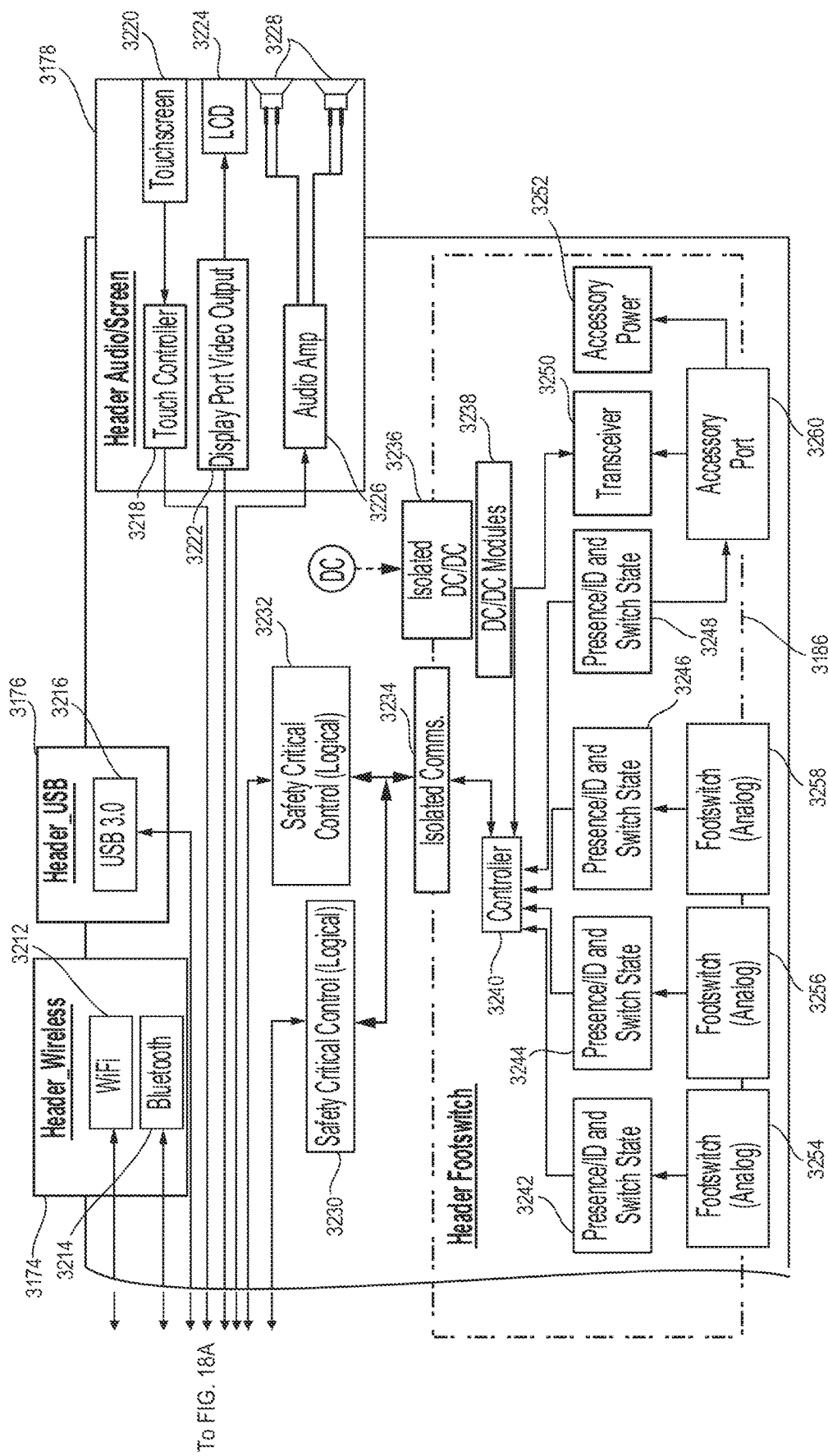

In some aspects, all of the modules (i.e., detachable hardware) are controlled by a single UI module 3030 that is disposed on or integral to a header module. FIG. 17 shows a stand alone header module 3150 to which the UI module 3030 can be attached. FIGS. 13, 14, and 18 show an integrated header/UI Module 3002. Returning now to FIG. 15, in various aspects, by consolidating all of the modules into a single, responsive UI module 3002, the system provides a simpler way to control and monitor multiple pieces of equipment at once. This approach drastically reduces footprint and complexity in an operating room (OR).

Turning to FIG. 16, there is shown a block diagram of an energy module 3004, in accordance with at least one aspect of the present disclosure. The communications module 3032 (FIG. 15) is coupled to the energy module 3004 via the second pass-through hub connector 3038 of the communications module 3032 and a first pass-through hub connector 3074 of the energy module 3004. The energy module 3004 may be coupled to other modules, such as a second energy module 3012 shown in FIG. 17, via a second pass-through hub connector 3078. Turning back to FIG. 16, a switch 3076 disposed between the first and second pass-through hub connectors 3074, 3078 receives, processes, and forwards data from the source device to the destination device and controls data communication therebetween. Data is received and transmitted through the data bus 3008. The energy module 3032 includes a controller 3082 to control various communications and processing functions of the energy module 3004.

DC power is received and transmitted by the energy module 3004 through the power bus 3006. The power bus 3006 is coupled to DC/DC converter modules 3138 to supply power to adjustable regulators 3084, 3107 and isolated DC/DC converter ports 3096, 3112, 3132.

In one aspect, the energy module 3004 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of an advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog-to-digital converter 3102 (A/D). Also coupled to the controller 3082 through the advanced energy receptacle 3100 is the isolated DC/DC converter port 3096, which receives DC power from the power bus 3006, and a medium bandwidth data port 3098.

In one aspect, the energy module 3004 can include a wideband RF power amplifier 3108, which in one aspect may be a linear class H amplifier that is capable of generating arbitrary waveforms and drive RF loads at a range of output frequencies. The wideband RF power amplifier 3108 is fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the wideband RF amplifier 3086 via a DAC 3122. The output of the wideband RF power amplifier 3108 can be fed through RF selection relays 3124. The RF selection relays 3124 are configured to receive and selectively transmit the output signal of the wideband RF power amplifier 3108 to various other components of the energy module 3004. In one aspect, the output signal of the wideband RF power amplifier 3108 can be fed through RF selection relays 3124 to an RF power transformer 3110, which is coupled to an RF output portion of a bipolar RF energy receptacle 3118. Bipolar RF voltage (V) and current (I) feedback (FB) signals, which may be employed to compute RF impedance, are fed back to the controller 3082 via an RF VI FB transformer 3114 through an input portion of the bipolar RF energy receptacle 3118. The RF voltage and current feedback signals are routed back to the controller 3082 through an A/D 3120. Also coupled to the controller 3082 through the bipolar RF energy receptacle 3118 is the isolated DC/DC converter port 3112, which receives DC power from the power bus 3006, and a low bandwidth data port 3116.

As described above, in one aspect, the energy module 3004 can include RF selection relays 3124 driven by the controller 3082 (e.g., FPGA) at rated coil current for actuation and can also be set to a lower hold-current via pulse-width modulation (PWM) to limit steady-state power dissipation. Switching of the RF selection relays 3124 is achieved with force guided (safety) relays and the status of the contact state is sensed by the controller 3082 as a mitigation for any single fault conditions. In one aspect, the RF selection relays 3124 are configured to be in a first state, where an output RF signal received from an RF source, such as the wideband RF power amplifier 3108, is transmitted to a first component of the energy module 3004, such as the RF power transformer 3110 of the bipolar energy receptacle 3118. In a second aspect, the RF selection relays 3124 are configured to be in a second state, where an output RF signal received from an RF source, such as the wideband RF power amplifier 3108, is transmitted to a second component, such as an RF power transformer 3128 of a monopolar energy receptacle 3136, described in more detail below. In a general aspect, the RF selection relays 3124 are configured to be driven by the controller 3082 to switch between a plurality of states, such as the first state and the second state, to transmit the output RF signal received from the RF power amplifier 3108 between different energy receptacles of the energy module 3004.

As described above, the output of the wideband RF power amplifier 3108 can also fed through the RF selection relays 3124 to the wideband RF power transformer 3128 of the RF monopolar receptacle 3136. Monopolar RF voltage (V) and current (I) feedback (FB) signals, which may be employed to compute RF impedance, are fed back to the controller 3082 via an RF VI FB transformer 3130 through an input portion of the monopolar RF energy receptacle 3136. The RF voltage and current feedback signals are routed back to the controller 3082 through an A/D 3126. Also coupled to the controller 3082 through the monopolar RF energy receptacle 3136 is the isolated DC/DC converter port 3132, which receives DC power from the power bus 3006, and a low bandwidth data port 3134.

The output of the wideband RF power amplifier 3108 can also fed through the RF selection relays 3124 to the wideband RF power transformer 3090 of the advanced energy receptacle 3100. RF voltage (V) and current (I) feedback (FB) signals, which may be employed to compute RF impedance, are fed back to the controller 3082 via an RF VI FB transformer 3094 through an input portion of the advanced energy receptacle 3100. The RF voltage and current feedback signals are routed back to the controller 3082 through an A/D 3104.

FIG. 17 is a block diagram of a second energy module 3012 coupled to a header module 3150, in accordance with at least one aspect of the present disclosure. The first energy module 3004 shown in FIG. 16 is coupled to the second energy module 3012 shown in FIG. 17 by coupling the second pass-through hub connector 3078 of the first energy module 3004 to a first pass-through hub connector 3074 of the second energy module 3012. In one aspect, the second energy module 3012 can a similar energy module to the first energy module 3004, as is illustrated in FIG. 17. In another aspect, the second energy module 2012 can be a different energy module compared to the first energy module, such as an energy module illustrated in FIG. 19, described in more detail. The addition of the second energy module 3012 to the first energy module 3004 adds functionality to the modular energy system 3000.

The second energy module 3012 is coupled to the header module 3150 by connecting the pass-through hub connector 3078 to the pass-through hub connector 3152 of the header module 3150. In one aspect, the header module 3150 can include a header processor 3158 that is configured to manage a power button function 3166, software upgrades through the upgrade USB module 3162, system time management, and gateway to external networks (i.e., hospital or the cloud) via an Ethernet module 3164 that may be running different protocols. Data is received by the header module 3150 through the pass-through hub connector 3152. The header processor 3158 also is coupled to a switch 3160 to receive, process, and forward data from the source device to the destination device and control data communication therebetween. The header processor 3158 also is coupled to an OTS power supply 3156 coupled to a mains power entry module 3154.

FIG. 18 is a block diagram of a header/user interface (UI) module 3002 for a hub, such as the header module depicted in FIG. 15, in accordance with at least one aspect of the present disclosure. The header/UI module 3002 includes a header power module 3172, a header wireless module 3174, a header USB module 3176, a header audio/screen module 3178, a header network module 3180 (e.g., Ethernet), a backplane connector 3182, a header standby processor module 3184, and a header footswitch module 3186. These functional modules interact to provide the header/UI 3002 functionality. A header/UI controller 3170 controls each of the functional modules and the communication therebetween including safety critical control logic modules 3230, 3232 coupled between the header/UI controller 3170 and an isolated communications module 3234 coupled to the header footswitch module 3186. A security co-processor 3188 is coupled to the header/UI controller 3170.

The header power module 3172 includes a mains power entry module 3190 coupled to an OTS power supply unit 3192 (PSU). Low voltage direct current (e.g., 5V) standby power is supplied to the header/UI module 3002 and other modules through a low voltage power bus 3198 from the OTS PSU 3192. High voltage direct current (e.g., 60V) is supplied to the header/UI module 3002 through a high voltage bus 3200 from the OTS PSU 3192. The high voltage DC supplies DC/DC converter modules 3196 as well as isolated DC/DC converter modules 3236. A standby processor 3204 of the header/standby module 3184 provides a PSU/enable signal 3202 to the OTS PSU 3192.

The header wireless module 3174 includes a WiFi module 3212 and a Bluetooth module 3214. Both the WiFi module 3212 and the Bluetooth module 3214 are coupled to the header/UI controller 3170. The Bluetooth module 3214 is used to connect devices without using cables and the Wi-Fi module 3212 provides high-speed access to networks such as the Internet and can be employed to create a wireless network that can link multiple devices such as, for examples, multiple energy modules or other modules and surgical instruments, among other devices located in the operating room. Bluetooth is a wireless technology standard that is used to exchange data over short distances, such as, less than 30 feet.

The header USB module 3176 includes a USB port 3216 coupled to the header/UI controller 3170. The USB module 3176 provides a standard cable connection interface for modules and other electronics devices over short-distance digital data communications. The USB module 3176 allows modules comprising USB devices to be connected to each other with and transfer digital data over USB cables.

The header audio/screen module 3178 includes a touchscreen 3220 coupled to a touch controller 3218. The touch controller 3218 is coupled to the header/UI controller 3170 to read inputs from the touchscreen 3220. The header/UI controller 3170 drives an LCD display 3224 through a display/port video output signal 3222. The header/UI controller 3170 is coupled to an audio amplifier 3226 to drive one or more speakers 3228.

In one aspect, the header/UI module 3002 provides a touchscreen 3220 user interface configured to control modules connected to one control or header module 3002 in a modular energy system 3000. The touchscreen 3220 can be used to maintain a single point of access for the user to adjust all modules connected within the modular energy system 3000. Additional hardware modules (e.g., a smoke evacuation module) can appear at the bottom of the user interface LCD display 3224 when they become connected to the header/UI module 3002, and can disappear from the user interface LCD display 3224 when they are disconnected from the header/UI module 3002.

Further, the user touchscreen 3220 can provide access to the settings of modules attached to the modular energy system 3000. Further, the user interface LCD display 3224 arrangement can be configured to change according to the number and types of modules that are connected to the header/UI module 3002. For example, a first user interface can be displayed on the LCD display 3224 for a first application where one energy module and one smoke evacuation module are connected to the header/UI module 3002, and a second user interface can be displayed on the LCD display 3224 for a second application where two energy modules are connected to the header/UI module 3002. Further, the user interface can alter its display on the LCD display 3224 as modules are connected and disconnected from the modular energy system 3000.

In one aspect, the header/UI module 3002 provides a user interface LCD display 3224 configured to display on the LCD display coloring corresponds to the port lighting. In one aspect, the coloring of the instrument panel and the LED light around its corresponding port will be the same or otherwise correspond with each other. Each color can, for example, convey a unique meaning. This way, the user will be able to quickly assess which instrument the indication is referring to and the nature of the indication. Further, indications regarding an instrument can be represented by the changing of color of the LED light lined around its corresponding port and the coloring of its module. Still further, the message on screen and hardware/software port alignment can also serve to convey that an action must be taken on the hardware, not on the interface. In various aspects, all other instruments can be used while alerts are occurring on other instruments. This allows the user to be able to quickly assess which instrument the indication is referring to and the nature of the indication.

In one aspect, the header/UI module 3002 provides a user interface screen configured to display on the LCD display 3224 to present procedure options to a user. In one aspect, the user interface can be configured to present the user with a series of options (which can be arranged, e.g., from broad to specific). After each selection is made, the modular energy system 3000 presents the next level until all selections are complete. These settings could be managed locally and transferred via a secondary means (such as a USB thumb drive). Alternatively, the settings could be managed via a portal and automatically distributed to all connected systems in the hospital.

The procedure options can include, for example, a list of factory preset options categorized by specialty, procedure, and type of procedure. Upon completing a user selection, the header module can be configured to set any connected instruments to factory-preset settings for that specific procedure. The procedure options can also include, for example, a list of surgeons, then subsequently, the specialty, procedure, and type. Once a user completes a selection, the system may suggest the surgeon's preferred instruments and set those instrument's settings according to the surgeon's preference (i.e., a profile associated with each surgeon storing the surgeon's preferences).

In one aspect, the header/UI module 3002 provides a user interface screen configured to display on the LCD display 3224 critical instrument settings. In one aspect, each instrument panel displayed on the LCD display 3224 of the user interface corresponds, in placement and content, to the instruments plugged into the modular energy system 3000. When a user taps on a panel, it can expand to reveal additional settings and options for that specific instrument and the rest of the screen can, for example, darken or otherwise be de-emphasized.

In one aspect, the header/UI module 3002 provides an instrument settings panel of the user interface configured to comprise/display controls that are unique to an instrument and allow the user to increase or decrease the intensity of its output, toggle certain functions, pair it with system accessories like a footswitch connected to header footswitch module 3186, access advanced instrument settings, and find additional information about the instrument. In one aspect, the user can tap/select an "Advanced Settings" control to expand the advanced settings drawer displayed on the user interface LCD display 3224. In one aspect, the user can then tap/select an icon at the top right-hand corner of the instrument settings panel or tap anywhere outside of the panel and the panel will scale back down to its original state. In these aspects, the user interface is configured to display on the LCD display 3224 only the most critical instrument settings, such as power level and power mode, on the ready/home screen for each instrument panel. This is to maximize the size and readability of the system from a distance. In some aspects, the panels and the settings within can be scaled proportionally to the number of instruments connected to the system to further improve readability. As more instruments are connected, the panels scale to accommodate a greater amount of information.

The header network module 3180 includes a plurality of network interfaces 3264, 3266, 3268 (e.g., Ethernet) to network the header/UI module 3002 to other modules of the modular energy system 3000. In the illustrated example, one network interface 3264 may be a 3rd party network interface, another network interface 3266 may be a hospital network interface, and yet another network interface 3268 may be located on the backplane network interface connector 3182.

The header standby processor module 3184 includes a standby processor 3204 coupled to an On/Off switch 3210. The standby processor 3204 conducts an electrical continuity test by checking to see if electrical current flows in a continuity loop 3206. The continuity test is performed by placing a small voltage across the continuity loop 3206. A serial bus 3208 couples the standby processor 3204 to the backplane connector 3182.

The header footswitch module 3186 includes a controller 3240 coupled to a plurality of analog footswitch ports 3254, 3256, 3258 through a plurality of corresponding presence/ID and switch state modules 3242, 3244, 3246, respectively. The controller 3240 also is coupled to an accessory port 3260 via a presence/ID and switch state module 3248 and a transceiver module 3250. The accessory port 3260 is powered by an accessory power module 3252. The controller 3240 is coupled to header/UI controller 3170 via an isolated communication module 3234 and first and second safety critical control modules 3230, 3232. The header footswitch module 3186 also includes DC/DC converter modules 3238.

In one aspect, the header/UI module 3002 provides a user interface screen configured to display on the LCD display 3224 for controlling a footswitch connected to any one of the analog footswitch ports 3254, 3256, 3258. In some aspects, when the user plugs in a non hand-activated instrument into any one of the analog footswitch ports 3254, 3256, 3258, the instrument panel appears with a warning icon next to the footswitch icon. The instrument settings can be, for example, greyed out, as the instrument cannot be activated without a footswitch.

When the user plugs in a footswitch into any one of the analog footswitch ports 3254, 3256, 3258, a pop-up appears indicating that a footswitch has been assigned to that instrument. The footswitch icon indicates that a footswitch has been plugged in and assigned to the instrument. The user can then tap/select on that icon to assign, reassign, unassign, or otherwise change the settings associated with that footswitch. In these aspects, the system is configured to automatically assign footswitches to non hand-activated instruments using logic, which can further assign single or double-pedal footswitches to the appropriate instrument. If the user wants to assign/reassign footswitches manually there are two flows that can be utilized.

In one aspect, the header/UI module 3002 provides a global footswitch button. Once the user taps on the global footswitch icon (located in the upper right of the user interface LCD display 3224), the footswitch assignment overlay appears and the contents in the instrument modules dim. A (e.g., photo-realistic) representation of each attached footswitch (dual or single-pedal) appears on the bottom if unassigned to an instrument or on the corresponding instrument panel. Accordingly, the user can drag and drop these illustrations into, and out of, the boxed icons in the footswitch assignment overlay to assign, unassign, and reassign footswitches to their respective instruments.

In one aspect, the header/UI module 3002 provides a user interface screen displayed on the LCD display 3224 indicating footswitch auto-assignment, in accordance with at least one aspect of the present disclosure. As discussed above, the modular energy system 3000 can be configured to auto-assign a footswitch to an instrument that does not have hand activation. In some aspects, the header/UI module 3002 can be configured to correlate the colors displayed on the user interface LCD display 3224 to the lights on the modules themselves as means of tracking physical ports with user interface elements.

In one aspect, the header/UI module 3002 may be configured to depict various applications of the user interface with differing number of modules connected to the modular energy system 3000. In various aspects, the overall layout or proportion of the user interface elements displayed on the LCD display 3224 can be based on the number and type of instruments plugged into the header/UI module 3002. These scalable graphics can provide the means to utilize more of the screen for better visualization.

In one aspect, the header/UI module 3002 may be configured to depict a user interface screen on the LCD display 3224 to indicate which ports of the modules connected to the modular energy system 3000 are active. In some aspects, the header/UI module 3002 can be configured to illustrate active versus inactive ports by highlighting active ports and dimming inactive ports. In one aspect, ports can be represented with color when active (e.g., monopolar tissue cut with yellow, monopolar tissue coagulation with blue, bipolar tissue cut with blue, advanced energy tissue cut with warm white, and so on). Further, the displayed color will match the color of the light piping around the ports. The coloring can further indicate that the user cannot change settings of other instruments while an instrument is active. As another example, the header/UI module 3002 can be configured to depict the bipolar, monopolar, and ultrasonic ports of a first energy module as active and the monopolar ports of a second energy module as likewise active.

In one aspect, the header/UI module 3002 can be configured to depict a user interface screen on the LCD display 3224 to display a global settings menu. In one aspect, the header/UI module 3002 can be configured to display a menu on the LCD display 3224 to control global settings across any modules connected to the modular energy system 3000. The global settings menu can be, for example, always displayed in a consistent location (e.g., always available in upper right hand corner of main screen).

In one aspect, the header/UI module 3002 can be configured to depict a user interface screen on the LCD display 3224 configured to prevent changing of settings while a surgical instrument is in use. In one example, the header/UI module 3002 can be configured to prevent settings from being changed via a displayed menu when a connected instrument is active. The user interface screen can include, for example, an area (e.g., the upper left hand corner) that is reserved for indicating instrument activation while a settings menu is open. In one aspect, a user has opened the bipolar settings while monopolar coagulation is active. In one aspect, the settings menu could then be used once the activation is complete. In one aspect, the header/UI module 3002 can be is configured to never overlay any menus or other information over the dedicated area for indicating critical instrument information in order to maintain display of critical information.

In one aspect, the header/UI module 3002 can be configured to depict a user interface screen on the LCD display 3224 configured to display instrument errors. In one aspect, instrument error warnings may be displayed on the instrument panel itself, allowing user to continue to use other instruments while a nurse troubleshoots the error. This allows users to continue the surgery without the need to stop the surgery to debug the instrument.

In one aspect, the header/UI module 3002 can be configured to depict a user interface screen on the LCD display 3224 to display different modes or settings available for various instruments. In various aspects, the header/UI module 3002 can be configured to display settings menus that are appropriate for the type or application of surgical instrument(s) connected to the stack/hub. Each settings menu can provide options for different power levels, energy delivery profiles, and so on that are appropriate for the particular instrument type. In one aspect, the header/UI module 3002 can be configured to display different modes available for bipolar, monopolar cut, and monopolar coagulation applications.

In one aspect, the header/UI module 3002 can be configured to depict a user interface screen on the LCD display 3224 to display pre-selected settings. In one aspect, the header/UI module 3002 can be configured to receive selections for the instrument/device settings before plugging in instruments so that the modular energy system 3000 is ready before the patient enters the operating room. In one aspect, the user can simply click a port and then change the settings for that port. In the depicted aspect, the selected port appears as faded to indicate settings are set, but no instrument is plugged into that port.

Figure 19:
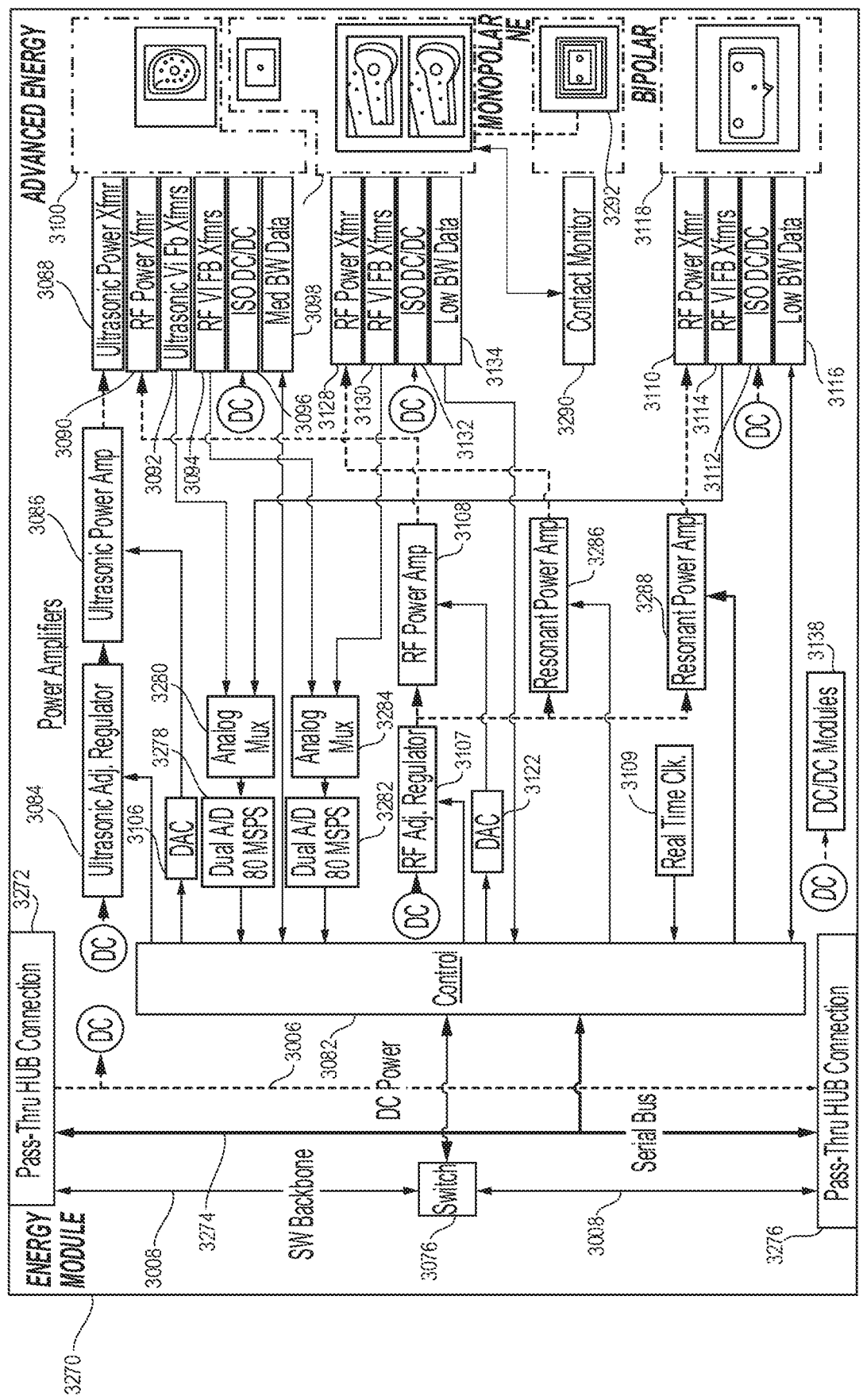
FIG. 19 is a block diagram of an energy module for a hub, such as the energy module depicted in FIGS. 13-18B, in accordance with at least one aspect of the present disclosure.

FIG. 19 is a block diagram of an energy module 3270 for a hub, such as the energy module depicted in FIGS. 13, 14, 16, and 17, in accordance with at least one aspect of the present disclosure. The energy module 3270 is configured to couple to a header module, header/UI module, and other energy modules via the first and second pass-through hub connectors 3272, 3276. A switch 3076 disposed between the first and second pass-through hub connectors 3272, 3276 receives, processes, and forwards data from the source device to the destination device and controls data communication therebetween. Data is received and transmitted through the data bus 3008. The energy module 3270 includes a controller 3082 to control various communications and processing functions of the energy module 3270.

DC power is received and transmitted by the energy module 3270 through the power bus 3006. The power bus 3006 is coupled to the DC/DC converter modules 3138 to supply power to adjustable regulators 3084, 3107 and isolated DC/DC converter ports 3096, 3112, 3132.

In one aspect, the energy module 3270 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of the advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog multiplexer 3280 and a dual analog-to-digital converter 3278 (A/D). In one aspect, the dual A/D 3278 has a sampling rate of 80 MSPS. Also coupled to the controller 3082 through the advanced energy receptacle 3100 is the isolated DC/DC converter port 3096, which receives DC power from the power bus 3006, and a medium bandwidth data port 3098.

In one aspect, the energy module 3270 can include a plurality of wideband RF power amplifiers 3108, 3286, 3288, among others, which in one aspect, each of the wideband RF power amplifiers 3108, 3286, 3288 may be linear class H amplifiers capable of generating arbitrary waveforms and drive RF loads at a range of output frequencies. Each of the wideband RF power amplifiers 3108, 3286, 3288 are fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the first wideband RF power amplifier 3108 via a DAC 3122.

Unlike the energy modules 3004, 3012 shown and described in FIGS. 16 and 17, the energy module 3270 does not include RF selection relays configured to receive an RF output signal from the adjustable buck regulator 3107. In addition, unlike the energy modules 3004, 3012 shown and described in FIGS. 16 and 17, the energy module 3270 includes a plurality of wideband RF power amplifiers 3108, 3286, 3288 instead of a single RF power amplifier. In one aspect, the adjustable buck regulator 3107 can switch between a plurality of states, in which the adjustable buck regulator 3107 outputs an output RF signal to one of the plurality of wideband RF power amplifiers 3108, 3286, 3288 connected thereto. The controller 3082 is configured to switch the adjustable buck regulator 3107 between the plurality of states. In a first state, the controller drives the adjustable buck regulator 3107 to output an RF energy signal to the first wideband RF power amplifier 3108. In a second state, the controller drives the adjustable buck regulator 3107 to output an RF energy signal to the second wideband RF power amplifier 3286. In a third state, the controller drives the adjustable buck regulator 3107 to output an RF energy signal to the third wideband RF power amplifier 3288.

The output of the first wideband RF power amplifier 3108 can be fed to an RF power transformer 3090, which is coupled to an RF output portion of an advanced energy receptacle 3100. RF voltage (V) and current (I) feedback (FB) signals, which may be employed to compute RF impedance, are fed back to the controller 3082 via RF VI FB transformers 3094 through an input portion of the advanced energy receptacle 3100. The RF voltage and current feedback signals are routed back to the controller 3082 through the RF VI FB transformers 3094, which are coupled to an analog multiplexer 3284 and a dual A/D 3282 coupled to the controller 3082. In one aspect, the dual A/D 3282 has a sampling rate of 80 MSPS.

The output of the second RF wideband power amplifier 3286 is fed through an RF power transformer 3128 of the RF monopolar receptacle 3136. Monopolar RF voltage (V) and current (I) feedback (FB) signals, which may be employed to compute RF impedance, are fed back to the controller 3082 via RF VI FB transformers 3130 through an input portion of the monopolar RF energy receptacle 3136. The RF voltage and current feedback signals are routed back to the controller 3082 through the analog multiplexer 3284 and the dual A/D 3282. Also coupled to the controller 3082 through the monopolar RF energy receptacle 3136 is the isolated DC/DC converter port 3132, which receives DC power from the power bus 3006, and a low bandwidth data port 3134.

The output of the third RF wideband power amplifier 3288 is fed through an RF power transformer 3110 of a bipolar RF receptacle 3118. Bipolar RF voltage (V) and current (I) feedback (FB) signals, which may be employed to compute RF impedance, are fed back to the controller 3082 via RF VI FB transformers 3114 through an input portion of the bipolar RF energy receptacle 3118. The RF voltage and current feedback signals are routed back to the controller 3082 through the analog multiplexer 3280 and the dual A/D 3278. Also coupled to the controller 3082 through the bipolar RF energy receptacle 3118 is the isolated DC/DC converter port 3112, which receives DC power from the power bus 3006, and a low bandwidth data port 3116.

A contact monitor 3290 is coupled to an NE receptacle 3292. Power is fed to the NE receptacle 3292 from the monopolar receptacle 3136.

In one aspect, with reference to FIGS. 13-19, the modular energy system 3000 can be configured to detect instrument presence in a receptacle 3100, 3118, 3136 via a photo-interrupter, magnetic sensor, or other non-contact sensor integrated into the receptacle 3100, 3118, 3136. This approach prevents the necessity of allocating a dedicated presence pin on the MTD connector to a single purpose and instead allows multi-purpose functionality for MTD signal pins 6-9 while continuously monitoring instrument presence.

In one aspect, with reference to FIGS. 13-19, the modules of the modular energy system 3000 can include an optical link allowing high speed communication (10-50 Mb/s) across the patient isolation boundary. This link would carry device communications, mitigation signals (watchdog, etc.), and low bandwidth run-time data. In some aspects, the optical link(s) will not contain real-time sampled data, which can be done on the non-isolated side.

In one aspect, with reference to FIGS. 13-19, the modules of the modular energy system 3000 can include a multi-function circuit block which can: (i) read presence resistor values via A/D and current source, (ii) communicate with legacy instruments via hand switch Q protocols, (iii) communicate with instruments via local bus 1-Wire protocols, and (iv) communicate with CAN FD-enabled surgical instruments. When a surgical instrument is properly identified by an energy generator module, the relevant pin functions and communications circuits are enabled, while the other unused functions are disabled or disconnected and set to a high impedance state.

In one aspect, with reference to FIGS. 13-19, the modules of the modular energy system 3000 can include a pulse/stimulation/auxiliary amplifier. This is a flexible-use amplifier based on a full-bridge output and incorporates functional isolation. This allows its differential output to be referenced to any output connection on the applied part (except, in some aspects, a monopolar active electrode). The amplifier output can be either small signal linear (pulse/stim) with waveform drive provided by a DAC or a square wave drive at moderate output power for DC applications such as DC motors, illumination, FET drive, etc. The output voltage and current are sensed with functionally isolated voltage and current feedback to provide accurate impedance and power measurements to the FPGA. Paired with a CAN FD-enabled instrument, this output can offer motor/motion control drive, while position or velocity feedback is provided by the CAN FD interface for closed loop control.

As described in greater detail herein, a modular energy system comprises a header module and one or more functional or surgical modules. In various instances, the modular energy system is a modular energy system. In various instances, the surgical modules include energy modules, communication modules, user interface modules; however, the surgical modules are envisioned to be any suitable type of functional or surgical module for use with the modular energy system.

Modular energy system offers many advantages in a surgical procedure, as described above in connection with the modular energy systems 2000 (FIGS. 6-12), 3000 (FIGS. 13-15). However, cable management and setup/teardown time can be a significant deterrent. Various aspects of the present disclosure provide a modular energy system with a single power cable and a single power switch to control startup and shutdown of the entire modular energy system, which obviated the need to individually activate and deactivate each individual module from which the modular energy system is constructed. Also, various aspects of the present disclosure provide a modular energy system with power management schemes that facilitate a safe and, in some instances, concurrent delivery of power to the modules of a modular energy system.

Figure 20:
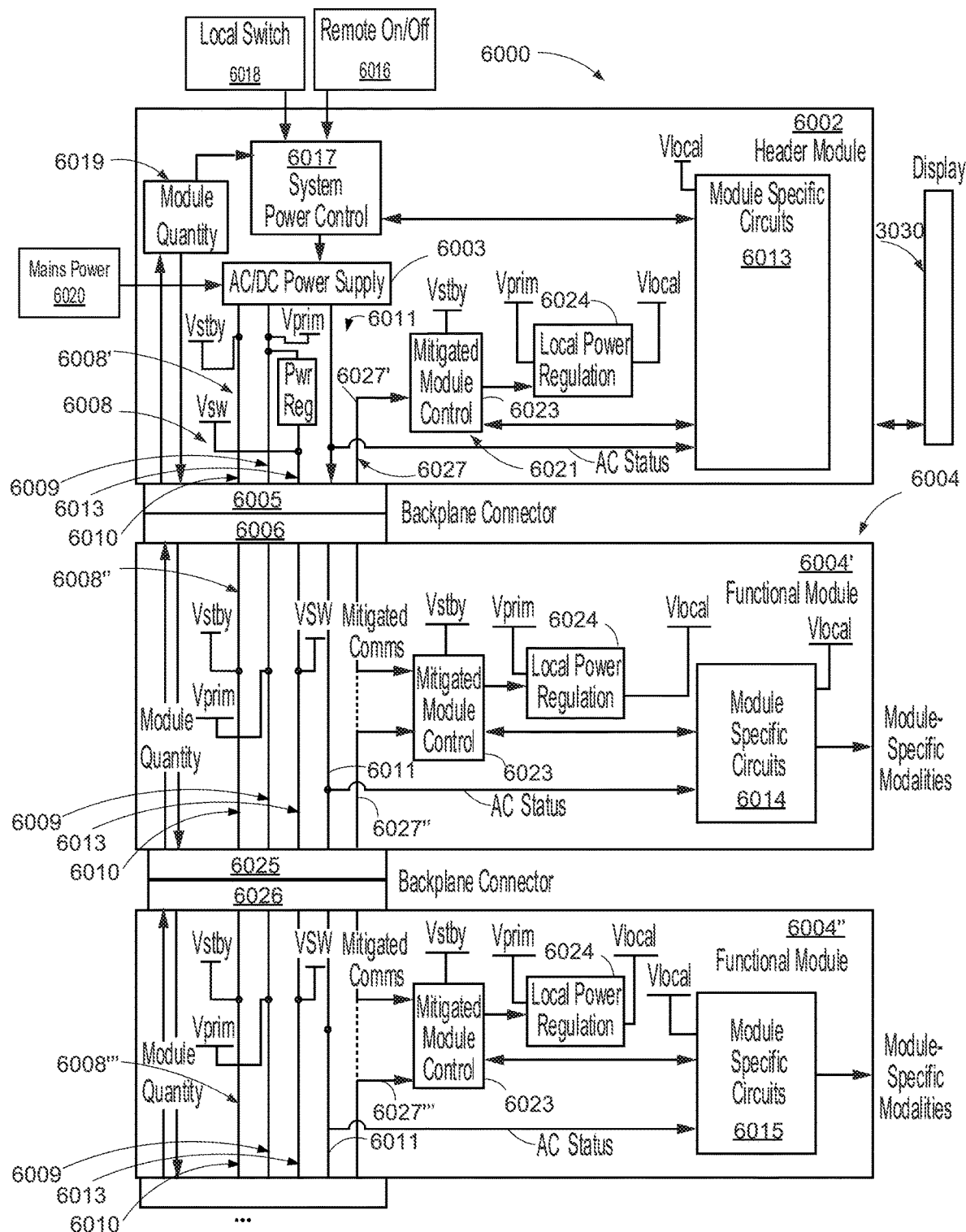
FIG. 20 is a schematic diagram of a modular energy system stack illustrating a power backplane, in accordance with at least one aspect of the present disclosure.

In various aspects, as illustrated in FIG. 20, a modular energy system 6000 that is similar in many respects to the modular energy systems 2000 (FIGS. 6-12), 3000 (FIGS. 13-15). For the sake of brevity, various details of the modular energy system 6000, which are similar to the modular energy system 2000 and/or the modular energy system 3000, are not repeated herein.

The modular energy system 6000 comprises a header module 6002 and an "N" number of surgical modules 6004, where "N" is an integer greater than or equal to one. In various examples, the modular energy system 6000 includes a UI module such as, for example, the UI module 3030 and/or a communication module such as, for example, the communication module 3032. Furthermore, pass-through hub connectors couple individual modules to one another in a stack configuration. In the example of FIG. 20, the header module 6002 is coupled to a surgical module 6004 via pass-through hub connectors 6005, 6006.

The modular energy system 6000 comprises an example power architecture that consists of a single AC/DC power supply 6003 that provides power to all the surgical modules in the stack. The AC/DC power supply 6003 is housed in the header module 6002, and utilizes a power backplane 6008 to distribute power to each module in the stack. The example of FIG. 20 demonstrates three separate power domains on the power backplane 6008: a primary power domain 6009, a standby power domain 6010, and an Ethernet switch power domain 6013.

In the example illustrated in FIG. 20, the power backplane 6008 extends from the header module 6002 through a number of intermediate modules 6004 to a most bottom, or farthest, module in the stack. In various aspects, the power backplane 6008 is configured to deliver power to a surgical module 6004 through one or more other surgical modules 6004 that are ahead of it in the stack. The surgical module 6004 receiving power from the header module 6002 can be coupled to a surgical instrument or tool configured to deliver therapeutic energy to a patient.

The primary power domain 6009 is the primary power source for the functional module-specific circuits 6013, 6014, 6015 of the modules 6002, 6004. It consists of a single voltage rail that is provided to every module. In at least one example, a nominal voltage of 60V can be selected to be higher than the local rails needed by any module, so that the modules can exclusively implement buck regulation, which is generally more efficient than boost regulation.

In various aspects, the primary power domain 6009 is controlled by the header module 6002. In certain instances, as illustrated in FIG. 20, a local power switch 6018 is positioned on the header module 6002. In certain instances, a remote on/off interface 6016 can be configured to control a system power control 6017 on the header module 6002, for example. In at least one example, the remote on/off interface 6016 is configured to transmit pulsed discrete commands (separate commands for On and Off) and a power status telemetry signal. In various instances, the primary power domain 6009 is configured to distribute power to all the modules in the stack configuration following a user-initiated power-up.

Figure 21:
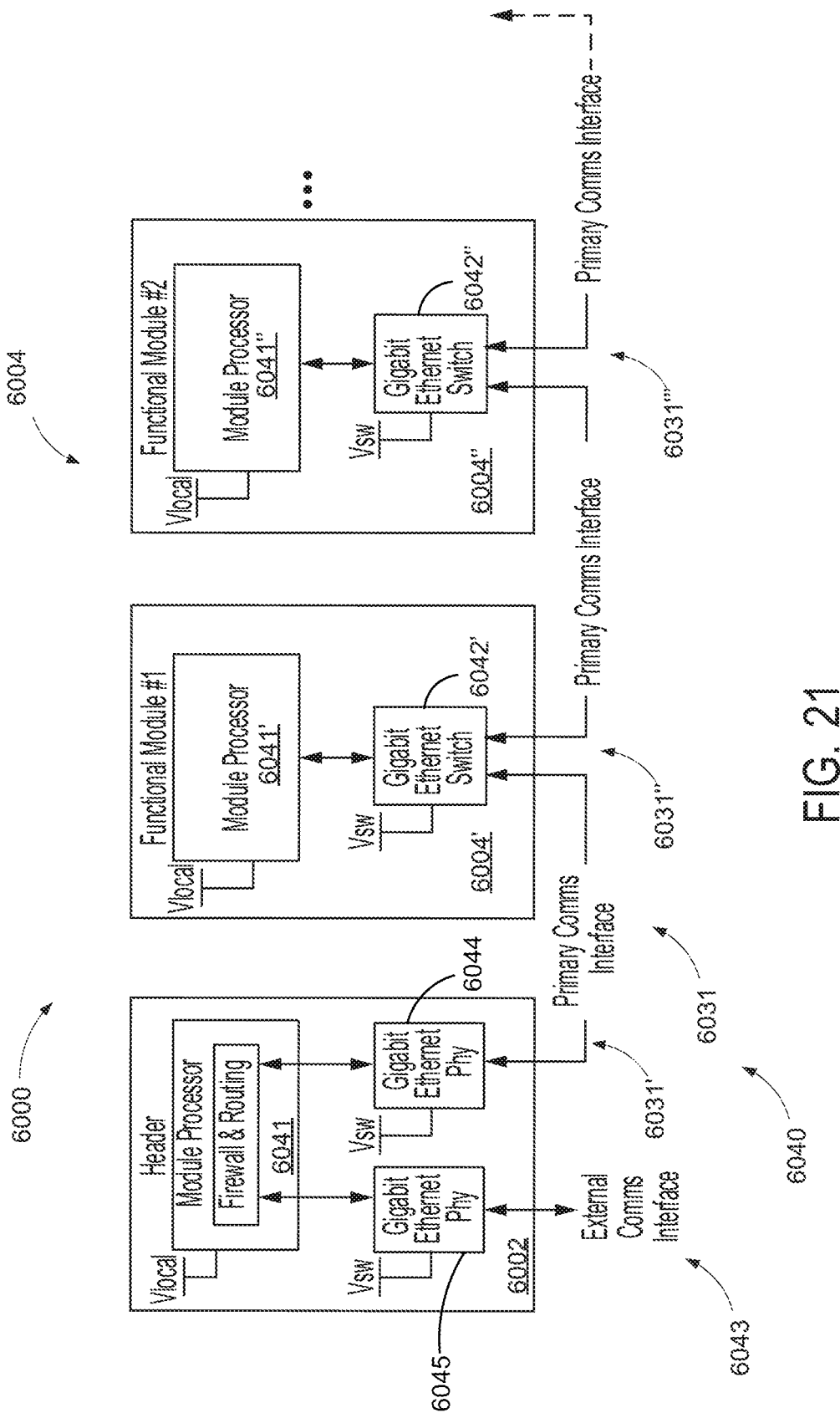
FIG. 21 is a schematic diagram of a modular energy system, in accordance with at least one aspect of the present disclosure.

In various aspects, as illustrated in FIG. 21, the modules of the modular energy system 6000 can be communicably coupled to the header module 6002 and/or to each other via a communication (Serial bus/Ethernet) interface 6040 such that data or other information is shared by and between the modules of which the modular energy system is constructed. An Ethernet switch domain 6013 can be derived from the primary power domain 6009, for example. The Ethernet switch power domain 6013 is segregated into a separate power domain, which is configured to power Ethernet switches within each of the modules in the stack configuration, so that the primary communications interface 6040 will remain alive when local power to a module is removed. In at least one example, the primary communication interface 6040 comprises a 1000BASE-T Ethernet network, where each module represents a node on the network, and each module downstream from the header module 6002 contains a 3-port Ethernet switch for routing traffic to the local module or passing the data up or downstream as appropriate.

Furthermore, in certain examples, the modular energy system 6000 includes secondary, low speed, communication interface between modules for critical, power related functions including module power sequencing and module power status. The secondary communications interface can, for example, be a multi-drop Local Interconnect Network (LIN), where the header module is the master and all downstream modules are slaves.

In various aspects, as illustrated in FIG. 20, a standby power domain 6010 is a separate output from the AC/DC power supply 6003 that is always live when the supply is connected to mains power 6020. The standby power domain 6010 is used by all the modules in the system to power circuitry for a mitigated communications interface, and to control the local power to each module. Further, the standby power domain 6010 is configured to provide power to circuitry that is critical in a standby mode such as, for example, on/off command detection, status LEDs, secondary communication bus, etc.

In various aspects, as illustrated in FIG. 20, the individual surgical modules 6004 lack independent power supplies and, as such, rely on the header module 6002 to supply power in the stack configuration. Only the header module 6002 is directly connected to the mains power 6020. The surgical modules 6004 lack direct connections to the mains power 6020, and can receive power only in the stack configuration. This arrangement improves the safety of the individual surgical modules 6004, and reduces the overall footprint of the modular energy system 6000. This arrangement further reduces the number of cords required for proper operation of the modular energy system 6000, which can reduce clutter and footprint in the operating room.

Accordingly, a surgical instrument connected to surgical modules 6004 of a modular energy system 6000, in the stack configuration, receives therapeutic energy for tissue treatment that is generated by the surgical module 6004 from power delivered to the surgical module 6004 from the AC/DC power supply 6003 of the header module 6002.

In at least one example, while a header module 6002 is assembled in a stack configuration with a first surgical module 6004', energy can flow from the AC/DC power supply 6003 to the first surgical module 6004'. Further, while a header module 6002 is assembled in a stack configuration with a first surgical module 6004' (connected to the header module 6002) and a second surgical module 6004" (connected to the first surgical module 6004'), energy can flow from the AC/DC power supply 6003 to the second surgical module 6004" through the first surgical module 6004'.

The energy generated by the AC/DC power supply 6003 of the header module 6002 is transmitted through a segmented power backplane 6008 defined through the modular energy system 6000. In the example of FIG. 20, the header module 6002 houses a power backplane segment 6008', the first surgical module 6004' houses a power backplane segment 6008", and the second surgical module 6004" houses a power backplane segment 6008"'. The power backplane segment 6008' is detachably coupled to the power backplane segment 6008" in the stack configuration. Further, the power backplane 6008" is detachably coupled to the power backplane segment 6008"' in the stack configuration. Accordingly, energy flows from the AC/DC power supply 6003 to the power backplane segment 6008', then to the power backplane segment 6008", and then to the power backplane segment 6008"'.

In the example of FIG. 20, the power backplane segment 6008' is detachably connected to the power backplane segment 6008" via pass-through hub connectors 6005, 6006 in the stack configuration. Further, the power backplane segment 6008" is detachably connected to the power backplane segment 6008''' via pass-through hub connectors 6025, 6056 in the stack configuration. In certain instances, removing a surgical module from the stack configuration severs its connection to the power supply 6003. For example, separating the second surgical module 6004'' from the first surgical module 6004' disconnects the power backplane segment 6008''' from the power backplane segment 6008''. However, the connection between the power backplane segment 6008'' and the power backplane segment 6008''' remains intact as long as the header module 6002 and the first surgical module 6004' remain in the stack configuration. Accordingly, energy can still flow to the first surgical module 6004' after disconnecting the second surgical module 6004'' through the connection between the header module 6002 and the first surgical module 6004'. Separating connected modules can be achieved, in certain instances, by simply pulling the surgical modules 6004 apart.

In the example of FIG. 20, each of the modules 6002, 6004 includes a mitigated module control 6023. The mitigated module controls 6023 are coupled to corresponding local power regulation modules 6024 that are configured to regulate power based on input from the mitigated module controls 6023. In certain aspects, the mitigated module controls 6023 allow the header module 6002 to independently control the local power regulation modules 6024.

The modular energy system 6000 further includes a mitigated communications interface 6021 that includes a segmented communication backplane 6027 extending between the mitigated module controls 6023. The segmented communication backplane 6027 is similar in many respects to the segmented power backplane 6008. Mitigated Communication between the mitigated module controls 6023 of the header module 6002 and the surgical modules 6004 can be achieved through the segmented communication backplane 6027 defined through the modular energy system 6000. In the example of FIG. 20, the header module 6002 houses a communication backplane segment 6027', the first surgical module 6004' houses a communication backplane segment 6027'', and the second surgical module 6004'' houses a communication backplane segment 6027'''. The communication backplane segment 6027' is detachably coupled to the communication backplane segment 6027'' in the stack configuration via the pass-through hub connectors 6005, 6006. Further, the communication backplane 6027'' is detachably coupled to the communication backplane segment 6027'' in the stack configuration via the pass-through hub connectors 6025, 6026.

Although the example of FIG. 20 depicts a modular energy system 6000 includes a header module 6002 and two surgical modules 6004' 6004'', this is not limiting. Modular energy systems with more or less surgical modules are contemplated by the present disclosure. In some aspects, the modular energy system 6000 includes other modules such as, for example, the communications module 3032 (FIG. 15). In some aspects, the header module 6502 supports a display screen such as, for example, the display 2006 (FIG. 7A) that renders a GUI such as, for example, the GUI 2008 for relaying information regarding the modules connected to the header module 6002. As described in greater detail in connection with the example of FIG. 15, in some aspects, the GUI 2008 of the display screen 2006 can provide a consolidated point of control all of the modules making up the particular configuration of a modular energy system.

FIG. 21 depicts a simplified schematic diagram of the modular energy system 6000, which illustrates a primary communications interface 6040 between the header module 6002 and the surgical modules 6004. The primary communications interface 6040 communicably connects module processors 6041, 6041', 6041'' of the header module 6002 and the surgical modules 6004. Commands generated by the module processor 6041 of the header module are transmitted downstream to a desired functional surgical module via the primary communications interface 6040. In certain instances, the primary communications interface 6040 is configured to establish a two-way communication pathway between neighboring modules. In other instances, the primary communications interface 6040 is configured to establish a one-way communication pathway between neighboring modules.

Furthermore, the primary communications interface 6040 includes a segmented communication backplane 6031, which is similar in many respects to the segmented power backplane 6008. Communication between the header module 6002 and the surgical modules 6004 can be achieved through the segmented communication backplane 6031 defined through the modular energy system 6000. In the example of FIG. 21, the header module 6002 houses a communication backplane segment 6031', the first surgical module 6004' houses a communication backplane segment 6031'', and the second surgical module 6004'' houses a communication backplane segment 6031'''. The communication backplane segment 6031' is detachably coupled to the communication backplane segment 6031'' in the stack configuration via the pass-through hub connectors 6005, 6006. Further, the communication backplane 6031'' is detachably coupled to the communication backplane segment 6031'' in the stack configuration via the pass-through hub connectors 6025, 6026.

In at least one example, as illustrated in FIG. 21, the primary communications interface 6040 is implemented using the DDS framework running on a Gigabit Ethernet interface. The module processors 6041, 6041', 6041'' are connected to Gigabit Ethernet Phy 6044, and Gigabit Ethernet Switches 6042', 6042''. In the example of FIG. 21, the segmented communication backplane 6031 connects the Gigabit Ethernet Phy 6044 and the Gigabit Ethernet Switches 6042 of the neighboring modules.

In various aspects, as illustrated in FIG. 21, the header module 6002 includes a separate Gigabit Ethernet Phy 6045 for an external communications interface 6043 with the processor module 6041 of the header module 6002. In at least one example, the processor module 6041 of the header module 6002 handles firewalls and information routing.

Referring to FIG. 20, the AC/DC power supply 6003 may provide an AC Status signal 6011 that indicates a loss of AC power supplied by the AC/DC power supply 6003. The AC status signal 6011 can be provided to all the modules of the modular energy system 6000 via the segmented power backplane 6008 to allow each module as much time as possible for a graceful shutdown, before primary output power is lost. The AC status signal 6011 is received by the module specific circuits 6013, 6014, 6015, for example. In various examples, the system power control 6017 can be configured to detect AC power loss. In at least one example, the AC power loss is detected via one or more suitable sensors.

Referring to FIGS. 20 and 21, to ensure that a local power failure in one of the modules of the modular energy system 6000 does not disable the entire power bus, the primary power input to all modules can be fused or a similar method of current limiting can be used (e-fuse, circuit breaker, etc.). Further, Ethernet switch power is segregated into a separate power domain 6013 so that the primary communications interface 6040 remains alive when local power to a module is removed. In other words, primary power can be removed and/or diverted from a surgical module without losing its ability to communicate with other surgical modules 6004 and/or the header module 6002.

Mitigated Interface for Energy Footswitch Activation

Having described a general implementation the header and modules of modular energy systems 2000, 3000, 6000, the disclosure now turns to describe various aspects of other modular energy systems. The other modular energy systems are substantially similar to the modular energy system 2000, the modular energy system 3000, and/or the modular energy system 6000. For the sake of brevity, various details of the other modular energy systems being described in the following sections, which are similar to the modular energy system 2000, the modular energy system 3000, and/or the modular energy system 6000, are not repeated herein. Any aspect of the other modular energy systems described below can be brought into the modular energy system 2000, the modular energy system 3000, or the modular energy system 6000.

In general terms throughout the present disclosure, coupled refers to wireless or wired connections between two components. For illustrative purposes and not limitations, the accessory described in this context is a footswitch that is used to activate energy to an electrosurgical/ultrasonic instrument. As used herein, electrosurgical/ultrasonic instrument comprises any one of an electrosurgical instrument that is either monopolar or bipolar, an ultrasonic instrument, or an instrument that employs a combination of electrosurgical and ultrasonic energy, connected to the energy module 2004, 3004, 6004 of the modular energy system 2000, 3000, 6000. Accordingly, in one aspect, the accessory may comprise one or more than one footswitch configured to activate an electrosurgical/ultrasonic instrument by communicating switch states to the modular energy module 2000, 3000, 6000. In one aspect, the mitigated interface detects the state of each coupled footswitch, or other accessory, as well as the type of footswitch, or other accessory, that is coupled to the modular energy system 2000, 3000, 6000. In another aspect, the present disclosure provides a robust wireless mesh communication network to improve the reliability of wireless communications between accessories and the modular energy system 2000, 3000, 6000 in an operating room (OR) environment.

In one aspect, the present disclosure provides a modular energy system 2000, 3000, 6004 comprising a header module 2002, 3002, 6002 and at least one energy module 2004, 3004, 6004 with support for multiple footswitches and footswitch types to control the activation of electrosurgical/ ultrasonic instruments connected to the energy module 2004, 3004, 6004. In one aspect, to accommodate support for multiple footswitches and footswitch types, an isolated interface is disposed between a host controller in the header module 2002, 3002, 6002 and the footswitch ports into which the footswitches are coupled to the header module 2002, 3002, 6002. The isolated interface detects the state of the connected footswitch as well as the type of connected footswitch. The isolated interface comprises isolation circuitry, which is typically physically large and costly. Therefore, it is desirable to minimize the number of discrete signals crossing the isolation boundary to minimize the number of isolation circuitry required in a given application. It is also desirable to provide mitigation techniques at the isolated interface to minimize the probability that an energy device such as an electrosurgical/ultrasonic instrument receives an uncommanded erroneous activation signal from the accessory.

Figure 22:
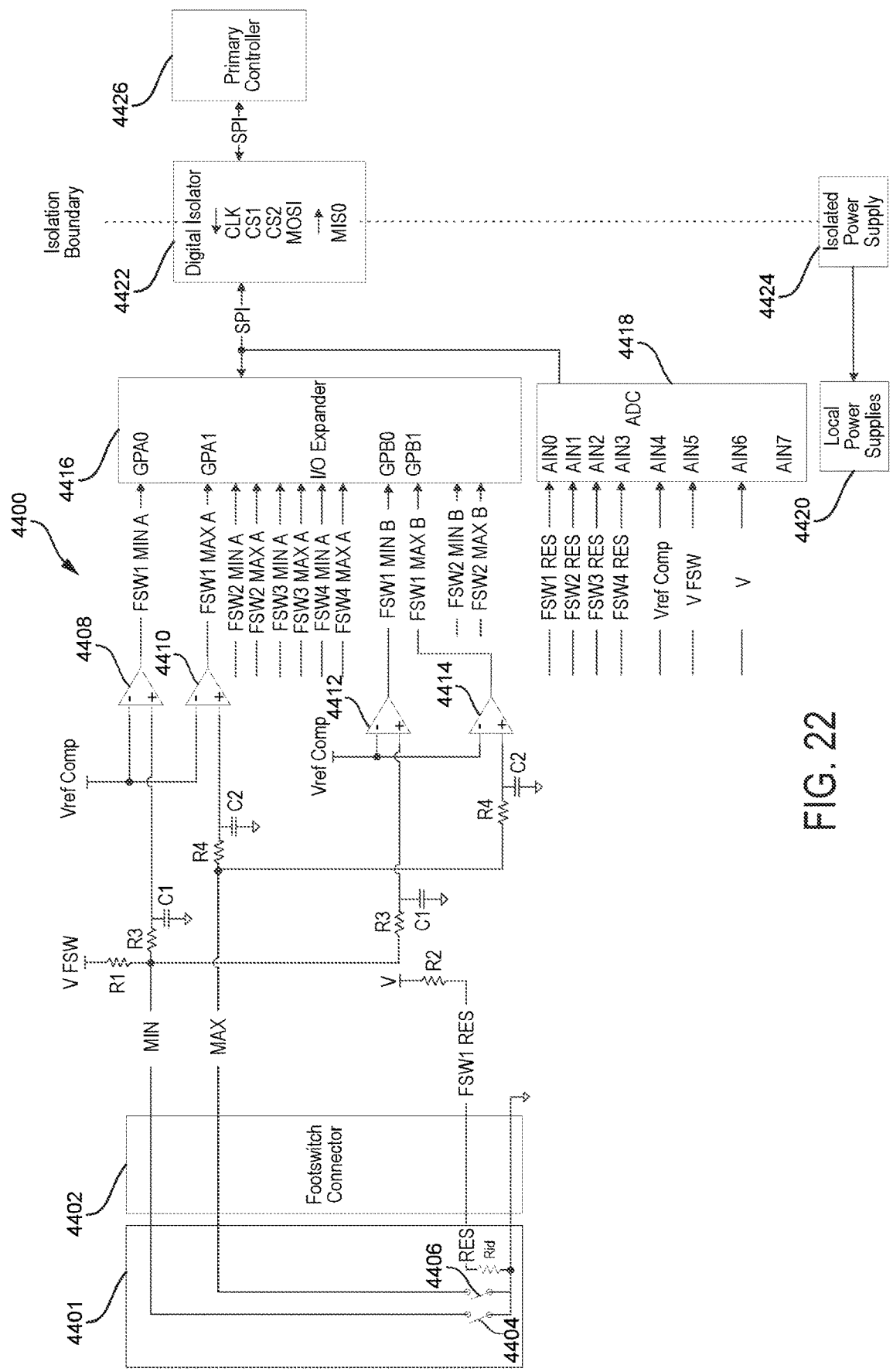
FIG. 22 is a schematic diagram of an isolated footswitch interface circuit to support and mitigate footswitch activation for multiple footswitches and types of footswitches, in accordance with at least one aspect of the present disclosure.

FIG. 22 is a schematic diagram of an isolated switch interface circuit 4400 to support and mitigate footswitch activation for multiple footswitches and types of footswitches, in accordance with at least one aspect of the present disclosure. The isolated switch interface circuit 4400 comprises a footswitch 4401 coupled to a footswitch connector 4402. In one aspect, the footswitch 4401 comprises a minimum (MIN) switch 4404 and a maximum (MAX) switch 4406 output. A footswitch identification circuit comprising, for example, a resistor "R id" is used to identify the type of footswitch 4401 coupled to the footswitch connector 4402. It will be appreciated that, although the present examples is directed to a footswitch, the isolated switch interface circuit 4400 may be adapted for any switch used to control activation or deactivation of a surgical instrument coupled to the energy module 2004 of a modular energy system 2000.

The MIN switch 4404 is coupled through the footswitch connector 4402 to a first footswitch detection circuit comprising a first comparator 4408. The MAX switch 4406 is coupled through the footswitch connector 4402 to a second comparator 4410. A reference voltage Vref Comp is applied to each of the first and second comparators 4408, 4410. The voltage signals generated by closing or opening the MIN and MAX switches 4404, 4406 are compared to the reference voltage Vref Comp at the respective inputs of the first and second comparators 4408, 4410. The output FSW1 MIN A of the first comparator 4408 and the output FSW1 MAX A of the second comparator 4410 are applied to an input/output (I/O) expander circuit 4416. The FSW1 RES voltage signal is used to identify the type of footswitch 4401 coupled to the footswitch connector 4402 is applied to an input of an analog-to-digital converter (ADC) circuit 4418.

The MIN switch 4404 is also coupled through the footswitch connector 4402 to a duplicate footswitch detection circuit comprising a third comparator 4412. The MAX switch 4406 is also coupled through the footswitch connector 4402 to a duplicate footswitch detection circuitry comprising a fourth comparator 4414. A reference voltage Vref Comp is applied to each of the third and fourth comparators 4412, 4414. The voltage signals generated by closing or opening the MIN and MAX switches 4404, 4406 are compared to the reference voltage Vref Comp at the respective inputs of the third and fourth comparators 4412, 4414. The output FSW1 MIN B of the first comparator 4412 and the output FSW1 MAX B are applied to the I/O expander circuit 4416. The duplicate footswitch detection circuitry mitigates energy footswitch activation to a surgical instrument coupled to the energy module 2004, 3004, 6004. It will be appreciated that the duplicate footswitch detection circuitry mitigates against potential failures in the detection circuitry.

The output of the I/O expander circuit 4416 is connected to a digital isolator circuit 4422 and to a primary controller 4426 over a serial peripheral interface (SPI), e.g., single digital serial communication bus. The primary controller 4426 comprises a processor. The primary controller 4426 compares the outputs of the first and second footswitch detection circuits and either activates or deactivates energy to the surgical instrument coupled to the energy module 2004 based on the results of the comparison. For example, the primary controller 4426 will activate or deactivate if the outputs of the first and second footswitch detection circuits match. If there is a mismatch between the outputs of the first and second footswitch detection circuits, the primary controller 4426 will deactivate energy to the surgical instrument. In the instance where the first and second footswitch detection circuits each include a single comparator 4408 and a duplicate comparator 4412, the primary controller 4426 compares the outputs of the single comparator 4408 and the duplicate comparator 4412.

In the instance where the first and second footswitch detection circuits each include multiple comparators such as a first and second comparator 4408, 4410 and first and second duplicate comparators 4412, 4414, the primary controller 4426 compares the outputs of the first comparator 4408 with the first duplicate comparator 4412 and compares the output of the second comparator 4410 with the second duplicate comparator 4414. This process may be scaled up to a predetermined number of footswitches and corresponding number of comparators and duplicate comparators. In this manner, the primary controller 4426 can mitigate the risk of any given footswitch signal by comparing the outputs of the primary comparators to the corresponding duplicate comparators.

As shown in FIG. 22, the digital isolator circuit 4422 defines an isolation boundary between the primary controller 4426 and the isolated switch interface circuit 4400. An isolated power supply 4424 supplies power to the local power supplies 4420 of the isolated switch interface circuit 4400.

Still with reference to FIG. 22, additional footswitches FSW2, FSW3, FSW4, and others, can be added to the isolated switch interface circuit 4400. These additional footswitches FSW2, FSW3, FSW4, and others, are coupled to the I/O expander circuit 4416 and to the primary controller 4426 over the SPI bus and through the digital isolator circuit 4422. The ID resistor values FSW2 RES, FSW3 RES, FSW4 RES, and others, identify the type of footswitches FSW2, FSW3, FSW4, and others. In one aspect, the ID resistor values FSW1 RES, FSW2 RES, FSW3 RES, FSW4 RES are applied to the ADC circuit 4418 in the form of voltages. In other implementations, currents or other parameters may be applied to the ADC circuit 4418 to identify the type of footswitches. The ADC circuit 4418 is coupled to the primary controller 4426 over the SPI bus and through the digital isolator circuit 4422. The signal Vref_Comp is provided as input to the ADC circuit 4418. The Vref_Comp signal is provided to the input of the ADC circuit 4418 such that the primary controller 4426 can perform a self-test of the comparator reference voltage Vref_Comp.

The disclosed I/O expander circuit 4416 and the ADC circuit 4418 are connected on the single SPI bus. The ADC circuit 4418 monitors a resistor value FSW1 RES integrated into each attached footswitch 4401 for detecting unique footswitch types. The I/O expander circuit 4416 monitors the MIN state and the MAX state of each footswitch 4401. Employing the I/O expander circuit 4416 with greater than or equal to twice the number of required I/O, the footswitch states MIN, MAX can be mitigated by duplicating the detection circuitry. Accordingly, the isolated switch interface circuit 4400 detects the switch state of each connected footswitch 4401 as well as the type of footswitch 4401 connected. The isolated switch interface circuit 4400 minimizes the number of discrete signals crossing the isolation boundary as isolation circuitry is typically physically large and costly. Further, the isolated switch interface circuit 4400 provides mitigation techniques on the interface to minimize the probability that an energy device receives an uncommanded activation. Accordingly, using a single digital, serial communication bus SPI for bridging across the isolation boundary minimizes the number of signals required by the isolated switch interface circuit 4400. This technique minimizes the number of discrete signals crossing the isolation boundary to minimize the isolation circuitry required in a given application and simplifies the implementation.

In one aspect, the present disclosure provides a method of mitigating erroneous outputs from an isolated footswitch interface circuit 4400 for a modular energy system 2000. The method comprises receiving, at a first input of a first comparator 4408, a state of a first switch 4404 of a first footswitch 4401 coupled to the first input of the first comparator 4408 and a reference voltage Vref_Comp coupled to a second input of the first comparator 4408. The method comprises, receiving, at a first input of a first duplicate comparator 4412, the state of the first switch 4404 coupled to the first input of the first duplicate comparator 4412 and the reference voltage Vref_Comp coupled to a second input of the first duplicate comparator 4412. The method comprises comparing, by the controller 4426 coupled to the outputs of the first comparator 4408 and the first duplicate comparator 4412, the output of the first comparator 4408 with the output of the first duplicate comparator 4412. The method comprises determining, by the controller 4426, activation or deactivation of a surgical instrument coupled to the controller 4426 based on the comparison.

The method further comprises receiving, by an analog to digital converter 4418 (ADC) coupled to the controller 4426, a first footswitch identification signal FSW1 RES and identifying, by the controller 4426, a type of the footswitch 4401 based on the first switch identification signal FSW1 RES. In another aspect, the method further comprises the primary controller 4426 measuring the "Vref_Comp" voltage and determining that it is within its expected range by measuring the voltage at the ADC 4418 input.

The method further comprises receiving, at a first input of a second comparator 4410, a state of a second switch 4406 of the first footswitch 4401 coupled to the first input of the second comparator 4410 and a reference voltage Vref_Comp coupled to a second input of the second comparator 4410. The method comprises, receiving, at a first input of a second duplicate comparator 4414, the state of the second switch 4406 coupled to the first input of the second duplicate comparator 4414 and the reference voltage Vref_Comp coupled to a second input of the second duplicate comparator 4414. The method comprises comparing, by the controller 4426 coupled to outputs of the second comparator 4410 and the second duplicate comparator 4414, the output of the second comparator 4410 with the output of the second duplicate comparator 4414.

The method further comprises determining, by the controller 4426, activation or deactivation of a surgical instrument coupled to the controller 4426 based on the comparison. In one aspect, the method comprises receiving, by the ADC 4418, a comparator reference voltage Vref_Comp and measuring, by the controller 4426, the comparator reference voltage Vref_Comp applied to the ADC 4418. The method further comprises determining, by the controller 4426, that the comparator reference voltage Vref_Comp is within predetermined limits and enabling, by the controller 4426, activation of the surgical instrument in the instance that the comparator reference voltage Vref_Comp is within the predetermined limits and disabling, by the controller 4426, activation of the surgical instrument in the instance that the comparator reference voltage Vref_Comp is not within the predetermined limits.

In other aspects, the mitigation method further comprises mitigating the circuitry by measuring the voltage rails V and detecting an error if these voltages V are outside an expected range. In one aspect, the ADC 4418 also may receive at its input one or more of the power supply, V and V FSW, for example, and reference voltages, Vref_Comp, for example, used by the detection circuitry. In another aspect, the ADC 4418 also may receive at its input one or more of the power supply and reference voltages used by the detection circuitry scaled by a scaling circuitry. Accordingly, in various aspects, the method further comprises receiving, at an input to the ADC 4418, one or more of the power supply V and V FSW and reference voltages Vref_Comp used by the detection circuitry, or one or more of the power supply and reference voltages used by the detection circuitry scaled by a scaling circuitry. The method further comprises comparing, by the controller 4426, a measurement of the power supply V and V FSW and reference voltages Vref_Comp to an expected range to determine proper operation of the voltage supply circuitries.

Robust Wireless Accessory Communication

Wireless communication can potentially be unreliable in an operating room (OR) environment, due to various sources of electromagnetic interference or other sources of interference. For many applications (such as footswitch-activation), a robust method of communicating wirelessly is needed. The present disclosure provides circuits and associated methods for robust wireless accessory communication in an OR environment.

Figure 23:
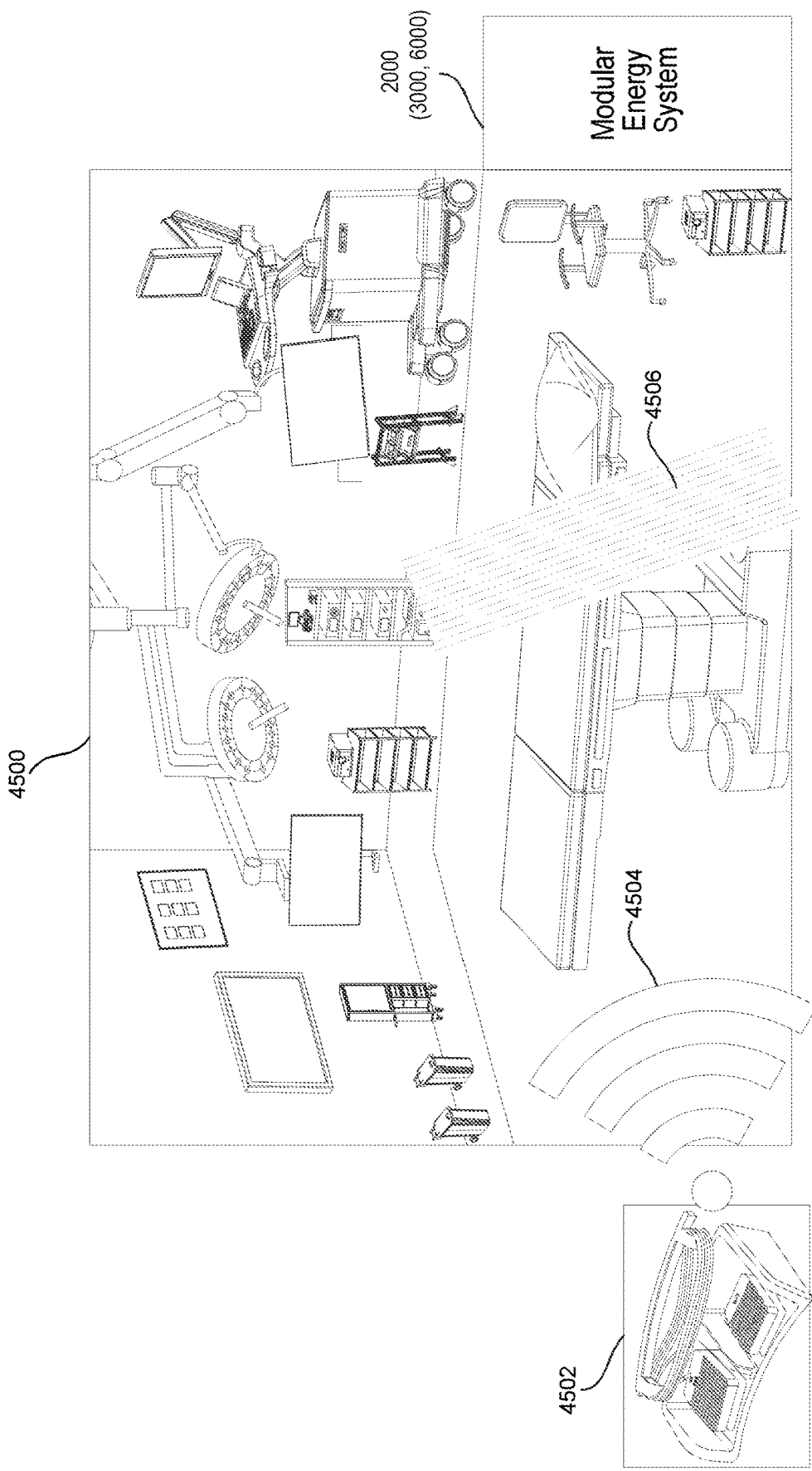
FIG. 23 shows an operating room (OR) with an accessory communicating wirelessly to a modular energy system.

FIG. 23 shows an operating room 4500 (OR) with an accessory communicating wirelessly to a modular energy system 2000, 3000, 6000. In example illustrated in FIG. 23, the accessory is a wireless footswitch 4502 in wireless communication with the modular energy system 2000, 3000, 6000. Interference 4506 in the OR 4500 can block the wireless signals 4504 and may impact the reliability of related communications. For example, wireless signals 4504 transmitted by the footswitch 4502 may not reach the modular energy system 2000, 3000, 6000 to activate or deactivate an electrosurgical/ultrasonic instrument used in an OR procedure. In other aspects, the accessory may comprise multiple footswitches or other devices coupled to the modular energy system 2000, 3000, 6000.

FIG. 24 is a schematic representation of a wireless mesh network 4510, in accordance with at least one aspect of the present disclosure. Those skilled in the art will appreciate that a wireless mesh network (WMN) may be any communications network made up of radio nodes organized in a mesh topology. The WMN can also be implemented in the form of a wireless ad hoc network. A mesh refers to rich interconnection among devices or nodes 1-11. Wireless mesh networks may comprise of mesh clients, mesh routers, and gateways. This differs from typical point-to-point or "star" topologies in that any "node" 1-11 on the mesh 4510 can communicate with one, many, or all other nodes 1-11 on the mesh 4510. In one aspect, the wireless mesh network 4510 may be implemented as a Bluetooth Mesh, a relatively new wireless standard that supports communications in a WMN. Further, nodes 1-11 can "forward" messages to other nodes 1-11 to allow for long-range communication, or for redundant communication paths.

FIG. 25 is a bock diagram of a modular energy system 2000, 3000, 6000 comprising multiple radios 4512, 4516, in accordance with at least one aspect of the present disclosure. Each radio 4512, 4516 is configured to transmit or receive unique wireless signals 4514, 4518, respectively communicated over the wireless mesh network 4510 (FIG. 24).

FIG. 26 is a diagram of a footswitch 4520 comprising multiple radios 4522, 4526, in accordance with at least aspect of the present disclosure. Each radio 4522, 4526 is configured to transmit or receive unique wireless signals 4524, 4528 communicated over the wireless mesh network 4510 (FIG. 24).

With reference to FIGS. 23-26, each accessory in the OR 4500, such as the footswitch 4520 may comprise multiple radios 4522, 4526 to transmit or receive wireless signals 4524, 4528 to communicate with the modular energy system 2000, 3000, 6000 over the wireless mesh network 4510. Each footswitch 4520 radio 4522, 4526 determines the state of the footswitch 4520. Each modular energy system 2000, 3000, 6000 radio 4512, 4516 and footswitch 4520 radio 4522, 4526 defines one or more than one node 1-11 defined by the wireless mesh network 4510. Thus, in the instance of a radio 4512 failure, other radios 4516, 4522, 4526 would be operational in the wireless mesh network 4510. It will appreciated that the modular energy system 2000, 3000, 6000 and the footswitch 4520 may comprise a single radio. Single radio implementation would still provide a benefit to the wireless mesh network 4510 topology to overcome interference 4506 in the OR 4500.

Figure 27:
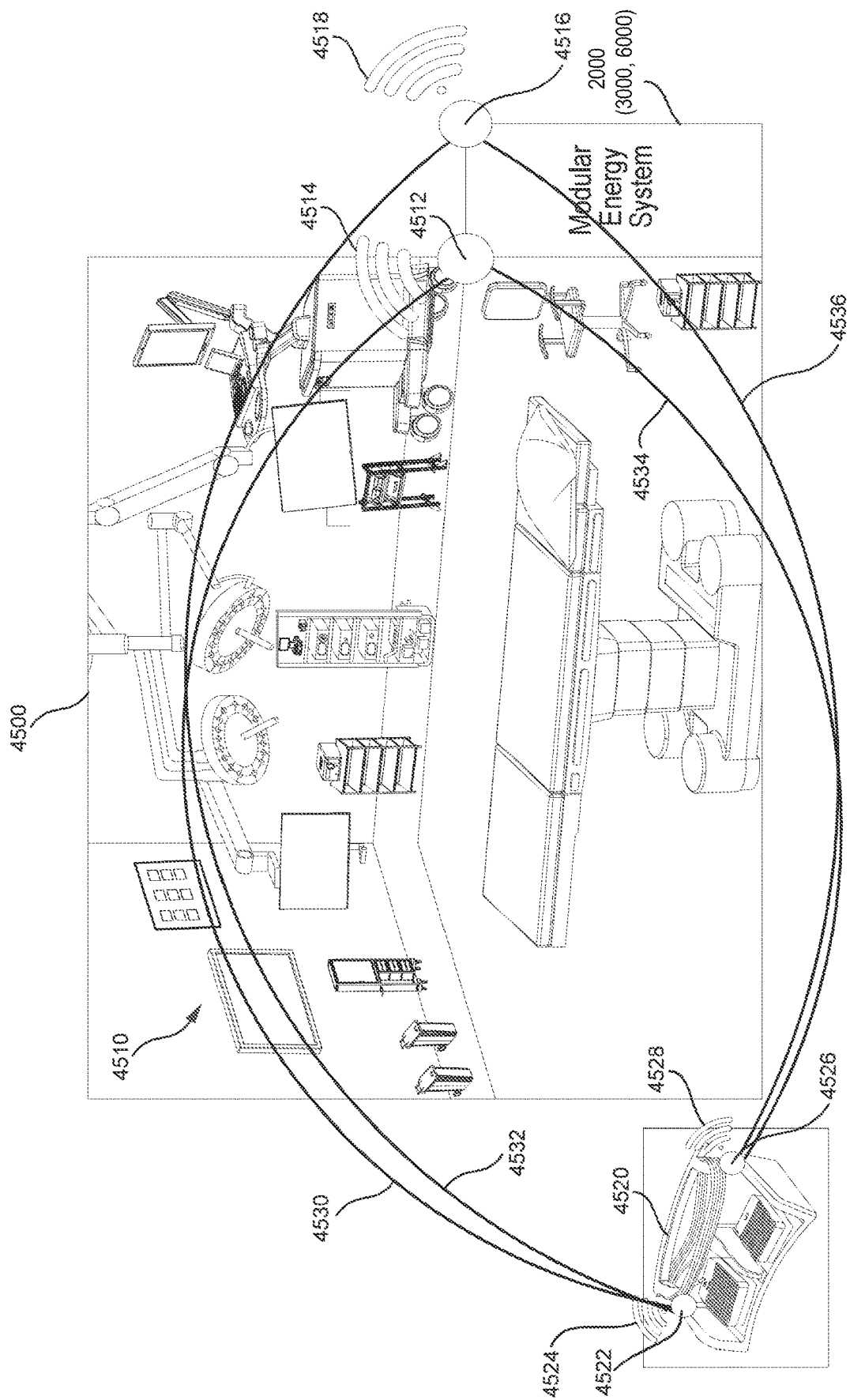
FIG. 27 shows an OR equipped with an accessory communicating wirelessly to a modular energy system over a wireless mesh network implemented by multiple radios, in accordance with at least one aspect of the present disclosure.

FIG. 27 shows an OR 4500 equipped with an accessory communicating wirelessly to a modular energy system 2000, 3000, 6000 over a wireless mesh network 4510 implemented by multiple radios 4512, 4516, 4522, 4526, in accordance with at least one aspect of the present disclosure. In example illustrated in FIG. 27, the accessory is a wireless footswitch 4502 in wireless communication with the modular energy system 2000, 3000, 6000. The wireless mesh network 4510 (e.g., Bluetooth Mesh) comprising multiple nodes 1-11, for example, is implemented with multiple radios 4512, 4516, 4522, 4526, among others, in the modular energy system 2000, 3000, 6000 and footswitch 4530 accessory. The wireless mesh network 4510 topology facilitates the implementation of redundant wireless communication paths 4530, 4532, 4534, 4536, to form a robust wireless accessory communication network. Thus, if a wireless communication path 4530 were to fail, there are three other wireless communication paths 4532, 4534, 4536 still available for reliable communication.

In the example implementation illustrated in FIGS. 25-27, the wireless footswitch 4520 comprises two wireless radios 4524, 4526 defining two mesh nodes, e.g., Bluetooth Mesh nodes, each independently reading the states of the footswitch 4520. This provides full redundancy at the footswitch 4520 level. Further, the modular energy system 2000, 3000, 6000 comprises two wireless radio 4512, 4516 defining two mesh nodes, e.g., Bluetooth Mesh nodes, creating redundancy at the modular energy system 2000, 3000, 6000 level as well. The radios 4512, 4516, 4522, 4526 (e.g., nodes) create redundant wireless communication paths 4530, 4532, 4534, 4536 between the footswitch 4520 and the modular energy system 2000, 3000, 6000.

Figure 28:
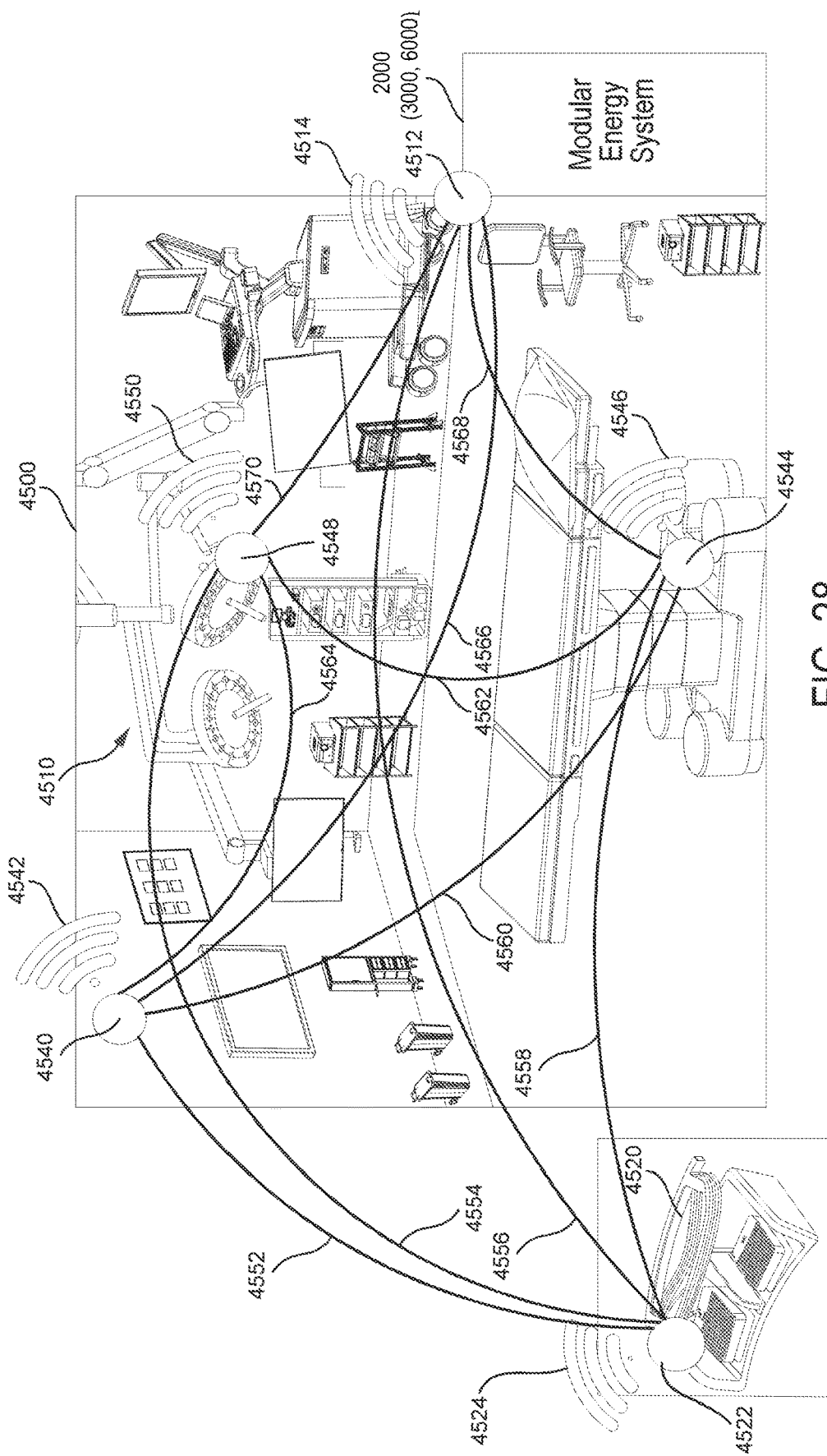
FIG. 28 is an operating room (OR) configured with additional "repeater" nodes optionally be placed around the OR environment to provide a robust wireless mesh network, in accordance with at least one aspect of the present disclosure.

FIG. 28 is an operating room 4500 (OR) configured with additional "repeater" nodes optionally be placed around the OR environment to provide a robust wireless mesh network 4510, in accordance with at least one aspect of the present disclosure. In the example shown in FIG. 28, the footswitch 4520 comprises a single radio 4522 to transmit and receive wireless signals 4525 and defining a wireless node in the wireless mesh network 4510. The modular energy system 2000, 3000, 6000 also comprises a single radio 4512 to transmit and receive wireless signals 4514 and defining another wireless node in the wireless mesh network 4510. To add redundancy to and improve robustness of the wireless mesh network 4510 in the OR 4500, additional nodes may be located in the OR 4550, e.g., underneath a table, on ceiling, etc. These additional nodes 4540, 4544, 4548 each can receive and transmits wireless signals 4542, 4546, 4550, respectively, over redundant wireless communication paths 4552, 4554, 4556, 4558, 4560, 4562, 4564, 4566, 4568, 4570 to forward messages to other nodes, creating redundant nodes in the wireless mesh network 4510 between the footswitch 4520 and the modular energy system 2000, 3000, 6000. The redundant wireless communication paths 4552-4570 result in a redundant wireless mesh network 4510 that is robust to single (or multiple) fault conditions.

The wireless mesh network 4510 shown in FIG. 28 increases the maximum distance between the footswitch 4520 and the modular energy system 2000 and increases redundancy in communication paths 4552, 4554, 4556, 4558, 4560, 4562, 4564, 4566, 4568, 4570. Although the example shown in FIG. 28 shows only one active radio 4522 in the footswitch 4520 and one active radio 4512 in the modular energy system 2000, 3000, 6000, this can be expanded to multiple radios per footswitch 4520 and modular energy system 2000, 3000, 6000.

Figure 29:
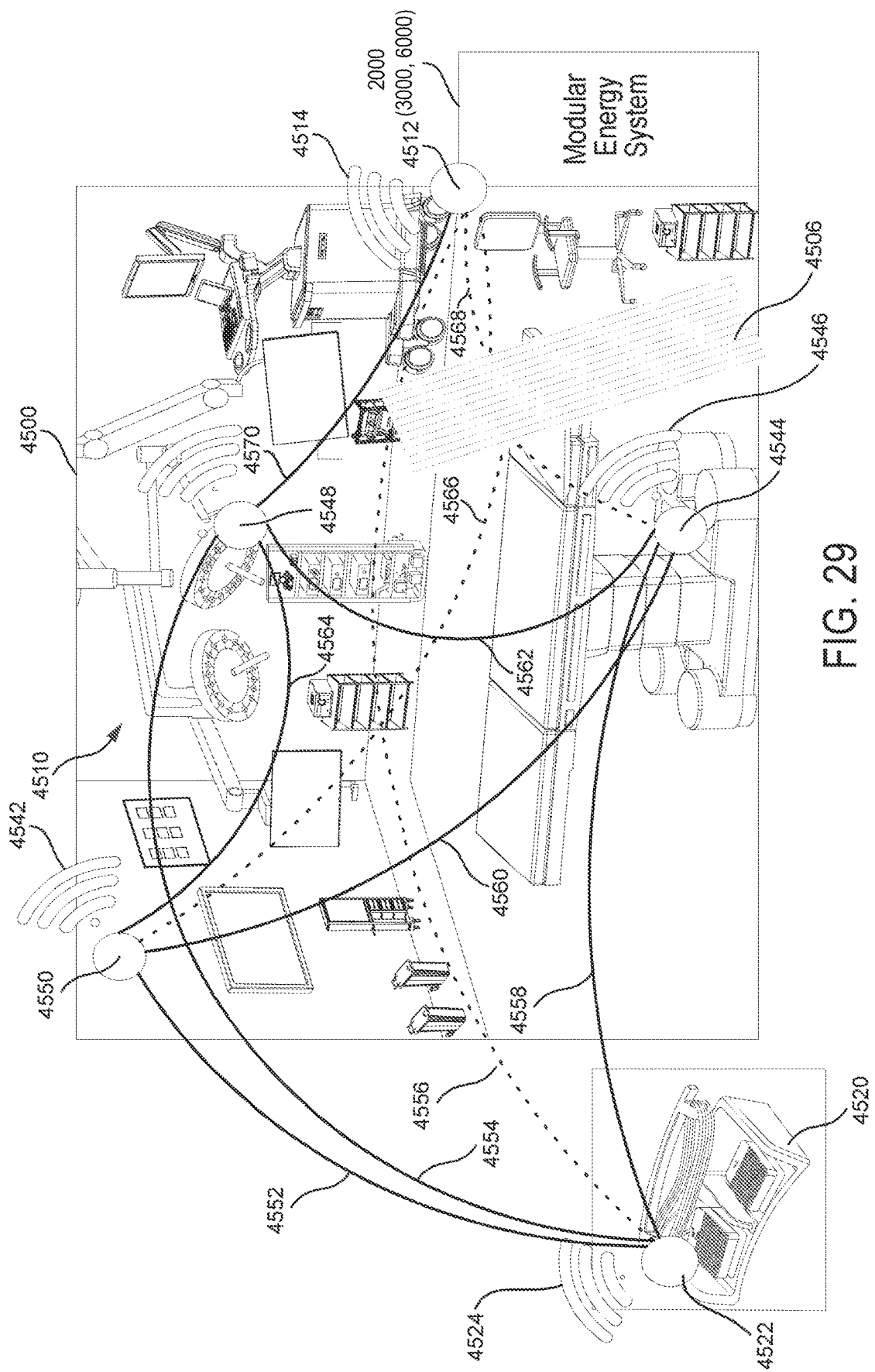
FIG. 29 shows the operating room (OR) shown in FIG. 28 with interference blocking some of the communication paths and communications routed to other nodes in the wireless mesh network, in accordance with at least one aspect of the present disclosure.

FIG. 29 shows the OR 4500 shown in FIG. 28 with interference 4506 blocking some of the communication paths 4556, 4566, 4568 and communications routed to other nodes in the wireless mesh network 4510, in accordance with at least one aspect of the present disclosure. Despite this interference 4506, the communication can occur by going around the interference 4506 along other functional communication paths 4552, 4554, 4558, 4560, 4562, 4564, 4570, for example.

The wireless mesh network 4510 described with reference to FIGS. 24-J8 may be expandable to many accessories, such as the footswitch 4520, for example, where each additional accessory comprises radios that acts as nodes to strengthen the network. The wireless mesh network 4510 provides a robust wireless communication system that is tolerant to external interference and long distances. In other aspects, Bluetooth wireless modules that may be employed to implement the wireless mesh network are advantageous due to their relatively low cost and ease of installation. Further, the wireless mesh network 4510 provides security to support public/private key authentication and encryption, permission levels at network, node, and application levels, and can be used in low-power (battery powered) situations.

EXAMPLES

Various aspects of the subject matter described herein are set out in the following numbered examples.

Example 1. An isolated interface circuit for a modular energy system, the isolated interface circuit comprising: a comparator comprising a first input configured to couple to a switch, a second input configured to couple to a reference voltage, and an output; a duplicate comparator comprising a first input configured to couple to the switch, a second input configured to couple to the reference voltage, and an output; an expander circuit comprising at least two inputs, wherein the output of the comparator is coupled to one of the at least two inputs of the expander circuit, and wherein the output of the duplicate comparator is coupled to other of the at least two inputs of the expander circuit, the expander circuit comprising an output; an isolator circuit comprising an input and an output, wherein the input is coupled to the output of the expander circuit; and a controller coupled to the output of the isolator circuit, wherein the controller is configured to: compare the output of the comparator with the output of the duplicate comparator; and determine activation or deactivation of a surgical instrument coupled to the controller based on the comparison.

Example 2. The isolated switch interface circuit of Example 1, comprising: an analog to digital converter (ADC) coupled to the controller through the isolator circuit; and a switch identification circuit coupled to the ADC, wherein the switch identification circuit is configured to identify a type of switch coupled to the comparator and duplicate comparator.

Example 3. The isolated interface circuit of any one or more of Examples 1 through 2, wherein the isolator circuit comprises a digital isolator circuit.

Example 4. The isolated interface circuit of any one or more of Examples 1 through 3, wherein the comparator and duplicate comparator are configured to couple to multiple switches, the comparator comprising multiple comparators configured to couple to each of the multiple switches, and the duplicate comparator comprising multiple comparators configured to couple to each of the multiple switches; and wherein the controller is configured to compare the outputs of each of the multiple comparators with the corresponding outputs of each of the duplicate comparators.

Example 5. The isolated interface circuit of any one or more of Examples 1 through 4, wherein the comparator and duplicate comparator are configured to couple to a footswitch.

Example 6. The isolated interface circuit of any one or more of Examples 1 through 5, wherein the output of the isolator circuit is a digital serial communication bus.

Example 7. An isolated interface circuit for a modular energy system, the isolated interface circuit comprising: a first comparator comprising a first input configured to couple to a first switch, a second input configured to couple to a reference voltage, and an output; a second comparator comprising a first input configured to couple to a second switch, a second input configured to couple to the reference voltage, and an output; a first duplicate comparator comprising a first input configured to couple to the first switch, a second input configured to couple to the reference voltage, and an output; a second duplicate comparator comprising a first input configured to couple to the second switch, a second input configured to couple to the reference voltage, and an output; an expander circuit comprising at least four inputs, wherein each of the outputs of the first and second comparators is coupled to an input of the expander circuit, and wherein each of the outputs of the first and second duplicate comparators is coupled an input of the expander circuit, the expander circuit comprising an output; an isolator circuit comprising an input and an output, wherein the input is coupled to the output of the expander circuit; and a controller coupled to the output of the isolator circuit, wherein the controller is configure to: compare the output of the first comparator with the output of the first duplicate comparator; compare the output of the second comparator with the output of the second duplicate comparator; and determine activation or deactivation of a surgical instrument coupled to the controller based on the comparison.

Example 8. The isolated interface circuit of Example 7, comprising an analog to digital converter (ADC) coupled to the controller through the isolator circuit; and a switch identification circuit coupled to the ADC, wherein the switch identification circuit is configured to identify a type of switch.

Example 9. The isolated interface circuit of any one or more of Examples 7 through 8, comprising any one of a comparator reference voltage, supply voltage, or switch voltage applied to the ADC, or any combination thereof.

Example 10. The isolated interface circuit of any one or more of Examples 7 through 9, wherein the isolator circuit comprises a digital isolator circuit.

Example 11. The isolated interface circuit of any one or more of Examples 7 through 10, wherein the first and second comparators and the first and second duplicate comparators are configured to couple to a footswitch.

Example 12. The isolated interface circuit of Example 11, wherein the footswitch comprises a first and second switch, wherein the first switch represents a first state of the footswitch and the second switch represents a second state of the footswitch.

Example 13. The isolated interface circuit of any one or more of Examples 11 through 12, wherein the footswitch comprises multiple footswitches, wherein each of the multiple footswitches comprises a footswitch identification circuit coupled to an analog to digital converter (ADC) coupled to the controller through the isolator circuit, wherein each of the footswitch identification circuits is configured to identify a type of foot switch.

Example 14. The isolated interface circuit of any one or more of Examples 7 through 13, wherein the output of the isolator circuit is a single digital serial communication bus.

Example 15. A method of mitigating erroneous outputs from an isolated interface circuit for a modular energy system, the method comprising: receiving, at a first input of a first comparator, a state of a first switch of a first footswitch coupled to the first input of the first comparator and a reference voltage coupled to a second input of the first comparator; receiving, at a first input of a first duplicate comparator, the state of the first switch coupled to the first input of the first duplicate comparator and the reference voltage coupled to a second input of the first duplicate comparator; comparing, by a controller coupled to outputs of the first comparator and the first duplicate comparator, the output of the first comparator with the output of the first duplicate comparator; and determining, by the controller, activation or deactivation of a surgical instrument coupled to the controller based on the comparison.

Example 16. The method of Example 15, comprising: receiving, by an analog to digital converter (ADC) coupled to the controller, a first footswitch identification signal; and identifying, by the controller, a type of the first footswitch based on the first footswitch identification signal.

Example 17. The method of Example 16, comprising: receiving, by the ADC, any one of a comparator reference voltage, supply voltage, or switch voltage; measuring, by the controller, the comparator reference voltage, supply voltage, or switch voltage applied to the ADC; determining, by the controller, that the comparator reference voltage, supply voltage, or switch voltage is within predetermined limits; and enabling, by the controller, activation of the surgical instrument in the instance that the comparator reference voltage, supply voltage, or switch voltage is within the predetermined limits; disabling, by the controller, activation of the surgical instrument in the instance that the comparator reference voltage, supply voltage, or switch voltage is not within the predetermined limits.

Example 18. The method of any one or more of Examples 15 through 17, comprising: receiving, at a first input of a second comparator, a state of a second switch of the first footswitch coupled to the first input of the second comparator and a reference voltage coupled to a second input of the second comparator; receiving, at a first input of a second duplicate comparator, the state of the second switch coupled to the first input of the second duplicate comparator and the reference voltage coupled to a second input of the second duplicate comparator; comparing, by a controller coupled to outputs of the second comparator and the second duplicate comparator, the output of the second comparator with the output of the second duplicate comparator; and determining, by the controller, activation or deactivation of a surgical instrument coupled to the controller based on the comparison.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. An isolated interface circuit for a modular energy system, the isolated interface circuit comprising:
   a comparator comprising a first input configured to couple to a switch, a second input configured to couple to a reference voltage, and an output;
   a duplicate comparator comprising a first input configured to couple to the switch, a second input configured to couple to the reference voltage, and an output;
   an expander circuit comprising at least two inputs, wherein the output of the comparator is coupled to one of the at least two inputs of the expander circuit, and wherein the output of the duplicate comparator is coupled to other of the at least two inputs of the expander circuit, the expander circuit comprising an output;
   an isolator circuit comprising an input and an output, wherein the input is coupled to the output of the expander circuit; and
   a controller coupled to the output of the isolator circuit, wherein the controller is configured to:
      compare the output of the comparator with the output of the duplicate comparator; and
      determine activation or deactivation of a surgical instrument coupled to the controller based on the comparison.

2. The isolated interface circuit of claim 1, comprising:
an analog to digital converter (ADC) coupled to the controller through the isolator circuit; and
a switch identification circuit coupled to the ADC, wherein the switch identification circuit is configured to identify a type of switch coupled to the comparator and the duplicate comparator.

3. The isolated interface circuit of claim 1, wherein the isolator circuit comprises a digital isolator circuit.

4. The isolated interface circuit of claim 1, wherein the comparator and duplicate comparator are configured to couple to multiple switches, the comparator comprising multiple comparators configured to couple to each of the multiple switches, and the duplicate comparator comprising multiple comparators configured to couple to each of the multiple switches; and wherein the controller is configured to compare the outputs of each of the multiple comparators with the corresponding outputs of each of the duplicate comparators.

5. The isolated interface circuit of claim 1, wherein the comparator and duplicate comparator are configured to couple to a footswitch.

6. The isolated interface circuit of claim 1, wherein the output of the isolator circuit is a digital serial communication bus.

7. An isolated interface circuit for a modular energy system, the isolated interface circuit comprising:
a first comparator comprising a first input configured to couple to a first switch, a second input configured to couple to a reference voltage, and an output;
a second comparator comprising a first input configured to couple to a second switch, a second input configured to couple to the reference voltage, and an output;
a first duplicate comparator comprising a first input configured to couple to the first switch, a second input configured to couple to the reference voltage, and an output;
a second duplicate comparator comprising a first input configured to couple to the second switch, a second input configured to couple to the reference voltage, and an output;
an expander circuit comprising at least four inputs, wherein each of the outputs of the first and second comparators is coupled to an input of the expander circuit, and wherein each of the outputs of the first and second duplicate comparators is coupled an input of the expander circuit, the expander circuit comprising an output;
an isolator circuit comprising an input and an output, wherein the input is coupled to the output of the expander circuit; and
a controller coupled to the output of the isolator circuit, wherein the controller is configure to:
compare the output of the first comparator with the output of the first duplicate comparator;
compare the output of the second comparator with the output of the second duplicate comparator; and
determine activation or deactivation of a surgical instrument coupled to the controller based on the comparison.

8. The isolated interface circuit of claim 7, comprising:
an analog to digital converter (ADC) coupled to the controller through the isolator circuit; and
a switch identification circuit coupled to the ADC, wherein the switch identification circuit is configured to identify a type of switch.

9. The isolated interface circuit of claim 7, comprising any one of a comparator reference voltage, supply voltage, or switch voltage applied to the ADC, or any combination thereof.

10. The isolated interface circuit of claim 7, wherein the isolator circuit comprises a digital isolator circuit.

11. The isolated interface circuit of claim 7, wherein the first and second comparators and the first and second duplicate comparators are configured to couple to a footswitch.

12. The isolated interface circuit of claim 11, wherein the footswitch comprises a first and second switch, wherein the first switch represents a first state of the footswitch and the second switch represents a second state of the footswitch.

13. The isolated interface circuit of claim 11, wherein the footswitch comprises multiple footswitches, wherein each of the multiple footswitches comprises a footswitch identification circuit coupled to an analog to digital converter (ADC) coupled to the controller through the isolator circuit, wherein each of the footswitch identification circuits is configured to identify a type of foot switch.

14. The isolated interface circuit of claim 7, wherein the output of the isolator circuit is a single digital serial communication bus.

15. An isolated interface circuit for a modular energy system, the isolated interface circuit comprising:
a comparator comprising a first input configured to couple to a switch, a second input configured to couple to a reference voltage, and an output;
a duplicate comparator comprising a first input configured to couple to the switch, a second input configured to couple to the reference voltage, and an output;
an expander circuit comprising at least two inputs, wherein the output of the comparator is coupled to one of the at least two inputs of the expander circuit, and wherein the output of the duplicate comparator is coupled to other of the at least two inputs of the expander circuit, the expander circuit comprising an output;
an isolator circuit comprising an input and an output, wherein the input is coupled to the output of the expander circuit; and
a controller coupled to the output of the isolator circuit, wherein the controller is configured to:
compare the output of the comparator with the output of the duplicate comparator; and
determine a first state or a second state of a surgical instrument coupled to the controller based on the comparison, wherein the second state is different than the first state.

16. The isolated interface circuit of claim 15, comprising:
an analog to digital converter (ADC) coupled to the controller through the isolator circuit; and
a switch identification circuit coupled to the ADC, wherein the switch identification circuit is configured to identify a type of switch coupled to the comparator and the duplicate comparator.

17. The isolated interface circuit of claim 15, wherein the isolator circuit comprises a digital isolator circuit.

18. The isolated interface circuit of claim 15, wherein the comparator and duplicate comparator are configured to couple to multiple switches, the comparator comprising multiple comparators configured to couple to each of the multiple switches, and the duplicate comparator comprising multiple comparators configured to couple to each of the multiple switches, and wherein the controller is configured to compare the outputs of each of the multiple comparators with the corresponding outputs of each of the duplicate comparators.

19. The isolated interface circuit of claim 15, wherein the comparator and duplicate comparator are configured to couple to a footswitch.

20. The isolated interface circuit of claim 15, wherein the output of the isolator circuit is a digital serial communication bus.

* * * * *